United States Patent
Kim et al.

(10) Patent No.: US 12,223,817 B2
(45) Date of Patent: Feb. 11, 2025

(54) WEARABLE DEVICE AND METHOD FOR IDENTIFYING USER'S STATE

(71) Applicant: Samsung Electronics Co., Ltd., Suwon-si (KR)

(72) Inventors: Hyeonseong Kim, Suwon-si (CN); Chanung Park, Suwon-si (KR); Jeongmin Park, Suwon-si (CN)

(73) Assignee: Samsung Electronics Co., Ltd., Suwon-si (KR)

( * ) Notice: Subject to any disclaimer, the term of this patent is extended or adjusted under 35 U.S.C. 154(b) by 31 days.

(21) Appl. No.: 18/343,973

(22) Filed: Jun. 29, 2023

(65) Prior Publication Data

US 2024/0013643 A1    Jan. 11, 2024

Related U.S. Application Data

(63) Continuation of application No. PCT/KR2023/008796, filed on Jun. 23, 2023.

(30) Foreign Application Priority Data

| Jul. 8, 2022 | (KR) | 10-2022-0084683 |
| Jul. 26, 2022 | (KR) | 10-2022-0092803 |
| May 18, 2023 | (KR) | 10-2023-0064648 |

(51) Int. Cl.
 *G08B 21/02* (2006.01)
(52) U.S. Cl.
 CPC .............. *G08B 21/02* (2013.01)
(58) Field of Classification Search
 CPC ........................................... G08B 21/02
 See application file for complete search history.

(56) References Cited

U.S. PATENT DOCUMENTS

| 9,782,128 B2 | 10/2017 | Lee et al. |
| 10,004,430 B2 | 6/2018 | Pae |

(Continued)

FOREIGN PATENT DOCUMENTS

| CN | 106575471 A | 4/2017 |
| JP | 2015016216 A | 1/2015 |

(Continued)

OTHER PUBLICATIONS

PCT International Search Report dated Oct. 12, 2023 for PCT/KR2023/008796.
PCT Written Opinion dated Oct. 12, 2023 for PCT/KR2023/008796.

*Primary Examiner* — Mohamed Barakat
(74) *Attorney, Agent, or Firm* — Nixon & Vanderhye P.C.

(57) ABSTRACT

A wearable device includes a communication circuit, at least one sensor, and a processor, wherein the processor is configured to identify a distance between the wearable device and an external electronic device through the communication circuit, during identifying that a user wearing the wearable device is sleeping, compare data obtained through the at least one sensor to first reference data to identify a first state of the user while the user is sleeping based at least in part on identifying that the distance that is less than a reference distance, and compare the data to second reference data to identify a second state of the user while the user is awake, which is distinct to the first reference data based at least in part on identifying that the distance that is greater than or equal to the reference distance.

20 Claims, 26 Drawing Sheets

(56) References Cited

U.S. PATENT DOCUMENTS

| | | | |
|---|---|---|---|
| 10,147,296 B2 | 12/2018 | Gregg | |
| 10,866,914 B2 | 12/2020 | Oh et al. | |
| 11,410,540 B2 | 8/2022 | Zhang et al. | |
| 11,450,230 B2* | 9/2022 | Lim | H04M 1/72412 |
| 11,657,821 B2 | 5/2023 | Nagata | |
| 11,684,279 B2* | 6/2023 | Jäntti | A61B 5/349 |
| | | | 600/515 |
| 11,857,815 B2* | 1/2024 | Bornack | A41D 1/002 |
| 2008/0001735 A1* | 1/2008 | Tran | A43B 3/48 |
| | | | 340/539.22 |
| 2017/0193787 A1* | 7/2017 | Devdas | G08B 25/005 |
| 2019/0015045 A1 | 1/2019 | Li | |
| 2020/0138308 A1* | 5/2020 | Lee | A61B 5/02108 |
| 2022/0036714 A1* | 2/2022 | Tan | A61B 5/1121 |
| 2022/0201433 A1 | 6/2022 | Yang et al. | |
| 2022/0375591 A1* | 11/2022 | Kinnunen | G16H 50/20 |
| 2023/0248305 A1 | 8/2023 | Lee et al. | |
| 2024/0127683 A1 | 4/2024 | Tan et al. | |

FOREIGN PATENT DOCUMENTS

| | | |
|---|---|---|
| JP | 2020124389 A | 8/2020 |
| JP | 2021086605 A | 6/2021 |
| KR | 10-2016-0086102 A | 7/2016 |
| KR | 101725624 B1 | 4/2017 |
| KR | 10-20170084446 A | 7/2017 |
| KR | 10-1803359 B1 | 11/2017 |
| KR | 20180010441 A | 1/2018 |
| KR | 20180028358 A | 3/2018 |
| KR | 10-2061913 B1 | 12/2019 |
| KR | 102052883 B1 | 12/2019 |
| KR | 20200104758 A | 9/2020 |
| KR | 102344338 B1 | 12/2021 |
| KR | 102359301 B1 | 2/2022 |
| KR | 10-2419586 B1 | 7/2022 |
| WO | WO 2018088695 A1 | 5/2018 |
| WO | 2019103620 A2 | 5/2019 |
| WO | WO 2020021861 A1 | 1/2020 |

\* cited by examiner

WEARABLE DEVICE AND METHOD FOR IDENTIFYING USER'S STATE

CROSS-REFERENCE TO RELATED APPLICATION(S)

This application is a continuation application of international application No. PCT/KR2023/008796, filed on Jun. 23, 2023, which is based on and claims the benefit of Korean patent application number 10-2022-0084683 filed on Jul. 8, 2022, Korean patent application number 10-2022-0092803 filed on Jul. 26, 2022, and Korean patent application number 10-2023-0064648 filed on May 18, 2023 the disclosures of each of which are all hereby incorporated by reference herein in their entireties.

BACKGROUND

Technical Field

Certain example embodiments relate to a wearable device and/or a method for identifying a user's state.

Description of Related Art

Various services are provided through a wearable device. The wearable device may be worn and operated on a part of the user's body. The wearable device may identify biometric information of the user while being worn on a part of the user's body, and provide a service based on the user's biometric information. For example, the wearable device may identify the user's biometric information by using a plurality of sensors. The wearable device may identify various activity states of the user based on the identified user's biometric information.

SUMMARY

According to an example embodiment, a wearable device may comprise a communication circuit, at least one sensor, and at least one processor operably coupled, directly or indirectly, with the communication circuit and the at least one sensor. The processor may be configured to identify a distance between the wearable device and an external electronic device through the communication circuit, during identifying that a user wearing the wearable device is sleeping. The processor may be configured to, based at least in part on identifying that the distance that is less than a reference distance, compare data obtained through the at least one sensor to first reference data to identify a first state of the user while the user is sleeping, and execute a predetermined first function according to a comparison between the data and the first reference data. The processor may be configured to, based at least in part on identifying that the distance that is greater than or equal to the reference distance, compare the data to second reference data to identify a second state of the user while the user is awake, which is distinct to the first reference data, and execute a predetermined second function according to a comparison between the data and the second reference data.

According to an example embodiment, a method of a wearable device may comprise identifying a distance between the wearable device and an external electronic device through a communication circuit of the wearable device, during identifying that a user wearing the wearable device is sleeping. The method may comprise, based at least in part on identifying that the distance is less than a reference distance, comparing data obtained through at least one sensor of the wearable device to first reference data to identify a first state of the user while the user is sleeping, and executing a predetermined first function according to a comparison between the data and the first reference data. The method may comprise, based at least in part on identifying that the distance is greater than or equal to the reference distance, comparing the data to second reference data to identify a second state of the user while the user is awake, which is distinct to the first reference data, and executing a predetermined second function according to a comparison between the data and the second reference data.

BRIEF DESCRIPTION OF THE DRAWINGS

The above and other aspects, features, and advantages of certain embodiments of the disclosure will be more apparent from the following description taken in conjunction with the accompanying drawings, in which.

DETAILED DESCRIPTION

Figure 1:
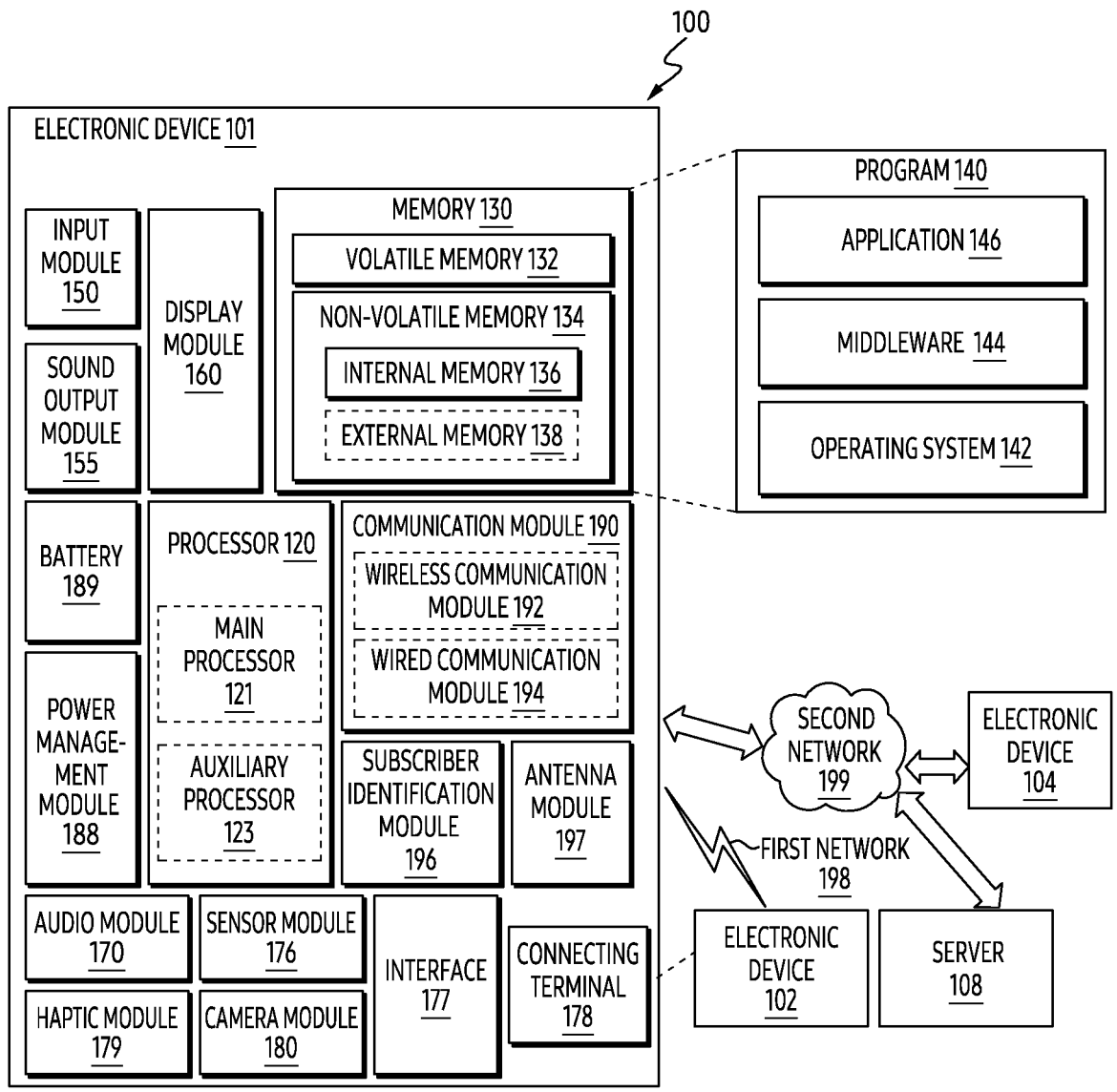
FIG. 1 is a block diagram of an electronic device in a network environment according to an example embodiment.

FIG. 1 is a block diagram illustrating an electronic device 101 in a network environment 100 according to various embodiments.

Referring to FIG. 1, the electronic device 101 in the network environment 100 may communicate with an electronic device 102 via a first network 198 (e.g., a short-range wireless communication network), or at least one of an electronic device 104 or a server 108 via a second network 199 (e.g., a long-range wireless communication network). According to an embodiment, the electronic device 101 may communicate with the electronic device 104 via the server 108. According to an embodiment, the electronic device 101 may include a processor 120, memory 130, an input module 150, a sound output module 155, a display module 160, an audio module 170, a sensor module 176, an interface 177, a connecting terminal 178, a haptic module 179, a camera module 180, a power management module 188, a battery 189, a communication module 190, a subscriber identification module (SIM) 196, or an antenna module 197. In some embodiments, at least one of the components (e.g., the connecting terminal 178) may be omitted from the electronic device 101, or one or more other components may be added in the electronic device 101. In some embodiments, some of the components (e.g., the sensor module 176, the camera module 180, or the antenna module 197) may be implemented as a single component (e.g., the display module 160).

The processor 120 may execute, for example, software (e.g., a program 140) to control at least one other component (e.g., a hardware or software component) of the electronic device 101 coupled with the processor 120, and may perform various data processing or computation. According to one embodiment, as at least part of the data processing or computation, the processor 120 may store a command or data received from another component (e.g., the sensor module 176 or the communication module 190) in volatile memory 132, process the command or the data stored in the volatile memory 132, and store resulting data in non-volatile memory 134. According to an embodiment, the processor 120 may include a main processor 121 (e.g., a central processing unit (CPU) or an application processor (AP)), or an auxiliary processor 123 (e.g., a graphics processing unit (GPU), a neural processing unit (NPU), an image signal processor (ISP), a sensor hub processor, or a communication processor (CP)) that is operable independently from, or in conjunction with, the main processor 121. For example, when the electronic device 101 includes the main processor 121 and the auxiliary processor 123, the auxiliary processor 123 may be adapted to consume less power than the main processor 121, or to be specific to a specified function. The auxiliary processor 123 may be implemented as separate from, or as part of the main processor 121.

The auxiliary processor 123 may control at least some of functions or states related to at least one component (e.g., the display module 160, the sensor module 176, or the communication module 190) among the components of the electronic device 101, instead of the main processor 121 while the main processor 121 is in an inactive (e.g., sleep) state, or together with the main processor 121 while the main processor 121 is in an active state (e.g., executing an application). According to an embodiment, the auxiliary processor 123 (e.g., an image signal processor or a communication processor) may be implemented as part of another component (e.g., the camera module 180 or the communication module 190) functionally related to the auxiliary processor 123. According to an embodiment, the auxiliary processor 123 (e.g., the neural processing unit) may include a hardware structure specified for artificial intelligence model processing. An artificial intelligence model may be generated by machine learning. Such learning may be performed, e.g., by the electronic device 101 where the artificial intelligence is performed or via a separate server (e.g., the server 108). Learning algorithms may include, but are not limited to, e.g., supervised learning, unsupervised learning, semi-supervised learning, or reinforcement learning. The artificial intelligence model may include a plurality of artificial neural network layers. The artificial neural network may be a deep neural network (DNN), a convolutional neural network (CNN), a recurrent neural network (RNN), a restricted boltzmann machine (RBM), a deep belief network (DBN), a bidirectional recurrent deep neural network (BRDNN), deep Q-network or a combination of two or more thereof but is not limited thereto. The artificial intelligence model may, additionally or alternatively, include a software structure other than the hardware structure.

The memory 130 may store various data used by at least one component (e.g., the processor 120 or the sensor module 176) of the electronic device 101. The various data may include, for example, software (e.g., the program 140) and input data or output data for a command related therereto. The memory 130 may include the volatile memory 132 or the non-volatile memory 134.

The program 140 may be stored in the memory 130 as software, and may include, for example, an operating system (OS) 142, middleware 144, or an application 146.

The input module 150 may receive a command or data to be used by another component (e.g., the processor 120) of the electronic device 101, from the outside (e.g., a user) of the electronic device 101. The input module 150 may include, for example, a microphone, a mouse, a keyboard, a key (e.g., a button), or a digital pen (e.g., a stylus pen).

The sound output module 155 may output sound signals to the outside of the electronic device 101. The sound output module 155 may include, for example, a speaker or a receiver. The speaker may be used for general purposes, such as playing multimedia or playing record. The receiver may be used for receiving incoming calls. According to an embodiment, the receiver may be implemented as separate from, or as part of the speaker.

The display module 160 may visually provide information to the outside (e.g., a user) of the electronic device 101. The display module 160 may include, for example, a display, a hologram device, or a projector and control circuitry to control a corresponding one of the display, hologram device, and projector. According to an embodiment, the display module 160 may include a touch sensor adapted to detect a touch, or a pressure sensor adapted to measure the intensity of force incurred by the touch.

The audio module 170 may convert a sound into an electrical signal and vice versa. According to an embodiment, the audio module 170 may obtain the sound via the input module 150, or output the sound via the sound output module 155 or a headphone of an external electronic device (e.g., an electronic device 102) directly (e.g., wiredly) or wirelessly coupled with the electronic device 101.

The sensor module 176 may detect an operational state (e.g., power or temperature) of the electronic device 101 or an environmental state (e.g., a state of a user) external to the electronic device 101, and then generate an electrical signal or data value corresponding to the detected state. According to an embodiment, the sensor module 176 may include, for example, a gesture sensor, a gyro sensor, an atmospheric pressure sensor, a magnetic sensor, an acceleration sensor, a grip sensor, a proximity sensor, a color sensor, an infrared (IR) sensor, a biometric sensor, a temperature sensor, a humidity sensor, or an illuminance sensor.

The interface 177 may support one or more specified protocols to be used for the electronic device 101 to be coupled with the external electronic device (e.g., the electronic device 102) directly (e.g., wiredly) or wirelessly. According to an embodiment, the interface 177 may include, for example, a high definition multimedia interface (HDMI), a universal serial bus (USB) interface, a secure digital (SD) card interface, or an audio interface.

A connecting terminal 178 may include a connector via which the electronic device 101 may be physically connected with the external electronic device (e.g., the electronic device 102). According to an embodiment, the connecting terminal 178 may include, for example, a HDMI connector, a USB connector, a SD card connector, or an audio connector (e.g., a headphone connector).

The haptic module 179 may convert an electrical signal into a mechanical stimulus (e.g., a vibration or a movement) or electrical stimulus which may be recognized by a user via his tactile sensation or kinesthetic sensation. According to an embodiment, the haptic module 179 may include, for example, a motor, a piezoelectric element, or an electric stimulator.

The camera module 180 may capture a still image or moving images. According to an embodiment, the camera module 180 may include one or more lenses, image sensors, image signal processors, or flashes.

The power management module 188 may manage power supplied to the electronic device 101. According to an embodiment, the power management module 188 may be implemented as at least part of, for example, a power management integrated circuit (PMIC).

The battery 189 may supply power to at least one component of the electronic device 101. According to an embodiment, the battery 189 may include, for example, a primary cell which is not rechargeable, a secondary cell which is rechargeable, or a fuel cell.

The communication module 190 may support establishing a direct (e.g., wired) communication channel or a wireless communication channel between the electronic device 101 and the external electronic device (e.g., the electronic device 102, the electronic device 104, or the server 108) and performing communication via the established communication channel. The communication module 190 may include one or more communication processors that are operable independently from the processor 120 (e.g., the application processor (AP)) and supports a direct (e.g., wired) communication or a wireless communication. According to an embodiment, the communication module 190 may include a wireless communication module 192 (e.g., a cellular communication module, a short-range wireless communication module, or a global navigation satellite system (GNSS) communication module) or a wired communication module 194 (e.g., a local area network (LAN) communication module or a power line communication (PLC) module). A corresponding one of these communication modules may communicate with the external electronic device via the first network 198 (e.g., a short-range communication network, such as Bluetooth™, wireless-fidelity (Wi-Fi) direct, or infrared data association (IrDA)) or the second network 199 (e.g., a long-range communication network, such as a legacy cellular network, a 5G network, a next-generation communication network, the Internet, or a computer network (e.g., LAN or wide area network (WAN)). These various types of communication modules may be implemented as a single component (e.g., a single chip), or may be implemented as multi components (e.g., multi chips) separate from each other. The wireless communication module 192 may identify and authenticate the electronic device 101 in a communication network, such as the first network 198 or the second network 199, using subscriber information (e.g., international mobile subscriber identity (IMSI)) stored in the subscriber identification module 196.

The wireless communication module 192 may support a 5G network, after a 4G network, and next-generation communication technology, e.g., new radio (NR) access technology. The NR access technology may support enhanced mobile broadband (eMBB), massive machine type communications (mMTC), or ultra-reliable and low-latency communications (URLLC). The wireless communication module 192 may support a high-frequency band (e.g., the mmWave band) to achieve, e.g., a high data transmission rate. The wireless communication module 192 may support various technologies for securing performance on a high-frequency band, such as, e.g., beamforming, massive multiple-input and multiple-output (massive MIMO), full dimensional MIMO (FD-MIMO), array antenna, analog beam-forming, or large scale antenna. The wireless communication module 192 may support various requirements specified in the electronic device 101, an external electronic device (e.g., the electronic device 104), or a network system (e.g., the second network 199). According to an embodiment, the wireless communication module 192 may support a peak data rate (e.g., 20 Gbps or more) for implementing eMBB, loss coverage (e.g., 164 dB or less) for implementing mMTC, or U-plane latency (e.g., 0.5 ms or less for each of downlink (DL) and uplink (UL), or a round trip of 1 ms or less) for implementing URLLC.

The antenna module 197 may transmit or receive a signal or power to or from the outside (e.g., the external electronic device) of the electronic device 101. According to an embodiment, the antenna module 197 may include an antenna including a radiating element composed of a conductive material or a conductive pattern formed in or on a substrate (e.g., a printed circuit board (PCB)). According to an embodiment, the antenna module 197 may include a plurality of antennas (e.g., array antennas). In such a case, at least one antenna appropriate for a communication scheme used in the communication network, such as the first network 198 or the second network 199, may be selected, for example, by the communication module 190 (e.g., the wireless communication module 192) from the plurality of antennas. The signal or the power may then be transmitted or received between the communication module 190 and the external electronic device via the selected at least one antenna. According to an embodiment, another component (e.g., a radio frequency integrated circuit (RFIC)) other than the radiating element may be additionally formed as part of the antenna module 197.

According to various embodiments, the antenna module 197 may form a mmWave antenna module. According to an embodiment, the mmWave antenna module may include a printed circuit board, a RFIC disposed on a first surface (e.g., the bottom surface) of the printed circuit board, or adjacent to the first surface and capable of supporting a designated high-frequency band (e.g., the mmWave band), and a plurality of antennas (e.g., array antennas) disposed on a second surface (e.g., the top or a side surface) of the printed circuit board, or adjacent to the second surface and capable of transmitting or receiving signals of the designated high-frequency band.

At least some of the above-described components may be coupled mutually and communicate signals (e.g., commands or data) therebetween via an inter-peripheral communication scheme (e.g., a bus, general purpose input and output (GPIO), serial peripheral interface (SPI), or mobile industry processor interface (MIPI)).

According to an embodiment, commands or data may be transmitted or received between the electronic device 101 and the external electronic device 104 via the server 108 coupled with the second network 199. Each of the electronic devices 102 or 104 may be a device of a same type as, or a different type, from the electronic device 101. According to an embodiment, all or some of operations to be executed at the electronic device 101 may be executed at one or more of the external electronic devices 102, 104, or 108. For example, if the electronic device 101 should perform a function or a service automatically, or in response to a request from a user or another device, the electronic device 101, instead of, or in addition to, executing the function or the service, may request the one or more external electronic devices to perform at least part of the function or the service. The one or more external electronic devices receiving the request may perform the at least part of the function or the service requested, or an additional function or an additional service related to the request, and transfer an outcome of the performing to the electronic device 101. The electronic device 101 may provide the outcome, with or without further processing of the outcome, as at least part of a reply to the request. To that end, a cloud computing, distributed computing, mobile edge computing (MEC), or client-server computing technology may be used, for example. The electronic device 101 may provide ultra low-latency services using, e.g., distributed computing or mobile edge computing. In another embodiment, the external electronic device 104 may include an internet-of-things (IoT) device. The server 108 may be an intelligent server using machine learning and/or a neural network. According to an embodiment, the external electronic device 104 or the server 108 may be included in the second network 199. The electronic device 101 may be applied to intelligent services (e.g., smart home, smart city, smart car, or healthcare) based on 5G communication technology or IoT-related technology.

Figure 2A:
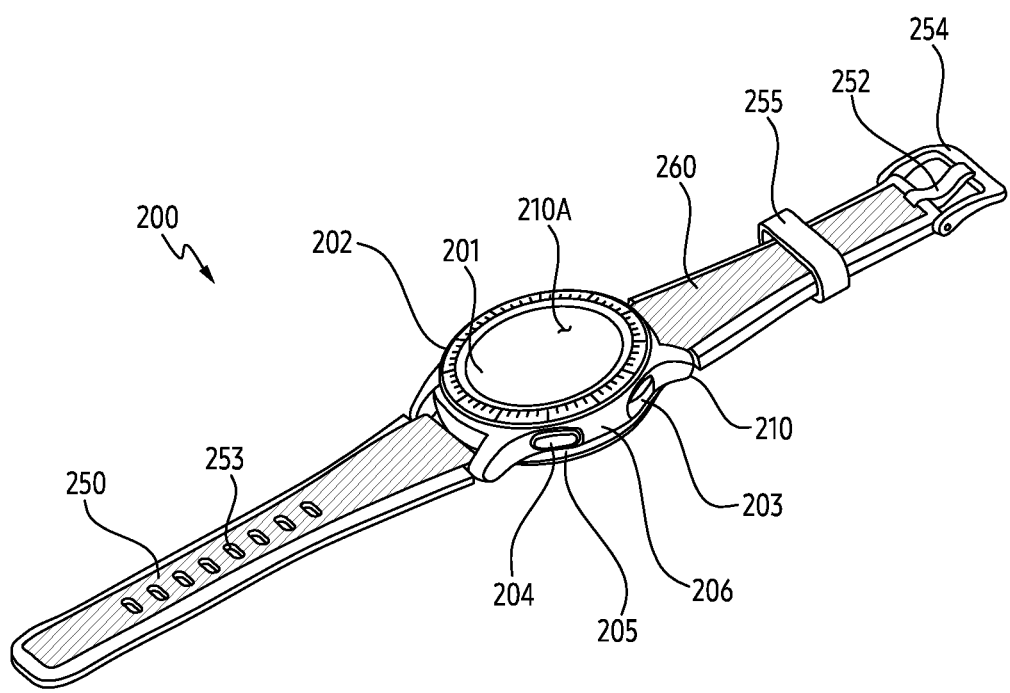
FIGS. 2A and 2B are perspective views of an electronic device according to an example embodiment.
Figure 2B:
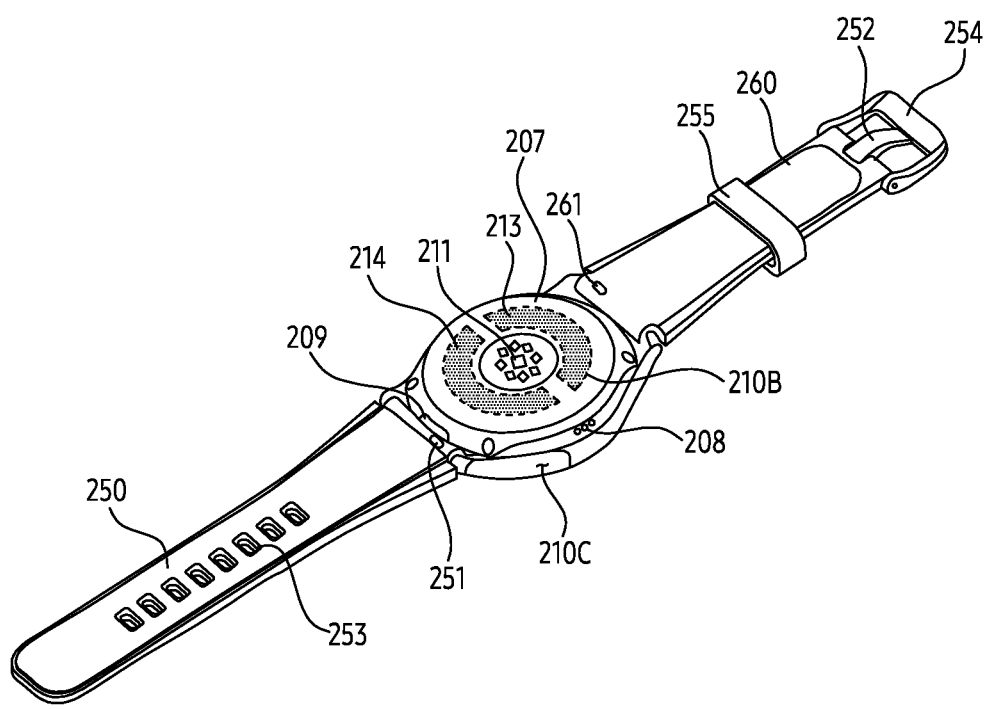

FIGS. 2A and 2B are perspective views of an electronic device according to various embodiments.

Referring to FIGS. 2A and 2B, according to an embodiment, an electronic device 200 (e.g., the electronic device 101 of FIG. 1) may include a housing 210 including a first surface (or a front surface) 210A, a second surface (or a rear surface) 210B, and a side surface 210C surrounding a space between the first surface 210A and the second surface 210B, and binding members 250 and 260 connected, directly or indirectly, to at least a part of the housing 210 and detachably couple the electronic device 200 to a part of a user's body (e.g., a wrist, an ankle, etc.). In another embodiment (not illustrated), the housing may refer to a structure forming some of the first surface 210A, the second surface 210B, and the side surface 210C of FIGS. 2A and 2B. According to an embodiment, at least a part of the first surface 210A may be formed by a substantially transparent front plate 201 (e.g., a glass plate including various coating layers, or a polymer plate). The second surface 210B may be formed by a substantially opaque rear plate 207. For example, the rear plate 207 may be formed by coating or colored glass, ceramic, polymer, metal (e.g. aluminum, stainless steel (STS), or magnesium), or a combination of at least two of the materials. The side surface 210C may be formed by a side bezel structure (or "side member") 206 coupled, directly or indirectly, to the front plate 201 and the rear plate 207 and including a metal and/or a polymer. In some embodiments, the rear plate 207 and the side bezel structure 206 may be integrally formed and may include the same material (e.g., a metal material such as aluminum). The binding members 250 and 260 may be formed of various materials and shapes. An integral unit link and a plurality of unit links may be formed to flow with each other by a woven fabric, leather, rubber, urethane, metal, ceramic, or a combination of at least two of the materials.

According to an embodiment, the electronic device 200 may include at least one of a display 220 (refer to FIG. 3), audio modules 205 and 208, a sensor module 211 comprising at least one sensor, key input devices 202, 203 and 204, and a connector hole 209. In some embodiments, the electronic device 200 may omit at least one (e.g., key the input devices 202, 203 and 204, the connector hole 209, or the sensor module 211) of the components or may additionally include another component.

The display 220 may be visually exposed, for example, through a substantial part of the front plate 201. The shape of the display 220 may be a shape corresponding to the shape of the front plate 201, and may have various shapes such as a circle, an ellipse, or a polygon. The display 220 may be coupled to, or disposed adjacent to, a touch detecting circuit, a pressure sensor capable of measuring the intensity (pressure) of a touch, and/or a fingerprint sensor.

The audio modules 205 and 208 may include a microphone hole 205 and a speaker hole 208. In the microphone hole 205, a microphone for obtaining an external sound may be disposed inside, and in some embodiments, a plurality of microphones may be disposed to detect the direction of the sound. The speaker hole 208 may be used as an external speaker and a receiver for calls. In some embodiments, the speaker hole 208 and the microphone hole 205 may be implemented as one hole, or a speaker may be included without the speaker hole 208 (e.g., a piezo speaker).

The sensor module 211 may generate an electrical signal or data value corresponding to an internal operating state of the electronic device 200 or an external environmental state. The sensor module 211 may include, for example, a biometric sensor module 211 (e.g., an HRM sensor) disposed on the second surface 210B of the housing 210. The electronic device 200 may further include at least one of a sensor module not illustrated, for example, a gesture sensor, a gyro sensor, an atmospheric pressure sensor, a magnetic sensor, an acceleration sensor, a grip sensor, a color sensor, an infrared (IR) sensor, a biometric sensor, a temperature sensor, a humidity sensor, or an illumination sensor.

The sensor module 211 may include electrode regions 213 and 214 forming a part of the surface of the electronic device 200 and a bio-signal detection circuit (not illustrated) electrically connected, directly or indirectly, to the electrode regions 213 and 214. For example, the electrode regions 213 and 214 may include a first electrode region 213 and a second electrode region 214 disposed on the second surface 210B of the housing 210. The sensor module 211 may be configured such that the electrode regions 213 and 214 obtain an electrical signal from a part of the user's body, and a bio-signal detection circuit detects bio-information of the user based on the electrical signal.

The key input devices 202, 203, and 204 may include a wheel key 202 disposed on the first surface 210A of the housing 210 and rotatable in at least one direction, and/or side key buttons 203 and 204 disposed on the side surface 210C of the housing 210. The wheel key may have a shape corresponding to the shape of the front plate 201. In another embodiment, the electronic device 200 may not include some or all of the above-described key input devices 202, 203, and 204, and the not included key input devices 202, 203, and 204 may be implemented in other forms such as a soft key on the display 220. The connector hole 209 may accommodate connectors (e.g., USB connectors) for transmitting and receiving power and/or data to and from external electronic devices, and include another connector hole (not illustrated) capable of accommodating a connector for transmitting and receiving audio signals to and from an external electronic device. For example, the electronic device 200 may further include a connector cover (not illustrated) that covers at least a part of the connector hole 209 and blocks the inflow of external foreign materials into the connector hole.

The binding members 250 and 260 may be detachably attached to at least a part of the housing 210 using locking members 251 and 261. The binding members 250 and 260 may include one or more of a fixing member 252, a fixing member fastening hole 253, a band guide member 254, and a band fixing ring 255.

The fixing member 252 may be configured to fix the housing 210 and the binding members 250 and 260 to a part of the user's body (e.g., a wrist, an ankle, etc.). Corresponding to the fixing member 252, the fixing member fastening hole 253 may fix the housing 210 and the binding members 250 and 260 to a part of the user's body. The band guide member 254 may be configured to limit a movement range of the fixing member 252 when the fixing member 252 is fastened to the fixing member fastening hole 253, and thus the binding members 250 and 260 may be closely coupled to a part of the user's body. In a state in which the fixing member 252 and the fixing member fastening hole 253 are fastened, the band fixing ring 255 may limit the movement range of the binding members 250 and 260.

Figure 3:
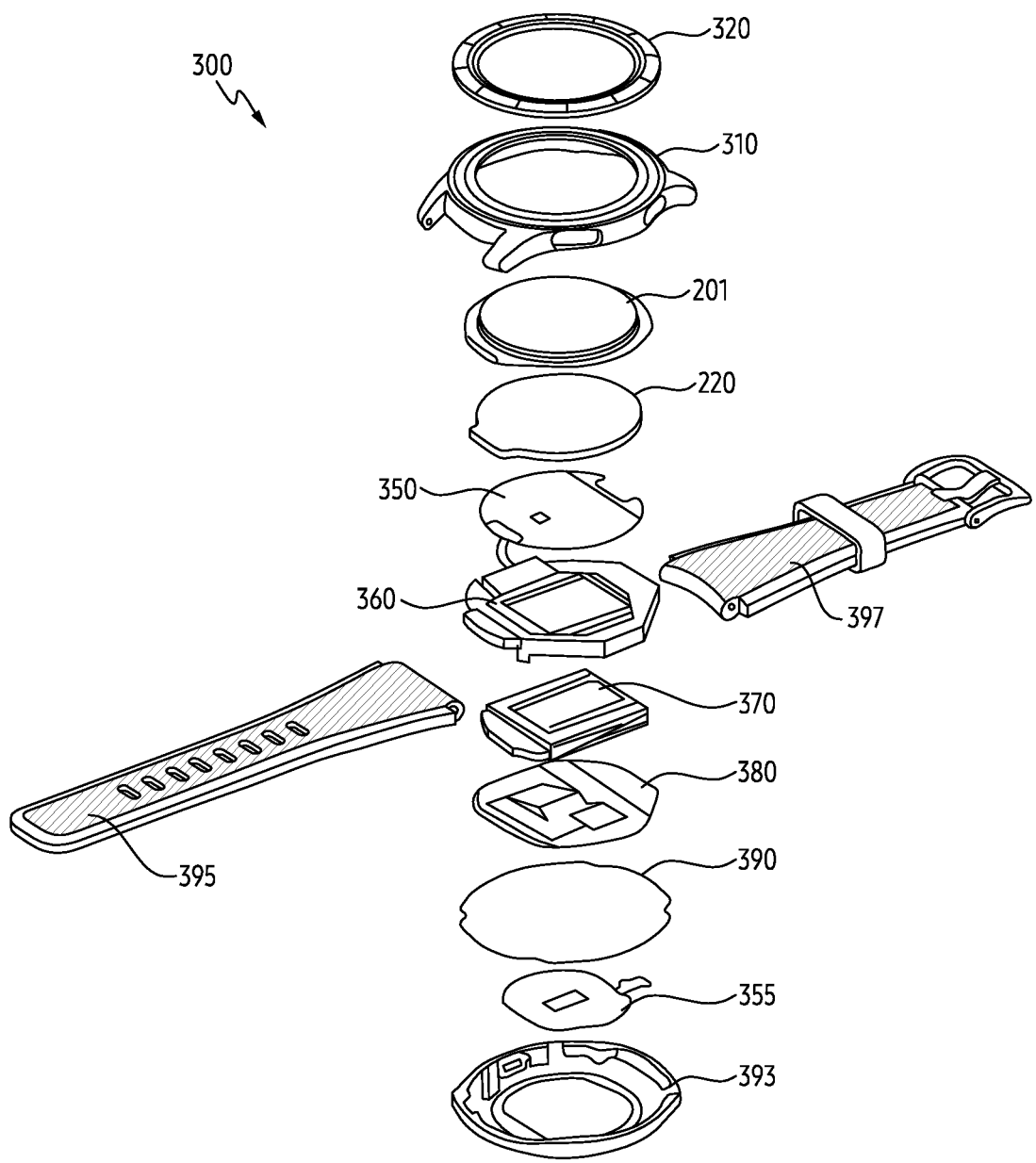
FIG. 3 is an exploded perspective view of an electronic device according to an example embodiment.

FIG. 3 is an exploded perspective view of an electronic device according to various embodiments.

Referring to FIG. 3, the electronic device 300 (e.g., the electronic device 101 of FIG. 1 or the electronic device 200 of FIGS. 2A to 2B) may include a side bezel structure 310, a wheel key 320, a front plate 201, a display 220, a first antenna 350, a second antenna 355, and a support member 360 (e.g., a bracket), a battery 370, a printed circuit board 380, a sealing member 390, a rear plate 393, and binding members 395 and 397. At least one of the components of the electronic device 300 may be the same as, or similar to, at least one of the components of the electronic device of FIGS. 1 and/or 2A to 2B, and a repeated description thereof will be omitted. The support member 360 may be disposed inside the electronic device 300 to be connected, directly or indirectly, to the side bezel structure 310 or may be integrally formed with the side bezel structure 310. The support member 360 may be formed of, for example, a metal material and/or a non-metal (e.g., a polymer) material. In the support member 360, the display 220 may be coupled, directly or indirectly, to one surface and the printed circuit board 380 may be coupled to the other surface. A processor, a memory, and/or an interface may be mounted on the printed circuit board 380. The processor may include, for example, one or more of a central processing unit, a graphic processing unit (GPU), an application processor, a sensor processor, or a communication processor.

The memory may include, for example, a volatile memory or a nonvolatile memory. The interface may include, for example, a high definition multimedia interface (HDMI), a universal serial bus (USB) interface, an SD card interface, and/or an audio interface. For example, the interface may electrically or physically connect the electronic device 300 to an external electronic device, and may include a USB connector, an SD card/MMC connector, or an audio connector.

The battery 370 is a device for supplying power to at least one component of the electronic device 200/300, and may include, for example, a non-rechargeable primary battery, a rechargeable secondary battery, or a fuel battery. At least a part of the battery 370 may be disposed on substantially the same plane as, for example, the printed circuit board 380. The battery 370 may be integrally disposed inside the electronic device 200/300 or may be detachably disposed from the electronic device 200/300.

The first antenna 350 may be disposed between the display 220 and the support member 360. The first antenna 350 may include, for example, a near field communication (NFC) antenna, a wireless charging antenna, and/or a magnetic secure transmission (MST) antenna. For example, the first antenna 350 may perform short-range communication with an external device, wirelessly transmit and receive power required for charging, and may transmit a short-range communication signal or a self-based signal including payment data. In another embodiment, an antenna structure may be formed by the side bezel structure 310 and/or a part of the support member 360 or a combination thereof.

The second antenna 355 may be disposed between the printed circuit board 380 and the rear plate 393. For example, the second antenna 355 may include a near field communication (NFC) antenna, a wireless charging antenna, and/or a magnetic secure transmission (MST) antenna. For example, the second antenna 355 may perform short-range communication with an external device, wirelessly transmit and receive power required for charging, and may transmit a short-range communication signal or a self-based signal including payment data. In another embodiment, an antenna structure may be formed by the side bezel structure 310 and/or a part of the rear plate 393 or a combination thereof.

The sealing member 390 may be positioned between the side bezel structure 310 and the rear plate 393. The sealing member 390 may be configured to block moisture and foreign substances from flowing into the space surrounded by the side bezel structure 310 and the rear plate 393 from the outside.

According to an embodiment, the wearable device (e.g., the electronic device 101 of FIG. 1, the electronic device 200 illustrated in FIGS. 2A and 2B, or the electronic device 300 illustrated in FIG. 3) may be worn and operated by a user. For example, the wearable device may be worn on a part of the user's body (e.g., wrist, finger, or face). According to an embodiment, the wearable device may be used to identify whether a fall has occurred in the user of the wearable device. For example, the wearable device may be used to identify whether a fall has occurred while the user is sleeping. For example, a wearable device may be used to identify whether a fall has occurred while the user is awake.

An operation of the wearable device according to the above-described embodiment may be described below. The wearable device described below may correspond to the electronic device 101 of FIG. 1, the electronic device 200 of FIGS. 2A and 2B, and/or the electronic device 300 of FIG. 3.

Figure 4:
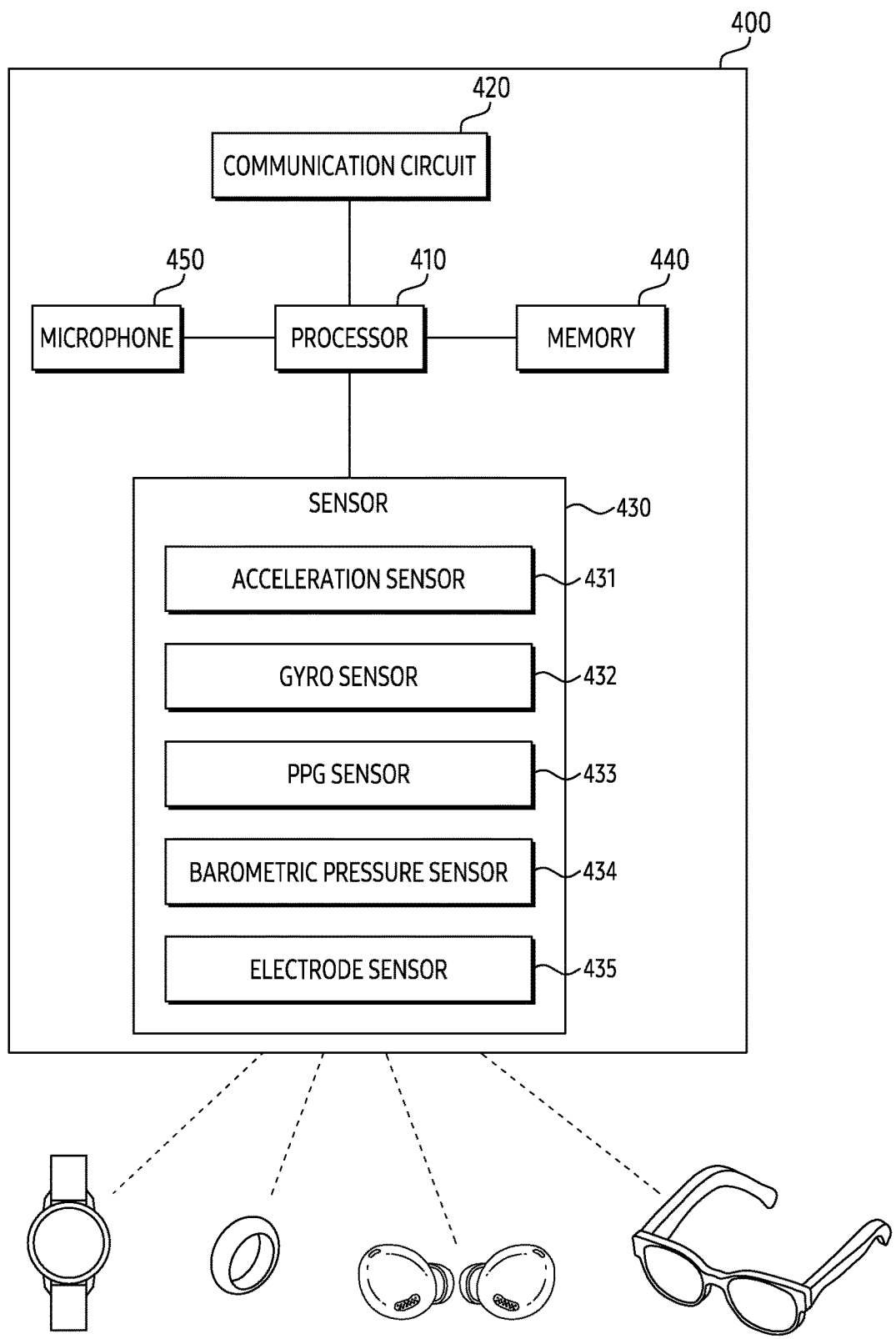
FIG. 4 is a simplified block diagram of a wearable device according to an example embodiment.

FIG. 4 is a simplified block diagram of a wearable device according to an embodiment.

Referring to FIG. 4, the wearable device 400 may be implemented in various forms. For example, the wearable device 400 may be implemented in various forms that may be worn by a user, such as a smart watch, a smart band, a smart ring, wireless earphones, or a smart glass. For example, the wearable device 400 may correspond to the electronic device 101 of FIG. 1, the electronic device 200 of FIGS. 2A and 2B, and/or the electronic device 300 of FIG. 3.

According to an embodiment, the wearable device 400 may include a processor 410, a communication circuit 420, a sensor 430, a memory 440, and/or a microphone 450. According to an embodiment, the wearable device 400 may include at least one of the processor 410, the communication circuit 420, the sensor 430, the memory 440, or the microphone 450. For example, at least a part of the processor 410, the communication circuit 420, the sensor 430, the memory 440, and the microphone 450 may be omitted according to the embodiment.

According to an embodiment, the processor 410 may correspond to the processor 120 of FIG. 1. The processor 410 may be operably coupled, directly or indirectly, with (or connected to, directly or indirectly) the communication circuit 420, the sensor 430, the memory 440, and the microphone 450. For example, when the processor 410 is operably coupled, directly or indirectly, with other components, it may indicate that the processor 410 can control other components. The processor 410 may control the communication circuit 420, the sensor 430, the memory 440, and the microphone 450. For example, the processor 410 may determine an operation moment of the sensor 430. The processor 410 may control an operation of the sensor 430. The processor 410 may activate or deactivate the sensor 430. The processor 410 may process information obtained from the sensor 430. The processor 410 herein comprises processing circuitry.

According to an embodiment, the processor 410 may be configured as at least one processor. The processor 410 may include at least one processor. According to an embodiment, the processor 410 may include a hardware component for processing data based on one or more instructions. For example, hardware components for processing data may include an arithmetical and logic unit (ALU), a field programmable gate array (FPGA), and/or a central processing unit (CPU).

According to an embodiment, the wearable device 400 may include a communication circuit 420. For example, the communication circuit 420 may correspond to at least a part of the communication module 190 (e.g communication module 190 comprising communication circuitry) of FIG. 1.

For example, the communication circuit 420 may be used for various radio access technology (RAT). For example, the communication circuit 420 may be used to perform Bluetooth communication, wireless local area network (WLAN) communication, or ultra-wideband (UWB) communication. For example, the communication circuit 420 may be used to perform cellular communication.

For example, the processor 410 may establish a connection with an external electronic device (e.g., the electronic device 102, the electronic device 104, and/or the server 108) through the communication circuit 420. For example, the processor 410 may establish a connection with the server through the communication circuit 420.

According to an embodiment, the wearable device 400 may include the sensor 430. The sensor 430 may be used to obtain various external information. For example, the sensor 430 may be used to obtain data on the user's body. For example, the sensor 430 may be used to obtain data on the user's state, data on the user's movement, and/or data on the user's heart rate. For example, the sensor 430 may correspond to the sensor module 176 of FIG. 1.

According to an embodiment, the sensor 430 may include at least one sensor. For example, the sensor 430 may include at least one of an acceleration sensor 431, a gyro sensor 432, a photoplethysmography (PPG) sensor 433, a barometric pressure sensor 434, or an electrode sensor 435.

For example, the acceleration sensor 431 may identify (or measure, or detect) the acceleration of the wearable device 400 in three directions of the x-axis, the y-axis, and the z-axis. For example, the gyro sensor 432 may identify (or measure, or detect) the angular velocity of the wearable device 400 in three directions: the x-axis, the y-axis, and the z-axis. According to an embodiment, the wearable device 400 may include a movement sensor including the acceleration sensor 431 and the gyro sensor 432.

For example, the PPG sensor 433 may be used to measure a pulse (or a change in the amount of blood in a blood vessel) by identifying a change in the amount of photosensitivity of light according to a change in the volume of the blood vessel. For example, the processor 410 may identify the user's sleep state or non-sleep state (or activity state) based on the biometric data obtained through the PPG sensor 433. For example, the PPG sensor 433 may be used to identify information on a user's heart rate change, information on a user's stress based on heart rate variability (HRV), information on a user's sleep stage, information on a user's breathing rate, and information on a user's blood pressure.

For example, the PPG sensor 433 may include one or more photodiode (PD), one or more light emitting diode (LED), or one or more laser diode (LD). The LED may convert electrical energy into light energy. The PD may convert light energy into electrical energy. When light is transmitted from the LED to the skin, the light is partially absorbed into the skin, and at least a part of the remaining reflected light may be detected through the PD. For example, the LED may emit light having one or more wavelengths. For example, the light emitted through the LED may include infrared radiation (IR) and visible light.

For example, the barometric pressure sensor 434 may identify (or measure, or detect) the barometric pressure around the wearable device 400. The processor 410 may identify the height (or altitude) at which the wearable device 400 is located from the ground based on the data on the air pressure around the wearable device 400 identified using the barometric pressure sensor 434.

For example, the sensor 430 may include the electrode sensor 435. The processor 410 may identify (or measure) electrodermal activity (EDA) through the electrode sensor 435. The processor 410 may identify information on the tension level of the skin based on the EDA.

Although not illustrated, the sensor 430 may further include a sensor for obtaining (or identifying, or measuring, or detecting) various data about the user.

For example, the sensor 430 may include a body temperature sensor. The processor 410 may measure a skin temperature of a part of the user's body through the body temperature sensor. The processor 410 may obtain the user's body temperature based on the skin temperature of a part of the user's body.

For example, the sensor 430 may include a heart rate variable (HRV) sensor. The processor 410 may measure the regularity or variability of the heart rate through the HRV sensor. The processor 410 may obtain information on regularity or variability of the heart rate through the HRV sensor.

For example, the sensor 430 may include a blood glucose sensor. The processor 410 may identify the blood glucose level of the user by identifying (or measuring) a current generated by causing an electrochemical reaction with the blood glucose in the blood.

According to an embodiment, the wearable device 400 may include the memory 440. The memory 440 may be used to store information or data. For example, the memory 440 may be used to store data obtained from a user. For example, the memory 440 may correspond to the memory 130 of FIG. 1. For example, the memory 440 may be a volatile memory unit or units. For example, the memory 440 may be a nonvolatile memory unit or units. For example, the memory 440 may be another type of computer-readable medium, such as a magnetic or optical disk. For example, the memory 440 may store data obtained based on an operation (e.g., an algorithm execution operation) performed by the processor 410. For example, the memory 440 may store data (e.g., data on a user's heart rate) obtained from the sensor 430.

According to an embodiment, the wearable device 400 may include the microphone 450 (e.g., the input module 150 of FIG. 1). The microphone 450 may identify an electrical signal corresponding to vibration of the atmosphere. For example, the processor 410 may identify sounds (e.g., snores) generated from the user using the microphone 450. The processor 410 may identify (or determine) the user's sleep state using sounds generated from the user.

According to an embodiment, the wearable device 400 may include various components in addition to the illustrated components.

For example, the wearable device 400 may include a display. The display may be used to display various screens. For example, the display may be used to output content, data, or signals through a screen. For example, the display may correspond to the display module 160 of FIG. 1.

For example, the wearable device 400 may further include an actuator. The actuator may correspond to the haptic module 179 of FIG. 1. For example, the actuator may be used to generate vibration of the wearable device 400.

For example, the wearable device 400 may further include a global positioning system (GPS) circuit. The GPS circuit may be used to identify the location of the wearable device 400.

Figure 5:
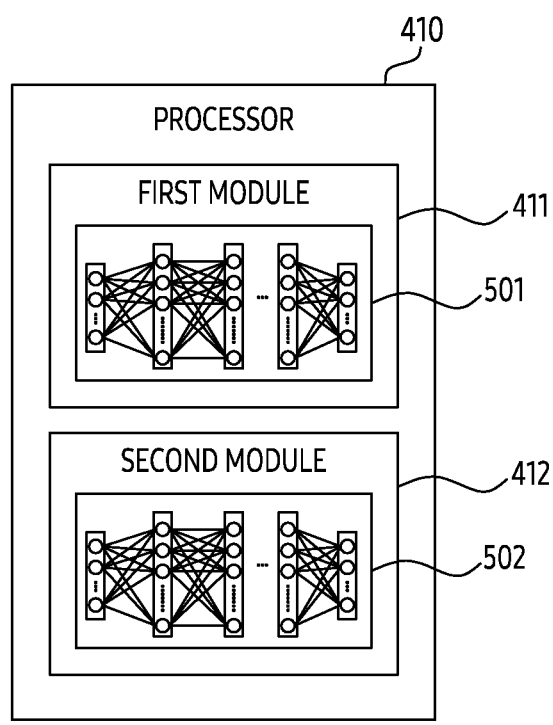
FIG. 5 illustrates an example of a first module and a second module included in a processor according to an example embodiment.

FIG. 5 illustrates an example of a first module and a second module included in a processor according to an embodiment.

Referring to FIG. 5, the processor 410 (e.g., the processor 410 of FIG. 4) may include a first module 411 and a second module 412. For example, the first module 411 may be used to identify whether a fall occurs to the user while the user is sleeping using the first model 501 indicated by a plurality of first parameters. For example, the first module 411 may be referred to as a bed fall detection module. For example, the second module 412 may be used to identify whether a fall occurs to the user while the user is awake using the second model 502 indicated by a plurality of second parameters. For example, the second module may be referred to as a general fall detection module (or a hard fall detection module).

According to an embodiment, the first model 501 and the second model 502 may be indicated by a plurality of parameters related to a neural network (or machine learning). For example, the first model 501 of the processor 410 may be indicated by a plurality of first parameters related to the neural network. For example, the second model 502 may be indicated by a plurality of second parameters related to the neural network.

For example, each of the first model 501 and the second model 502 may include a set of parameters related to the neural network. For example, the plurality of first parameters and/or the plurality of second parameters may represent a plurality of nodes included in the neural network and/or an assigned weight to a connection between the plurality of nodes.

According to an embodiment, the processor 410 may identify whether a fall has occurred to the user while the user is sleeping using the first module 411. For example, the processor 410 may identify whether a fall has occurred to the user while the user is sleeping, by comparing the data obtained through the sensor 430 (e.g., the sensor 430 of FIG. 4) with the first reference data, using the first model 501 of the first module 411. For example, the processor 410 may use the first module 411 to identify whether the user has fallen from the bed while sleeping. According to an embodiment, after a fall occurs to the user, the processor 410 may identify that an impact has occurred to the user using the first module 411 and identify (or determine) whether the user is conscious.

According to an embodiment, the processor 410 may identify whether a fall has occurred to the user while the user is awake by using the second module 412. For example, the processor 410 may identify whether a fall has occurred to the user while the user is awake, by comparing the data obtained through the sensor 430 with the second reference data, using the second model 502 of the second module 412. For example, the processor 410 may identify a type of fall that occurs to the user using the second module 412. For example, the processor 410 may identify a type of fall that occurs to the user as at least one of a fall while walking, a fall while running, a fall on a slope (e.g., ramp or stairs), a fall from a high place, a bicycle fall, and a fall while climbing, by using the second module 412. According to an embodiment, after a fall occurs to the user, the processor 410 may identify that an impact has occurred to the user using the second module 412, and may identify (or determine) whether the user is conscious. According to an embodiment, after a fall occurs to the user, the processor 410 may bypass (or omit) identifying that an impact has occurred to the user, and may identify (or determine) whether the user is conscious. According to an embodiment, after a fall occurs to the user, the processor 410 may refrain from identifying that an impact has occurred to the user, and may identify (or determine) whether the processor is conscious of the user.

According to an embodiment, the processor 410 may activate one of the first module 411 and the second module 412 according to whether the user is sleeping. For example, the processor 410 may activate the first module 411 of the first module 411 and the second module 412 based on identifying that the user is sleeping. For example, the processor 410 may activate the second module 412 of the first module 411 and the second module 412 based on identifying that the user is awake.

Figure 6:
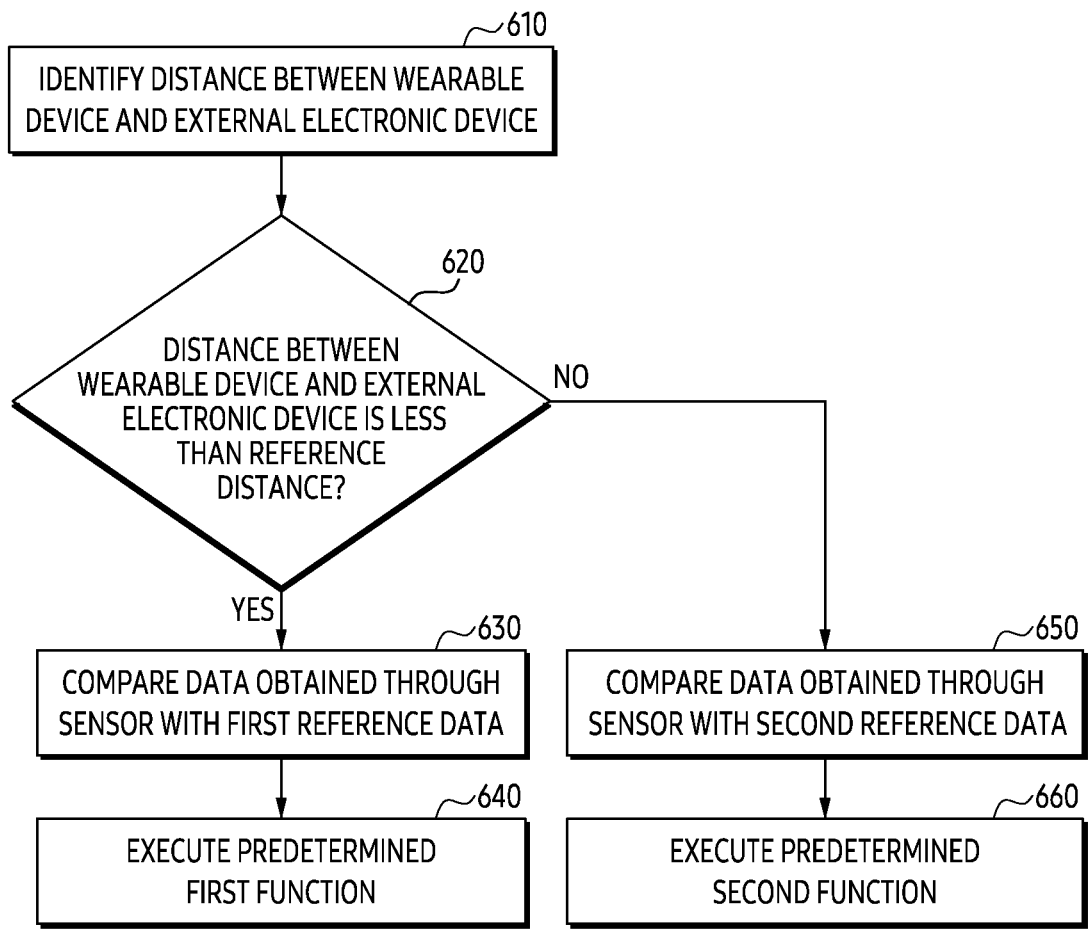
FIG. 6 is a flowchart illustrating an exemplary operation of a wearable device according to an example embodiment.

FIG. 6 is a flowchart illustrating an exemplary operation of a wearable device according to an embodiment.

In the following embodiment, each operation may be sequentially performed, but is not necessarily sequentially performed. For example, the order of each operation may be changed, and at least two operations may be performed in parallel.

According to an embodiment, operations 610 to 660 may be understood to be performed in a processor (e.g., the processor 410 of FIG. 4) of an electronic device (e.g., the electronic device 400 of FIG. 4).

Referring to FIG. 6, in operation 610, the processor 410 may identify a distance between the wearable device 400 and an external electronic device (e.g., the electronic device 102, the electronic device 104, and/or the server 108). For example, the processor 410 may identify the distance between the wearable device 400 and the external electronic device through the communication circuit 420 (e.g., the communication circuit 420 of FIG. 4) while identifying that the user wearing the wearable device 400 is sleeping.

According to an embodiment, the processor 410 may identify that a user wearing the wearable device 400 is sleeping. For example, the processor 410 may identify that the user is sleeping based on the information obtained using the sensor 430 (e.g., the sensor 430 of FIG. 4) within a designated time interval. For example, the processor 410 may identify that the user is sleeping based on information obtained using an acceleration sensor 431 (e.g., the acceleration sensor 431 in FIG. 4), a gyro sensor 432 (e.g., the gyro sensor 432 in FIG. 4), and/or a PPG sensor 433 (e.g., the PPG sensor 433 in FIG. 4). The processor 410 may identify that the user is sleeping based on identifying that a value indicating the user's movement obtained through at least one of the acceleration sensor 431 and/or the gyro sensor 432 is below the first threshold, and that the user's heart rate obtained through the PPG sensor 433 is below the threshold.

For example, the processor 410 may identify the location of the user wearing the wearable device 400 using the global positioning system (GPS) circuit of the wearable device 400. The processor 410 may identify that the user is lying in bed using at least one of the user's location, the user's posture, and/or the altitude of the wearable device 400. The processor 410 may obtain data using the sensor 430 (e.g., the acceleration sensor 431, the gyro sensor 432, and/or the PPG sensor 433) during the first sleep identification interval (e.g., about 30 minutes). The processor 410 may obtain data by monitoring the user using the sensor 430 during the first sleep identification interval (e.g., about 30 minutes). The processor 410 may identify that the user is sleeping based on the data obtained during the first sleep identification interval. For example, when the user wakes up briefly, the processor 410 may identify whether the user falls asleep again based on data obtained during the second sleep identification interval shorter than the first sleep identification interval.

According to an embodiment, the processor 410 may identify a user's sleep state using the PPG sensor 433 or an electrocardiogram sensor. For example, a sleep state may include a light sleep state, a deep sleep state, or a rapid eye movement sleep (REM) state (or REM sleep state).

According to an embodiment, the wearable device 400 may establish a connection with an external electronic device. For example, the wearable device 400 may operate in connection with an external electronic device. For example, the processor 410 of the wearable device 400 may control the external electronic device by transmitting a signal to the external electronic device. For example, the processor 410 may perform an operation based on a signal received from the external electronic device. For example, the wearable device 400 may be connected to an external electronic device in any communication method capable of a time difference of arrival (TDoA) method. For example, the communication method may include Bluetooth communication, Bluetooth low energy (BLE) communication, Wi-Fi communication, near field communication (NFC) communication and/or ultra-wideband (UWB) communication, but it is not limited thereto.

According to an embodiment, the processor 410 may identify a distance between the wearable device 400 and the external electronic device using the communication circuit 420. For example, the processor 410 may identify a distance between the wearable device 400 and the external electronic device using the UWB signal.

For example, the processor 410 may transmit a UWB signal to an external electronic device. The processor 410 may receive a reflection signal for a UWB signal caused by the external electronic device. The processor 410 may identify a moment in which the UWB signal is transmitted and a moment in which the reflection signal is received. The processor 410 may identify a distance between the wearable device 400 and the external electronic device based on the moment in which the UWB signal is transmitted and the moment in which the reflected signal is received.

For example, the processor 410 may transmit a UWB signal to the external electronic device. The processor 410 may receive another UWB signal (or response signal) for the UWB signal from the external electronic device. The processor 410 may identify a moment when a UWB signal is transmitted, a moment when another UWB signal is received, a moment when a UWB signal is received from the external electronic device, and a moment when another UWB signal is transmitted from the external electronic device. The processor 410 may identify a distance between the wearable device 400 and the external electronic device, based on the moment when a UWB signal is transmitted, the moment when another UWB signal is received, the moment when a UWB signal is received from an external electronic device, and the moment when another UWB signal is transmitted from an external electronic device.

According to an embodiment, the processor 410 may identify a user's movement using the sensor 430 (or at least one sensor). The processor 410 may identify a distance between the wearable device 400 and the external electronic device based on identifying the user's movement. For example, the processor 410 may identify a movement of a sleeping user. The processor 410 may identify the distance between the wearable device 400 and the external electronic device to identify whether the user is sleeping based on identifying the user's movement.

For example, the processor 410 may identify a plurality of steps of the user. The processor 410 may identify that the number of the plurality of steps of the user is greater than or equal to the threshold number of steps. The processor 410 may identify the movement of the user based on identifying that the number of the plurality of steps of the user is greater than or equal to the threshold number of steps. The processor 410 may identify a distance between the wearable device 400 and the external electronic device based on identifying that the number of the plurality of steps of the user is greater than or equal to the threshold number of steps.

According to an embodiment, a plurality of steps may be identified through the wearable device 400 by a user's movement on the bed. The processor 410 may identify the distance between the wearable device 400 and the external electronic device to identify the user moving after waking up. For example, the processor 410 may identify the distance between the wearable device 400 and the external electronic device to identify that the user has left the bed after waking up.

In operation 620, the processor 410 may identify whether the distance between the wearable device 400 and the external electronic device is less than the reference distance. For example, the processor 410 may identify whether the distance between the wearable device 400 and the external electronic device is less than the reference distance to identify whether the user is sleeping.

According to an embodiment, when the user is sleeping, the external electronic device may be located in a fixed position. For example, an external electronic device may be located in a bedside space and located in a fixed position while the user is sleeping. For example, the external electronic device may be located in a fixed position around the user while the user is sleeping. For example, the processor 410 may identify whether the distance between the external electronic device located in a fixed position while the user is sleeping and the wearable device 400 worn to the user is less than the reference distance.

In operation 630, when the distance between the wearable device 400 and the external electronic device is less than the reference distance, the processor 410 may compare the data obtained through the sensor 430 with the first reference data. For example, the processor 410 may compare the data obtained through the sensor 430 (or at least one sensor) with first reference data for identifying the first state of the user while the user is sleeping, based at least in a part identifying the distance between wearable device 400 and the external electronic device that is less than the reference distance.

According to an embodiment, the processor 410 may identify that the distance between the wearable device 400 and the external electronic device is less than the reference distance. The processor 410 may identify that the user maintains a sleeping state based on identifying that the distance between wearable device 400 and the external electronic device is less than the reference distance.

According to an embodiment, the processor 410 may obtain data (e.g., biometric data of a user or data about a user) through the sensor 430. For example, the processor 410 may obtain data through the sensor 430 while the user is sleeping. For example, the processor 410 may obtain data through the sensor 430 to identify whether the user is in the first state. The first state may include a state in which the user falls while sleeping.

For example, the processor 410 may obtain data through the acceleration sensor 431, the gyro sensor 432, the barometric pressure sensor 434, and/or the PPG sensor 433 while the user is sleeping. The processor 410 may obtain data through the acceleration sensor 431, the gyro sensor 432, the barometric pressure sensor 434, and/or the PPG sensor 433 to identify whether the user is in a first state (e.g., a state that the user falls while sleeping).

According to an embodiment, the processor 410 may activate the first module 411 of the first module 411 (e.g., the first module 411 of FIG. 5) and the second module 412 (e.g., the second module 412 of FIG. 5) for identifying the fall, based at least in part on identifying that the distance between wearable device 400 and the external electronic device is less than the reference distance. The processor 410 may compare the data obtained through the sensor 430 with first reference data for identifying the first state of the user while the user is sleeping, by activating the first module 411. For example, the processor 410 may identify whether the user is in the first state using the first model 501 (e.g., the first model 501 of FIG. 5). The processor 410 may identify whether a fall occurs to the user while the user is sleeping by comparing the data obtained through the sensor 430 with the first reference data using the first model 501 indicated by a plurality of first parameters.

For example, the first reference data may be used to identify the first state of the user. The processor 410 may identify that the user is in the first state based on identifying that the data obtained through the sensor 430 corresponds to the first reference data.

For example, the processor 410 may detect acceleration greater than or equal to a predefined first magnitude using the acceleration sensor 431. The processor 410 may identify a change in air pressure using the barometric pressure sensor 434 at a time interval including a moment in which acceleration greater than or equal to a predefined first magnitude is detected. The processor 410 may identify that the user is in a first state based on identifying that the air pressure change rate and the change amount of air pressure satisfy a predefined first condition. The processor 410 may identify that a fall has occurred to the user during sleep, based on identifying that the air pressure change rate and the change amount of air pressure satisfy a predefined first condition.

An operation of identifying whether a fall occurs to the user while the user is sleeping by comparing the data obtained using the sensor 430 with the first reference data will be described later in FIGS. 8A to 8D.

In operation 640, the processor 410 may identify/execute a predetermined first function. For example, the processor 410 may execute the predetermined first function according to a comparison between the data obtained through the sensor 430 and the first reference data.

According to an embodiment, the processor 410 may execute the predetermined first function, which is a function for notifying that the user is an emergency situation, according to a comparison between data obtained through the sensor 430 and the first reference data. For example, the processor 410 may execute the predetermined first function to notify the user that a fall has occurred while the user is sleeping according to the comparison between the data obtained through the sensor 430 and the first reference data.

For example, the processor 410 may transmit a signal for notifying a predetermined user that the user is in an emergency situation using an external electronic device. The processor 410 may transmit a signal for calling a designated contact (e.g., an SOS call or an emergency contact) to an external electronic device.

According to an embodiment, the processor 410 may provide a first notification to indicate that a fall has occurred to the user while the user is sleeping according to a comparison between the data obtained through the sensor 430 and the first reference data. For example, the first notification may be displayed through a display (e.g., the display module 160 of FIG. 1) of the wearable device 400. For example, the first notification may be output through a speaker (e.g., the sound output module 155 of FIG. 1) of the wearable device 400.

According to an embodiment, the processor 410 may identify that the sleeping user has fallen based on comparing the data obtained through the sensor 430 with the first reference data. In response to identifying that the sleeping user has fallen, the processor 410 may identify the magnitude of the impact applied to the user. The processor 410 may identify the magnitude of the impact applied to the user by using sensor 430 (e.g., the acceleration sensor 431, the PPG sensor 433, and/or the barometric pressure sensor 434).

For example, the processor 410 may execute a predetermined first function in response to identifying that the magnitude of the impact applied to the user is greater than or equal to the reference magnitude. The processor 410 may execute a predetermined first function, which is a function for notifying that the user is in an emergency situation, in response to identifying that the magnitude of the impact applied to the user is greater than or equal to the reference magnitude.

According to an embodiment, the processor 410 may identify whether the user has lost consciousness in response to identifying that the magnitude of the impact applied to the user is less than the reference magnitude. For example, the processor 410 may identify a user's movement using the acceleration sensor 431, the gyro sensor 432, and/or the barometric pressure sensor 434. The processor 410 may identify that the user has lost consciousness based on not identifying the user's movement for a designated time and/or that the change in altitude or air pressure is less than or equal to a certain magnitude.

The processor 410 may execute a predetermined first function in response to identifying that the user has lost consciousness. The processor 410 may execute a predetermined first function, which is a function for notifying that the user is in an emergency situation, in response to identifying that the user has lost consciousness, even when the magnitude of the impact applied to the user is less than the reference magnitude.

In operation 650, when the distance between the wearable device 400 and the external electronic device is greater than or equal to the reference distance, the processor 410 may compare the data obtained through the sensor 430 (or at least one sensor) with the second reference data. For example, the processor 410 may compare the data obtained through sensor 430 (or at least one sensor) with second reference data for identifying the second state of the user while the user is awake, based at least in part on identifying the distance between wearable device 400 and the external electronic device that is greater than or equal to the reference distance.

According to an embodiment, the processor 410 may identify that the distance between the wearable device 400 and the external electronic device is greater than or equal to a reference distance. The processor 410 may identify that the user is awake based on identifying that the distance between the wearable device 400 and the external electronic device is greater than or equal to the reference distance.

According to an embodiment, the processor 410 may obtain data through the sensor 430. For example, the processor 410 may obtain data through the sensor 430 while the user is awake. For example, the processor 410 may obtain data through the sensor 430 to identify whether the user is in the second state. The second state may include a state in which the user falls while the user is awake.

For example, the processor 410 may obtain data through the acceleration sensor 431 while the user is awake. The processor 410 may obtain data through the acceleration sensor 431 to identify whether the user is in a second state (e.g., a state in which the user falls while awake).

According to an embodiment, the processor 410 may activate a second module 412 of the first module 411 and the second module 412 for identifying a fall, based at least in part on identifying the distance between wearable device 400 and the external electronic device that is greater than or equal to the reference distance. The processor 410 may compare the data obtained through the sensor 430 with second reference data for identifying the second state of the user while the user is awake, by activating the second module 412. For example, the processor 410 may identify whether the user is in the second state using the second model 502 (e.g., the second model 502 of FIG. 5). The processor 410 may identify whether a fall occurs to the user while the user is awake, by comparing the data obtained through the sensor 430 with the second reference data using the second model 502 indicated by a plurality of second parameters.

For example, the second reference data may be used to identify the second state of the user. The processor 410 may identify that the user is in the second state based on identifying that the data obtained through the sensor 430 corresponds to the second reference data.

For example, the processor 410 may detect acceleration greater than or equal to a predefined second magnitude using the acceleration sensor 431. The processor 410 may identify a change in air pressure using the barometric pressure sensor 434 at a time interval including a moment in which acceleration greater than or equal to a predefined second magnitude is detected. The processor 410 may identify that the user is in a second state based on identifying that the air pressure change rate and the change amount of air pressure satisfy a predefined second condition. The processor 410 may identify that a fall has occurred while the user is awake based on identifying that the air pressure change rate and the change amount of air pressure satisfy a predefined second condition.

An operation of identifying whether a fall occurs to the user while the user is awake by comparing the data obtained using the sensor 430 with the second reference data will be described later in FIGS. 9A to 9D.

In operation 660, the processor 410 may identify/execute a predetermined second function. For example, the processor 410 may execute a predetermined second function according to a comparison between the data obtained through the sensor 430 and the second reference data.

According to an embodiment, the processor 410 may execute a predetermined second function, which is a function for notifying that the user is an emergency situation, according to a comparison between data obtained through the sensor 430 and the second reference data. For example, the processor 410 may execute a predetermined second function to notify that a fall has occurred to the user while the user is awake according to the comparison between the data obtained through the sensor 430 and the second reference data.

According to an embodiment, the processor 410 may identify the type of fall that occurs to the user using the second module 412. For example, the processor 410 may identify a type of fall that occurs to the user as at least one of a fall while walking, a fall while running, a fall on a slope (e.g., ramp or stairs), a fall from a high place, a bicycle fall, and a fall while climbing, by using the second module 412.

The processor 410 may execute a predetermined second function to notify that the fall has occurred based on the type of fall that has occurred to the user. For example, the processor 410 may identify that the user has fallen while climbing. The processor 410 may notify that a fall has occurred by transmitting a rescue signal including the user's location information and the user's state.

According to an embodiment, the processor 410 may provide a second notification to indicate that a fall has occurred to the user while the user is awake according to a comparison between the data obtained through the sensor 430 and the second reference data. For example, the second notification may be displayed through the display of the wearable device 400. For example, the second notification may be output through a speaker of the wearable device 400.

According to an embodiment, the processor 410 may identify that the awake user has fallen based on comparing the data obtained through the sensor 430 with the second reference data. In response to identifying that the awake user has fallen, the processor 410 may identify the magnitude of the impact applied to the user. The processor 410 may identify the magnitude of the impact applied to the user using sensor 430 (e.g., the acceleration sensor 431, the PPG sensor 433, and/or the barometric pressure sensor 434).

For example, the processor 410 may execute a predetermined second function in response to identifying that the magnitude of the impact applied to the user is greater than or equal to the reference magnitude. The processor 410 may execute a predetermined second function, which is a function for notifying that the user is in an emergency situation, in response to identifying that the magnitude of the impact applied to the user is greater than or equal to the reference magnitude.

For example, the processor 410 may identify whether the user has lost consciousness in response to identifying that the magnitude of the impact applied to the user is less than the reference magnitude. The processor 410 may identify the movement of the user using the acceleration sensor 431, the gyro sensor 432, and/or the barometric pressure sensor 434. The processor 410 may identify that the user has lost consciousness based on not identifying the user's movement for a designated time or that the change in altitude or air pressure is less than or equal to a certain size.

The processor 410 may execute a predetermined second function in response to identifying that the user has lost consciousness. The processor 410 may execute a predetermined second function, which is a function for notifying that the user is in an emergency, in response to identifying that the user has lost consciousness, even when the magnitude of the impact applied to the user is less than the reference magnitude.

Figure 7:
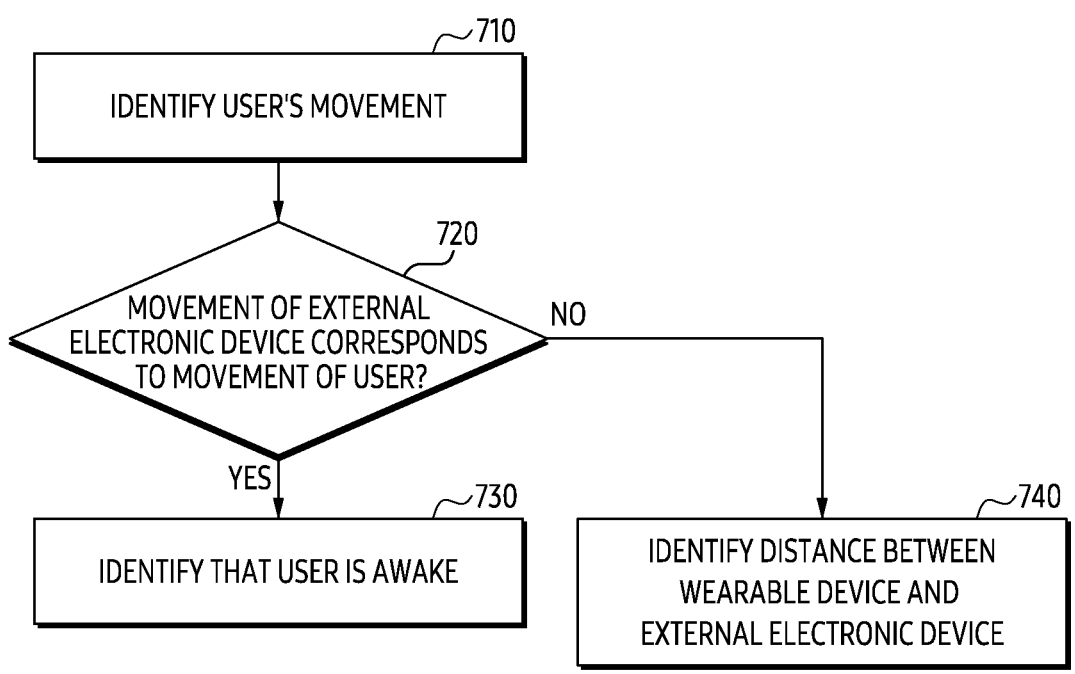
FIG. 7 is a flowchart illustrating an exemplary operation of a wearable device according to an example embodiment.

FIG. 7 is a flowchart illustrating an exemplary operation of a wearable device according to an embodiment.

In the following embodiment, each operation may be sequentially performed, but is not necessarily sequentially performed. For example, the order of each operation may be changed, and at least two operations may be performed in parallel.

According to an embodiment, operations 710 to 740 may be understood to be performed in a processor (e.g., the processor 410 of FIG. 4) of an electronic device (e.g., the electronic device 400 of FIG. 4).

Referring to FIG. 7, operations 710 to 740 may be related to operation 610 of FIG. 6.

In operation 710, the processor 410 may identify a user's movement. For example, the processor 410 may identify the movement of the user using the sensor 430 (e.g., the sensor 430 of FIG. 4) (or at least one sensor). For example, the processor 410 may identify a movement of a user wearing the wearable device 400. For example, the processor 410 may identify the movement of the user wearing the wearable device 400 using the acceleration sensor 431 (e.g., the acceleration sensor 431 in FIG. 4 and/or the gyro sensor 432 in FIG. 4).

In operation 720, the processor 410 may identify whether the movement of the external electronic device corresponds to the movement of the user. For example, processor 410 may identify whether the movement of the external electronic device corresponds to the movement of the user based on identifying the movement of the user.

According to an embodiment, the external electronic device (or a processor of the external electronic device) may identify the movement of the external electronic device. The external electronic device may transmit information on the movement of the external electronic device to the wearable device 400. The processor 410 may receive information on the movement of the external electronic device from the external electronic device. The processor 410 may identify whether the movement of the external electronic device corresponds to the movement of the user based on information on the movement of the external electronic device.

In operation 730, when the movement of the external electronic device corresponds to the movement of the user, the processor 410 may identify that the user is awake. For example, the processor 410 may identify that the user is awake based on identifying that the movement of the external electronic device corresponds to the movement of the user.

According to an embodiment, the processor 410 may identify that the user is moving with the external electronic device based on identifying that the movement of the external electronic device corresponds to the movement of the user. For example, the processor 410 may identify that the user is moving while carrying an external electronic device.

For example, the processor 410 may identify that the user is moving using the wearable device 400. The processor 410 may identify that the speed and direction at which the external electronic device is moved correspond to the speed and direction at which the wearable device 400 is moved. The processor 410 may identify that the movement of the external electronic device corresponds to the movement of the user, based on identifying that the speed and direction at which the external electronic device is moved corresponds to the speed and direction at which the wearable device 400 is moved.

According to an embodiment, the processor 410 may identify that the user is awake based on identifying that the user is moving with an external electronic device. The processor 410 may identify the second state of the user based on identifying that the user is awake. For example, the processor 410 may identify whether a fall has occurred to an awake user.

In operation 740, when the movement of the external electronic device does not correspond to the movement of the user, the processor 410 may identify a distance between the wearable device 400 and the external electronic device. The processor 410 may identify a distance between the wearable device 400 and the external electronic device based on identifying that the movement of the external electronic device does not correspond to the user's movement. For example, the processor 410 may perform operation 610 of FIG. 6 based on identifying that the movement of the external electronic device does not correspond to the movement of the user.

According to operations 710 to 740, the processor 410 may identify the movement of the user identified as sleeping. The processor 410 may identify that the user is awake based on the movement of the external electronic device corresponding to the movement of the user. The processor 410 may identify the second state of the user while awake. The processor 410 may identify whether the user is awake based on the distance between the external electronic device and the wearable device 400 based on that the movement of the external electronic device does not correspond to the movement of the user.

Figure 8A:
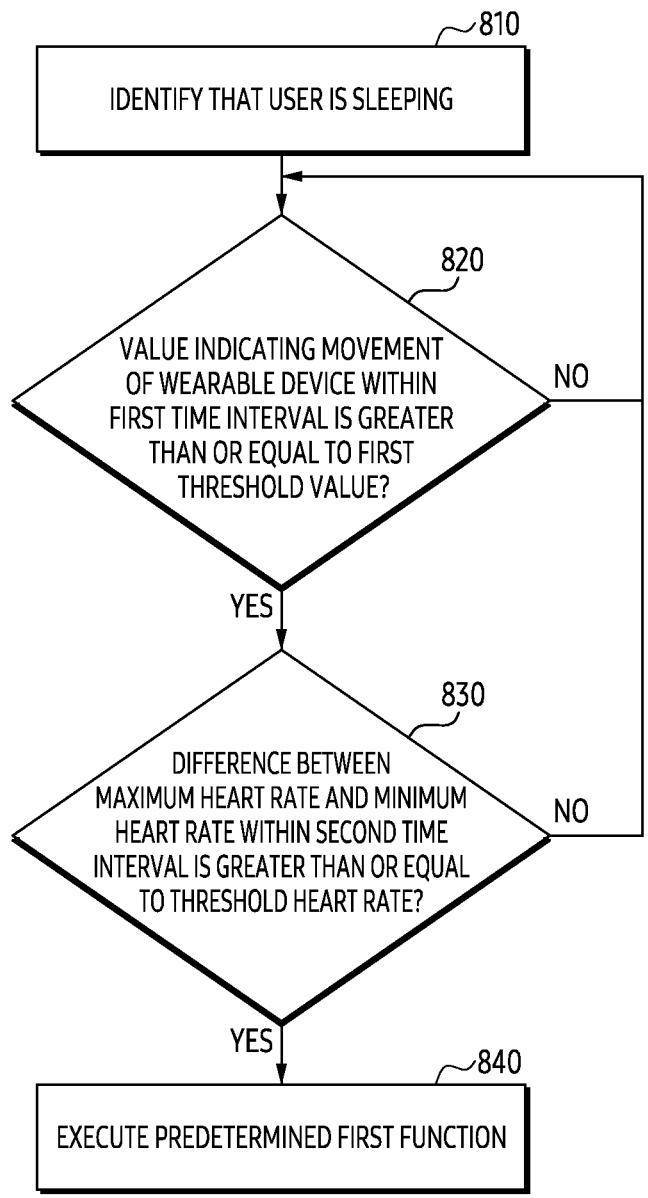
FIG. 8A is a flowchart illustrating an exemplary operation of a wearable device according to an example embodiment.

FIG. 8A is a flowchart illustrating an exemplary operation of a wearable device according to an embodiment.

Figure 8B:
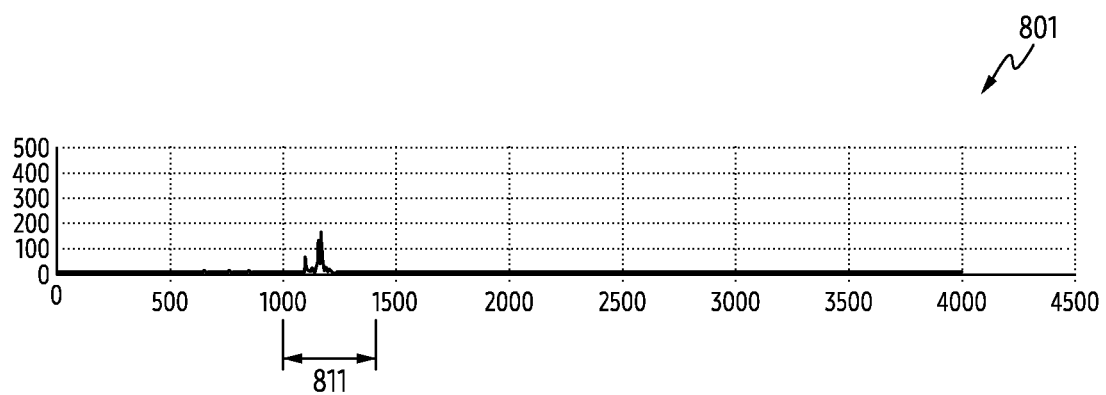
FIG. 8B is an example of a graph representing a change in acceleration over time identified in a wearable device according to an example embodiment.

FIG. 8B is an example of a graph representing a change in acceleration over time identified in a wearable device according to an embodiment.

Figure 8C:
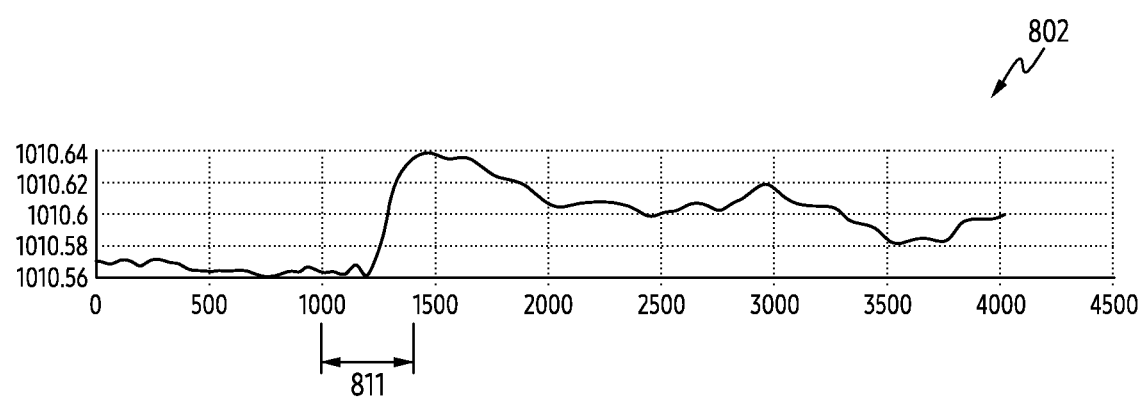
FIG. 8C is an example of a graph representing a change in air pressure over time identified in a wearable device according to an example embodiment.

FIG. 8C is an example of a graph representing a change in air pressure over time identified in a wearable device according to an embodiment.

Figure 8D:
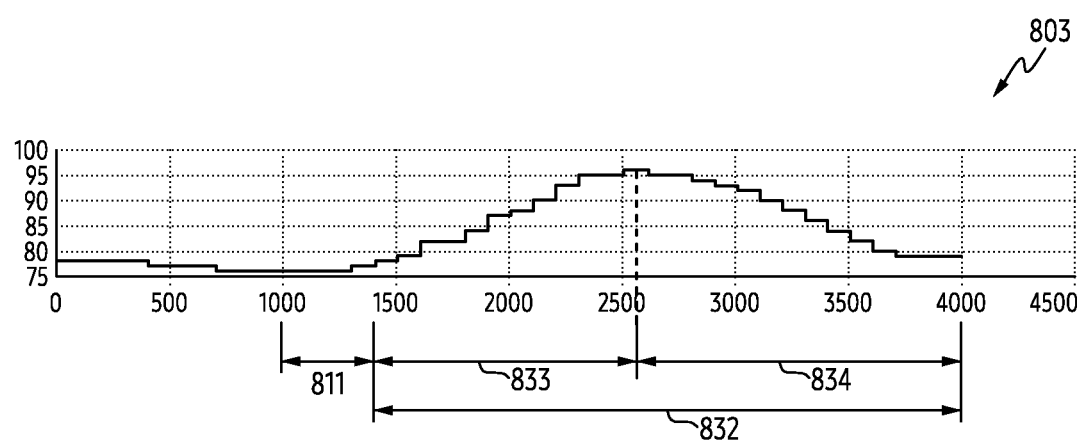
FIG. 8D is an example of a graph representing a change in heart rate over time identified in a wearable device according to an example embodiment.

FIG. 8D is an example of a graph representing a change in heart rate over time identified in a wearable device according to an embodiment.

In the following embodiment, each operation may be sequentially performed, but is not necessarily sequentially performed. For example, the order of each operation may be changed, and at least two operations may be performed in parallel.

According to an embodiment, operations 810 to 840 may be understood to be performed in a processor (e.g., the processor 410 of FIG. 4) of an electronic device (e.g., the electronic device 400 of FIG. 4).

Referring to FIG. 8A, in operation 810, the processor 410 (e.g., the processor 410 of FIG. 4) may identify that the user is sleeping. For example, the processor 410 may identify that the user is sleeping based on identifying that the distance between wearable device 400 and the external electronic device is less than the reference distance.

In operation 820, the processor 410 may identify whether a value indicating the movement of the wearable device 400 within the first time interval is greater than or equal to a first threshold value. In order to identify whether the user is in the first state, the processor 410 may identify whether a value indicating the movement of the wearable device 400 within the first time interval is greater than or equal to a first threshold value. For example, the processor 410 may identify whether the value indicating the movement of the wearable device 400 within the first time interval is greater than or equal to the first threshold value in order to identify whether a fall has occurred to the user.

For example, the value indicating the movement of the wearable device 400 may be the magnitude of the acceleration of the wearable device 400. The processor 410 may obtain (or identify) a value indicating the movement of the wearable device 400 (or the magnitude of the acceleration of the wearable device 400) using the acceleration sensor 431 (e.g., the acceleration sensor 431 of FIG. 4). The processor 410 may identify whether a value (or the magnitude of the acceleration of the wearable device 400) indicating the movement of the wearable device 400 obtained using the acceleration sensor 431 is greater than or equal to a first threshold value.

According to an embodiment, the processor 410 may monitor the movement of the wearable device 400 when the value indicating the movement of the wearable device 400 within the first time interval is not greater than or equal to the first threshold value.

According to an embodiment, when a value indicating a movement of the wearable device 400 within the first time interval is greater than or equal to a first threshold value, the processor 410 may identify that the user is in the first state. The processor 410 may identify that the user is in the first state based on that the value indicating the movement of the wearable device 400 within the first time interval is greater than or equal to the first threshold value. For example, the processor 410 may identify that a fall has occurred to the user while the user was sleeping, based on the value indicating the movement of the wearable device 400 within the first time interval being equal to or greater than the first threshold.

Referring to FIG. 8B, a graph 801 shows a change in the magnitude of acceleration over time of the wearable device 400. The x-axis of the graph 801 represents time. The unit of the x-axis is [ms(millisecond)]. The y-axis of the graph 801 represents the magnitude of acceleration. The unit of the y-axis is [m/s2 (meter per second squared)]. The processor 410 may identify acceleration of the wearable device 400 in three directions of the x-axis, the y-axis, and the z-axis using the acceleration sensor 431. The processor 410 may perform vector addition based on vectors representing accelerations in three directions of the x-axis, the y-axis, and the z-axis. The processor 410 may identify the magnitude of the resultant vector identified according to the vector addition as the magnitude of the acceleration of the wearable device 400.

For example, within the first time interval 811, the processor 410 may identify that the magnitude of the acceleration identified using the acceleration sensor 431 is greater than or equal to the first threshold value (e.g., 100 m/s2). The processor 410 may identify that the user is in the first state based on identifying that the magnitude of the acceleration identified using the acceleration sensor 431 within the first time interval 811 is greater than or equal to the first threshold value. The processor 410 may identify that a fall has occurred to the user while the user is sleeping, based on identifying that the magnitude of the acceleration identified using the acceleration sensor 431 within the first time interval 811.

Referring to FIG. 8A, the processor 410 may identify a change in air pressure within a first time interval to identify that the user is in a first state. For example, the processor 410 may identify a change in position from the ground of the wearable device 400 based on the change in air pressure within the first time interval.

For example, the processor 410 may identify that the user is in a first state based on that the maximum change in air pressure within the first time interval is greater than or equal to the first reference change. The processor 410 may identify the minimum air pressure and the maximum air pressure within the first time interval. The processor 410 may identify the maximum amount of change in the air pressure based on the minimum air pressure and the maximum air pressure within the first time interval.

For example, the processor 410 may identify that the user is in a first state based on that the air pressure change rate is greater than or equal to the first reference change rate within the first time interval. The processor 410 may identify a gradient of air pressure within the first time interval. The processor 410 may identify the gradient of air pressure by identifying the gradient of air pressure within the first time interval. For example, the processor 410 may identify the gradient of air pressure by differentiating the air pressure value with respect to time, identified within the first time interval. The processor 410 may identify the air pressure change rate based on the identified air pressure change rate.

Referring to FIG. 8C, a graph 802 represents a change in air pressure of the wearable device 400 over time. The x-axis of the graph 802 represents time. The unit of the x-axis is [ms(millisecond)]. The y-axis of the graph 802 represents the magnitude of the air pressure. The unit of the y-axis is [hPa(hectopascal)].

For example, the processor 410 may identify the maximum amount of change in air pressure within the first time interval 811. The processor 410 may identify that a fall has occurred to the user based on that the maximum amount of change in air pressure within the first time interval 811 is greater than or equal to the first reference change amount (e.g., 0.06 hPa). The processor 410 may identify the height (e.g., about 70 cm) at which the user falls based on the maximum amount of change in air pressure. The processor 410 may identify a distance between a position where the user is lying on the bed and the ground based on the height at which the user has fallen.

For example, the processor 410 may identify a gradient of air pressure within the first time interval 811. The processor 410 may identify that a fall has occurred to the user while the user is sleeping based on that the air pressure change rate within the first time interval 811 is greater than or equal to the first reference change rate.

Referring to FIG. 8A, the processor 410 may identify that the user is in the first state based on at least one of whether the value indicating the movement of the wearable device 400 within the first time interval is greater than or equal to the first threshold value, whether the maximum amount of change in air pressure within the first time interval is greater than or equal to the first reference amount of change, or whether the gradient of air pressure within the first time interval is greater than or equal to the first reference rate of change.

For example, the processor 410 may identify that the user is in the first state based on identifying that the value indicating the movement of the wearable device 400 within the first time interval is greater than or equal to the first threshold value, the maximum amount of change in air pressure within the first time interval is greater than or equal to the first reference amount of change, or the gradient of air pressure within the first time interval is greater than or equal to the first reference rate of change. For example, the processor 410 may identify that a fall has occurred to the user while the user is sleeping, based on identifying that the value representing the movement of the wearable device 400 within the first time interval is greater than or equal to the first threshold value, the maximum amount of change in air pressure within the first time interval is greater than or equal to the first reference amount of change, or the gradient of air pressure within the first time interval is greater than or equal to the first reference rate of change.

In operation 830, when a value indicating a movement of the wearable device 400 within the first time interval is greater than or equal to a first threshold value, the processor 410 may identify whether the difference between the maximum heart rate and the minimum heart rate within the second time interval is greater than or equal to the threshold heart rate. For example, the processor 410 may identify whether the difference between the maximum heart rate and the minimum heart rate within the second time interval is greater than or equal to the threshold heart rate, based on that the value indicating the movement of the wearable device 400 within the first time interval is greater than or equal to the first threshold value. For example, the processor 410 may identify whether the difference between the maximum heart rate and the minimum heart rate within the second time interval is greater than or equal to the threshold heart rate to identify whether the magnitude of the impact applied to the user is greater than or equal to the reference magnitude.

Unlike when a fall occurs while the user is awake, when a fall occurs while sleeping, the user is often unable to reduce the impact to the body by stretching a hand. Therefore, when a fall occurs during sleep, a large impact occurs on the user's body, and accordingly, the heart rate may increase after the fall occurs and then decrease again. The processor 410 may identify that the magnitude of the impact applied to the user is greater than or equal to the reference magnitude based on identifying that the heart rate increases after the fall occurs and then decreases again.

According to an embodiment, after identifying that the value indicating the movement of the wearable device 400 within the first time interval is greater than or equal to the first threshold value, the processor 410 may identify that the difference between the maximum heart rate and the minimum heart rate within the second time interval after the first time interval is greater than or equal to the threshold heart rate, based on data on the user's heart rate identified using the PPG sensor 433 (e.g., the PPG sensor 433 of FIG. 4).

For example, the processor 410 may identify data on the user's heart rate within the second time interval after the first time interval in which the user falls. The processor 410 may identify that the difference between the maximum heart rate and the minimum heart rate within the second time interval is greater than or equal to the threshold heart rate. Based on that the difference between the maximum heart rate and the minimum heart rate within the second time interval is greater than or equal to the threshold heart rate, it may be identified that the user's heart rate increase rate is greater than or equal to the reference increase rate. The processor 410 may identify that the magnitude of the impact applied to the user is greater than or equal to the reference magnitude, based on the user's heart rate increase rate is greater than or equal to the reference increase rate. For example, the threshold heart rate and the reference increase rate may be changed based on the user's age and/or the user's physical activity ability. For example, the processor 410 may identify the representative heart rate of the user before the second time interval. For example, the representative heart rate may be set to one of a maximum heart rate, a minimum heart rate, an intermediate heart rate, and a most frequent heart rate, or an average heart rate. The threshold heart rate and the reference increase rate may be changed based on the representative heart rate of the user.

According to an embodiment, the processor 410 may identify that the value indicating the movement of the user within the first time interval is greater than or equal to the first threshold value and that the value indicating the movement of the user within the second time interval is less than or equal to the reference value. The processor 410 may identify that a value indicating the movement of the user within the second time interval is less than or equal to a reference value (e.g., a first threshold value) in order to identify that the movement of the user does not occur after the fall occurs. For example, the processor 410 may identify that the difference between the maximum heart rate and the minimum heart rate within the second time interval is greater than or equal to the threshold heart rate, based on identifying that the value indicating the user's movement within the second time interval is less than or equal to the reference value.

According to an embodiment, the processor 410 may identify a heart rate within the second time interval to identify that the magnitude of the impact applied to the user is greater than or equal to the reference magnitude.

For example, the processor 410 may identify that the magnitude of the impact applied to the user is greater than or equal to the reference magnitude based on identifying that the heart rate increase rate within the second time interval is greater than or equal to the reference rate.

For example, the processor 410 may identify a maximum heart rate and a minimum heart rate within the second time interval. According to an embodiment, the processor 410 may identify a difference between the maximum heart rate and the minimum heart rate within the second time interval as a heart rate increase rate. The processor 410 may identify that the heart rate increase rate within the second time interval is greater than or equal to the reference rate, by identifying that the difference between the maximum heart rate and minimum heart rate is greater than or equal to the threshold heart rate.

For example, the processor 410 may identify a maximum heart rate within the second time interval and a representative heart rate before the second time interval. According to an embodiment, the processor 410 may identify a difference between the maximum heart rate and the representative heart rate as a heart rate increase rate. The processor 410 may identify that the heart rate increase rate within the second time interval is greater than or equal to the reference rate, by identifying that the difference between the maximum heart rate and the representative heart rate is greater than or equal to the threshold heart rate.

For example, the processor 410 may identify that the magnitude of the impact applied to the user is greater than or equal to the reference magnitude, based on identifying that the gradient of the heart rate within the second time interval is greater than or equal to the reference gradient. For example, the processor 410 may identify that the gradient of the heart rate within the second time interval is maintained above the reference gradient. The gradient of the heart rate may increase rapidly according to the wearing state of the user's wearable device 400 and/or an error of the PPG sensor 433. Accordingly, the processor 410 may identify that the magnitude of the impact applied to the user is greater than or equal to the reference magnitude by identifying that the gradient of the heart rate within the second time interval is maintained above the reference gradient.

Referring to FIG. 8D, a graph 803 represents a change in the heart rate of a user over time. The x-axis of the graph 803 represents time. The unit of the x-axis is [ms(millisecond)]. The y-axis of the graph 803 represents a heart rate. The unit of the y-axis is [bpm(beats per minute)].

For example, the processor 410 may identify that the magnitude of the impact applied to the user is greater than or equal to the reference magnitude based on identifying that the rate of increase in the heart rate within the second time interval 832 after the first time interval 811 is greater than or equal to the reference rate of increase. The processor 410 may identify a maximum heart rate (e.g., about 96) and a minimum heart rate (e.g., about 78) within the second time interval 832. The processor 410 may identify that the difference between the maximum heart rate and the minimum heart rate is greater than or equal to the threshold heart rate (e.g., 15). The processor 410 may identify that the heart rate increase rate within the second time interval 832 is greater than or equal to the reference rate by identifying that the difference between the maximum and minimum heart rates is greater than or equal to the threshold heart rate. The processor 410 may identify that the magnitude of the impact applied to the user is greater than or equal to the reference magnitude based on identifying that the heart rate increase rate within the second time interval 832 is greater than or equal to the reference increase rate.

For example, the processor 410 may identify that the heart rate increases and then decreases within the second time interval 832 after the first time interval 811. The second time interval 832 may include a heart rate increase interval 833 and a heart rate decrease interval 834. The processor 410 may identify that the gradient of the heart rate is maintained above the reference gradient in the heart rate increase interval 833 included in the second time interval 832. The processor 410 may identify that the magnitude of the impact applied to the user is greater than or equal to the reference magnitude, based on identifying that the gradient of the heart rate remains above the reference gradient at the heart rate increase interval 833.

Referring to FIG. 8A, the processor 410 may identify that the magnitude of the impact applied to the user is greater than or equal to the reference magnitude, based on at least one of whether the heart rate increase rate within the second time interval is above the reference rate and whether the gradient of the heart rate within the second time interval is above the reference gradient.

For example, the processor 410 may identify that the magnitude of the impact applied to the user is greater than or equal to the reference magnitude, based on that the heart rate increase rate within the second time interval is above the reference rate, and the gradient of the heart rate within the second time interval is above the reference gradient.

In operation 840, when the difference between the maximum heart rate and the minimum heart rate within the second time interval is greater than or equal to the threshold heart rate, the processor 410 may execute a predetermined first function. For example, the processor 410 may execute the predetermined first function based on identifying that the difference between the maximum heart rate and the minimum heart rate within the second time interval is greater than or equal to the threshold heart rate. For example, the processor 410 may execute the predetermined first function to notify that a fall has occurred to the user while the user is sleeping. Operation 840 may correspond to operation 640 of FIG. 6.

Figure 9A:
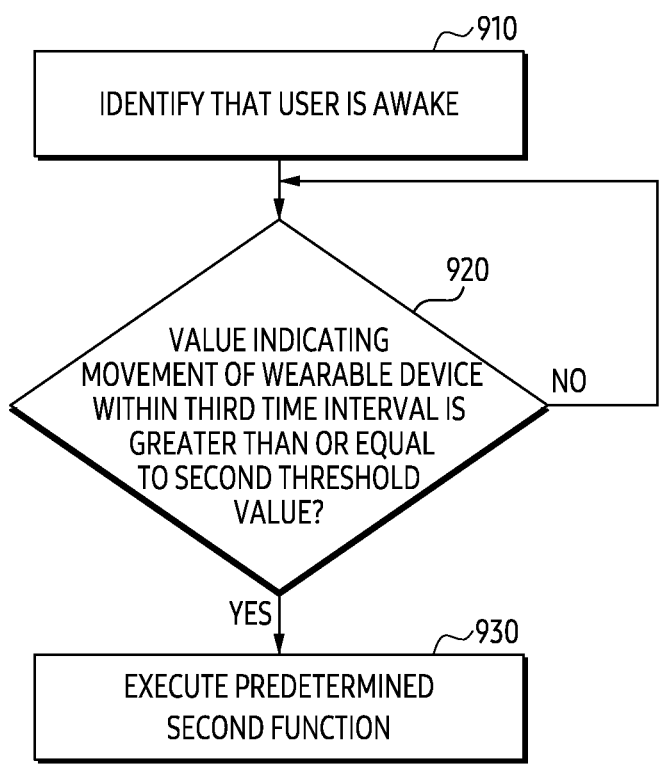
FIG. 9A is a flowchart illustrating an exemplary operation of a wearable device according to an example embodiment.

FIG. 9A is a flowchart illustrating an exemplary operation of a wearable device according to an embodiment.

Figure 9B:
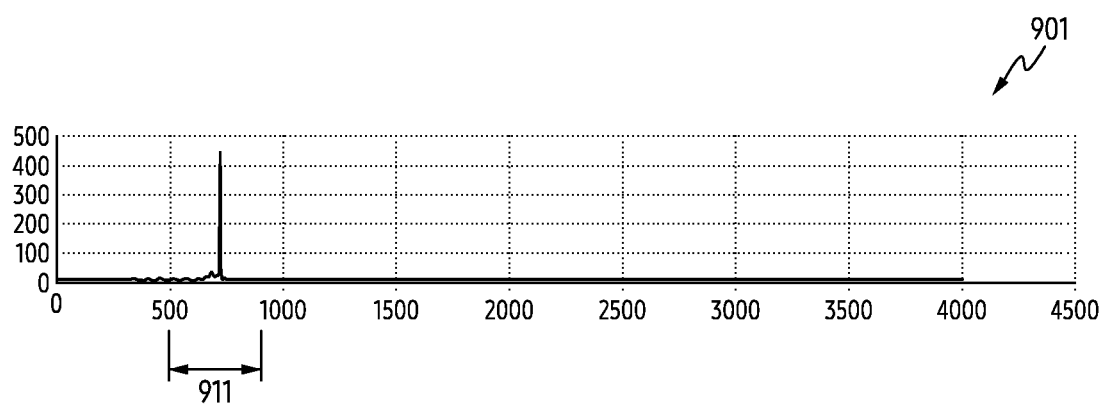
FIG. 9B is an example of a graph representing a change in acceleration over time identified in a wearable device according to an example embodiment.

FIG. 9B is an example of a graph representing a change in acceleration over time identified in a wearable device according to an embodiment.

Figure 9C:
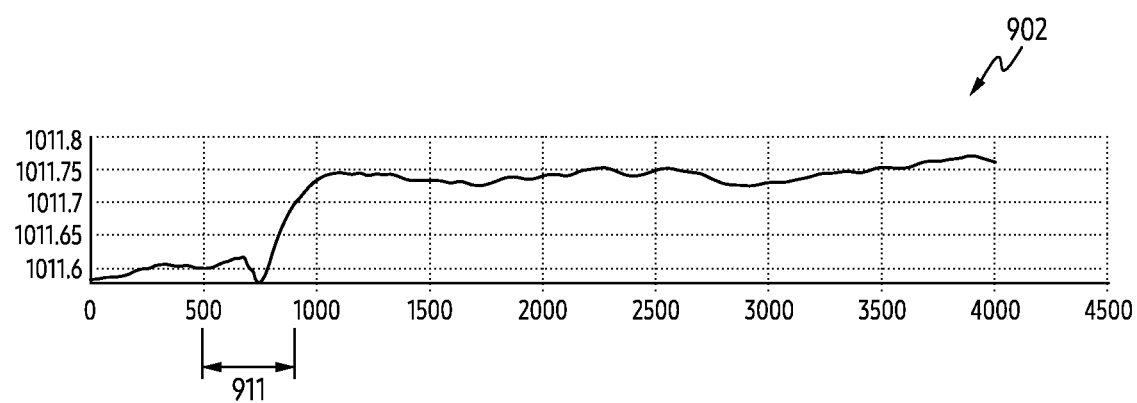
FIG. 9C is an example of a graph representing a change in air pressure over time identified in a wearable device according to an example embodiment.

FIG. 9C is an example of a graph representing a change in air pressure over time identified in a wearable device according to an embodiment.

Figure 9D:
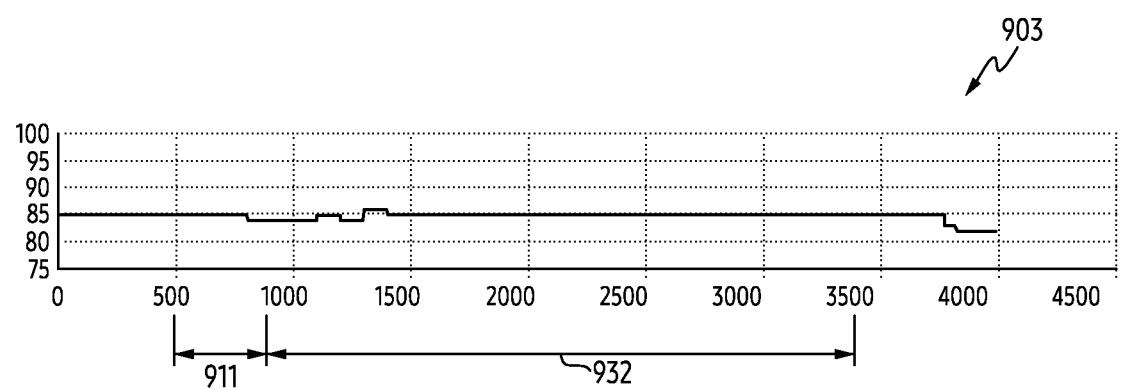
FIG. 9D is an example of a graph representing a change in heart rate over time identified in a wearable device according to an example embodiment.

FIG. 9D is an example of a graph representing a change in heart rate over time identified in a wearable device according to an embodiment.

In the following embodiment, each operation may be sequentially performed, but is not necessarily sequentially performed. For example, the order of each operation may be changed, and at least two operations may be performed in parallel.

According to an embodiment, operations 910 to 930 may be understood to be performed in a processor (e.g., the processor 410 of FIG. 4) of an electronic device (e.g., the electronic device 400 of FIG. 4).

Referring to FIG. 9A, in operation 910, the processor 410 may identify that the user is awake. For example, the processor 410 may identify that the user is awake based on identifying that the distance between wearable device 400 and the external electronic device is greater than or equal to a reference distance.

For example, in FIG. 7, the processor 410 may identify that the user is awake by performing an operation corresponding to operation 730. The processor 410 may identify that the user is awake based on identifying that the movement of the external electronic device corresponds to the movement of the user.

For example, in FIG. 7, the processor 410 may identify that the user is awake by performing an operation corresponding to operation 740. The processor 410 may identify the distance between the wearable device 400 and the external electronic device, and identify that the user is awake based on identifying that the distance between the wearable device 400 and the external electronic device is greater than or equal to a reference distance.

In operation 920, the processor 410 may identify whether the value indicating the movement of the wearable device 400 within the third time interval is greater than or equal to the second threshold value. The processor 410 may identify whether the value indicating the movement of the wearable device 400 within the third time interval is greater than or equal to the second threshold value, in order to identify whether the user is in a second state. For example, the processor 410 may identify whether the value indicating the movement of the wearable device 400 within the third time interval is greater than or equal to the second threshold value, in order to identify whether a fall has occurred to the user.

For example, the value indicating the movement of the wearable device 400 may be the magnitude of the acceleration of the wearable device 400. The processor 410 may identify whether the value indicating the movement of the wearable device 400 (or the magnitude of the acceleration of the wearable device 400) obtained using the acceleration sensor 431 (e.g., the acceleration sensor 431 of FIG. 4) is greater than or equal to the second threshold value.

According to an embodiment, when a value indicating a movement of the wearable device 400 within the third time interval is not greater than or equal to the second threshold value, the processor 410 may monitor movement of the wearable device 400.

According to an embodiment, when the value indicating the movement of the wearable device 400 within the third time interval is greater than or equal to the second threshold value, the processor 410 may identify that the user is in the second state. The processor 410 may identify that the user is in the second state based on that the value indicating the movement of the wearable device 400 within the third time interval is greater than or equal to the second threshold value. For example, the processor 410 may identify that a fall has occurred to the user while the user is awake, based on that the value indicating the movement of the wearable device 400 within the third time interval is greater than or equal to the second threshold value.

Referring to FIG. 9B, a graph 901 shows a change in the magnitude of acceleration over time of the wearable device 400. The x-axis of the graph 901 represents time. The unit of the x-axis is [ms(millisecond)]. The y-axis of the graph 901 represents the magnitude of acceleration. The unit of the y-axis is [m/s2 (meter per second squared)]. The processor 410 may identify acceleration of the wearable device 400 in three directions of the x-axis, the y-axis, and the z-axis using the acceleration sensor 431. The processor 410 may perform vector addition based on vectors representing accelerations in three directions of the x-axis, the y-axis, and the z-axis. The processor 410 may identify the magnitude of the resultant vector identified according to the vector addition as the magnitude of the acceleration of the wearable device 400.

For example, within the third time interval 911, the processor 410 may identify that the magnitude of the acceleration identified using the acceleration sensor 431 is greater than or equal to the second threshold value (e.g., 400 m/s2). The processor 410 may identify that the user is in a second state based on identifying that the magnitude of the acceleration identified using the acceleration sensor 431 within the third time interval 911 is greater than or equal to the second threshold value. The processor 410 may identify that a fall has occurred to the user while the user is awake, based on identifying that the magnitude of the acceleration identified using the acceleration sensor 431 within the third time interval 911 is greater than or equal to the second threshold value.

For example, the second threshold value may be distinguished from the first threshold value of FIG. 8A. The second threshold value may be set to be greater than the first threshold value. In case that a fall occurs while the user is awake, the user may reduce the impact on the body through a part of the body (e.g., the hand) when falling. When the wearable device 400 is worn close to a part of the user, the magnitude of the impact applied to the wearable device 400 may be large. Accordingly, the processor 410 may set the second threshold value to be greater than the first threshold value.

Referring to FIG. 9A, the processor 410 may identify a change in air pressure within a third time interval to identify that the user is in the second state. For example, the processor 410 may identify a change in position from the ground of the wearable device 400 based on a change in air pressure within the third time interval.

For example, the processor 410 may identify that the user is in a second state based on that the maximum amount of change in air pressure within the third time interval is greater than or equal to the second reference change amount. The processor 410 may identify the minimum air pressure and the maximum air pressure within the third time interval. The processor 410 may identify the maximum amount of change in the air pressure based on the minimum air pressure and the maximum air pressure within the third time interval.

For example, the processor 410 may identify that the user is in the second state, based on that the air pressure change rate within the third time interval is greater than or equal to the second reference change rate. The processor 410 may identify a rate of change in air pressure within the third time interval. The processor 410 may identify the rate of change in air pressure by identifying the gradient of air pressure within the third time interval.

Referring to FIG. 9C, a graph 902 shows a change in air pressure over time of the wearable device 400. The x-axis of the graph 902 represents time. The unit of the x-axis is [ms(millisecond)]. The y-axis of the graph 902 represents the magnitude of the air pressure. The unit of the y-axis is [hPa(hectopascal)].

For example, the processor 410 may identify the maximum amount of change in air pressure within the third time interval 911. The processor 410 may identify that a fall has occurred to the user based on that the maximum amount of change in air pressure within the third time interval 911 is greater than or equal to the second reference change amount (e.g., 0.1 hPa). The processor 410 may identify the height (e.g., about 120 cm) at which the user falls based on the maximum amount of change in air pressure. The processor 410 may identify the height from the ground to the wearable device 400 worn on the user when the user is standing based on the height at which the user falls.

For example, the processor 410 may identify a rate of change in air pressure within the third time interval 911. The processor 410 may identify that a fall has occurred to the user while the user is awake based on that the rate of change in air pressure within the third time interval 911 is greater than or equal to the second reference change rate.

Referring to FIG. 9A, the processor 410 may identify that the user is in the second state, based on at least one of whether the value indicating the movement of the wearable device 400 within the third time interval is greater than or equal to the second threshold value, whether the maximum amount of change in air pressure within the third time interval is greater than or equal to the second reference amount of change, or whether the rate of change air pressure within the third time interval is greater than or equal to the second reference rate of change.

For example, the processor 410 may identify that the user is in the second state based identifying that a value indicating a movement of the wearable device 400 within the third time interval is greater than or equal to the second threshold value, the maximum amount of change in air pressure within the third time interval is greater than or equal to the second reference change amount, and the air pressure change rate within the third time interval is greater than or equal to the second reference change rate. For example, the processor 410 may identify that a fall has occurred to the user while the user is awake, based on identifying that a value indicating a movement of the wearable device 400 within the third time interval is greater than or equal to the second threshold value, the maximum amount of change in air pressure within the third time interval is greater than or equal to the second reference change amount, and the air pressure change rate within the third time interval is greater than or equal to the second reference change rate.

In operation 930, when the value indicating the movement of the wearable device 400 within the third time interval is greater than or equal to the second threshold value, the processor 410 may execute the predetermined second function. For example, the processor 410 may execute the predetermined second function based on that the value indicating the movement of the wearable device 400 within the third time interval is greater than or equal to the second threshold value. Operation 930 may correspond to operation 660 of FIG. 6.

According to an embodiment, the processor 410 may refrain from identifying that the difference between the user's maximum heart rate and the user's minimum heart rate within the fourth time interval is greater than or equal to the threshold heart rate based on identifying that the value indicating the movement of the wearable device 400 is greater than or equal to the second threshold value, and execute a predetermined second function. For example, the fourth time interval may be set after the third time interval.

For example, when a fall occurs to the user while the user is awake, the user's heart rate may not change after the fall occurs. Accordingly, the processor 410 may refrain from identifying that the difference between the user's maximum heart rate and the user's minimum heart rate within the fourth time interval is greater than or equal to the threshold heart rate.

For example, data obtained using the PPG sensor 433 (e.g., the PPG sensor 433 of FIG. 4) may not be used to identify whether the magnitude of the impact applied to the user is greater than or equal to the reference magnitude.

Referring to FIG. 9D, a graph 903 represents a change in the heart rate of a user over time. The x-axis of the graph 903 represents time. The unit of the x-axis is [ms(millisecond)]. The y-axis of the graph 903 represents a heart rate. The unit of the y-axis is [bpm(beats per minute)].

For example, the processor 410 may identify that a fall has occurred to the user while the user is awake within the third time interval 911. Within the fourth time interval 932 after the third time interval 911, the user's heart rate may not change. Accordingly, the processor 410 may refrain from or bypass identifying that the difference between the user's maximum heart rate and the user's minimum heart rate within the fourth time interval 932 is greater than or equal to the threshold heart rate.

Figure 10:
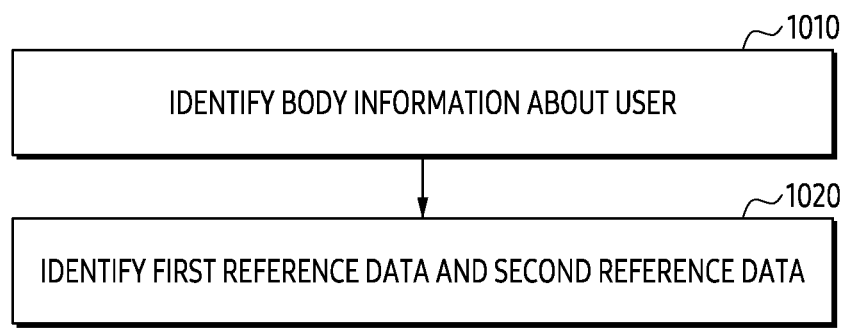
FIG. 10 is a flowchart illustrating an exemplary operation of a wearable device according to an example embodiment.

FIG. 10 is a flowchart illustrating an exemplary operation of a wearable device according to an embodiment.

In the following embodiment, each operation may be sequentially performed, but is not necessarily sequentially performed. For example, the order of each operation may be changed, and at least two operations may be performed in parallel.

According to an embodiment, operations 1010 to 1020 may be understood to be performed in a processor (e.g., the processor 410 of FIG. 4) of an electronic device (e.g., the electronic device 400 of FIG. 4).

Referring to FIG. 10, in operation 1010, the processor 410 may identify body information about the user. For example, the body information about the user may include at least one of the user's gender, age, height, weight, and/or physical activity ability.

In operation 1020, the processor 410 may identify the first reference data and the second reference data based on the body information about the user. For example, the processor 410 may identify first reference data for identifying the user's first state and second reference data for identifying the user's second state, based on body information about the user.

According to an embodiment, data obtained by the fall may be different according to at least one of the user's gender, age, height, weight, and/or physical activity ability. Accordingly, the processor 410 may change parameters (e.g., a first threshold value or a second threshold value) for identifying the fall according to at least one of the user's gender, age, height, weight, and/or physical activity ability.

For example, the physical activity ability may be set based on information on the number of steps, the moving distance, and the calorie consumption during a designated time. The processor 410 may identify information on the number of steps, the moving distance, and the calorie consumption during a designated time based on the data obtained using the sensor 430 (e.g., the sensor 430 of FIG. 4). The processor 410 may identify the user's physical activity ability based on information on the number of steps, the moving distance, and the calorie consumption during a designated time.

According to an embodiment, the processor 410 may set (or change) a threshold heart rate for identifying that the magnitude of the impact applied to the user is greater than or equal to a reference magnitude. The processor 410 may set a threshold heart rate based on the user's age and the user's physical activity ability. For example, as the user's age increases, the rate of increase in heart rate due to fall may increase. For example, as the user's physical activity ability decreases, the rate of increase in heart rate due to fall may increase. For example, the processor 410 may set a threshold heart rate as shown in Equation 1.

$$HR_{thrd} = (A \times \alpha) + \left(\frac{1}{P} \times \beta\right) + \gamma \quad \text{[Equation 1]}$$

Equation 1 is only an example for understanding, is not limited thereto, and may be modified, applied, or expanded in various ways.

Referring to Equation 1, $HR_{thrd}$ is a threshold heart rate. A is the age of the user. P is a value indicating the user's physical activity ability. $\alpha$(alpha), $\beta$(beta), and $\gamma$(gamma) are coefficients.

According to an embodiment, the processor 410 may increase the threshold heart rate as the age of the user increases. The processor 410 may increase the threshold heart rate as the user's physical activity ability decreases. Accordingly, the processor 410 may provide a service for each user by setting a different threshold heart rate according to the user.

Figure 11:
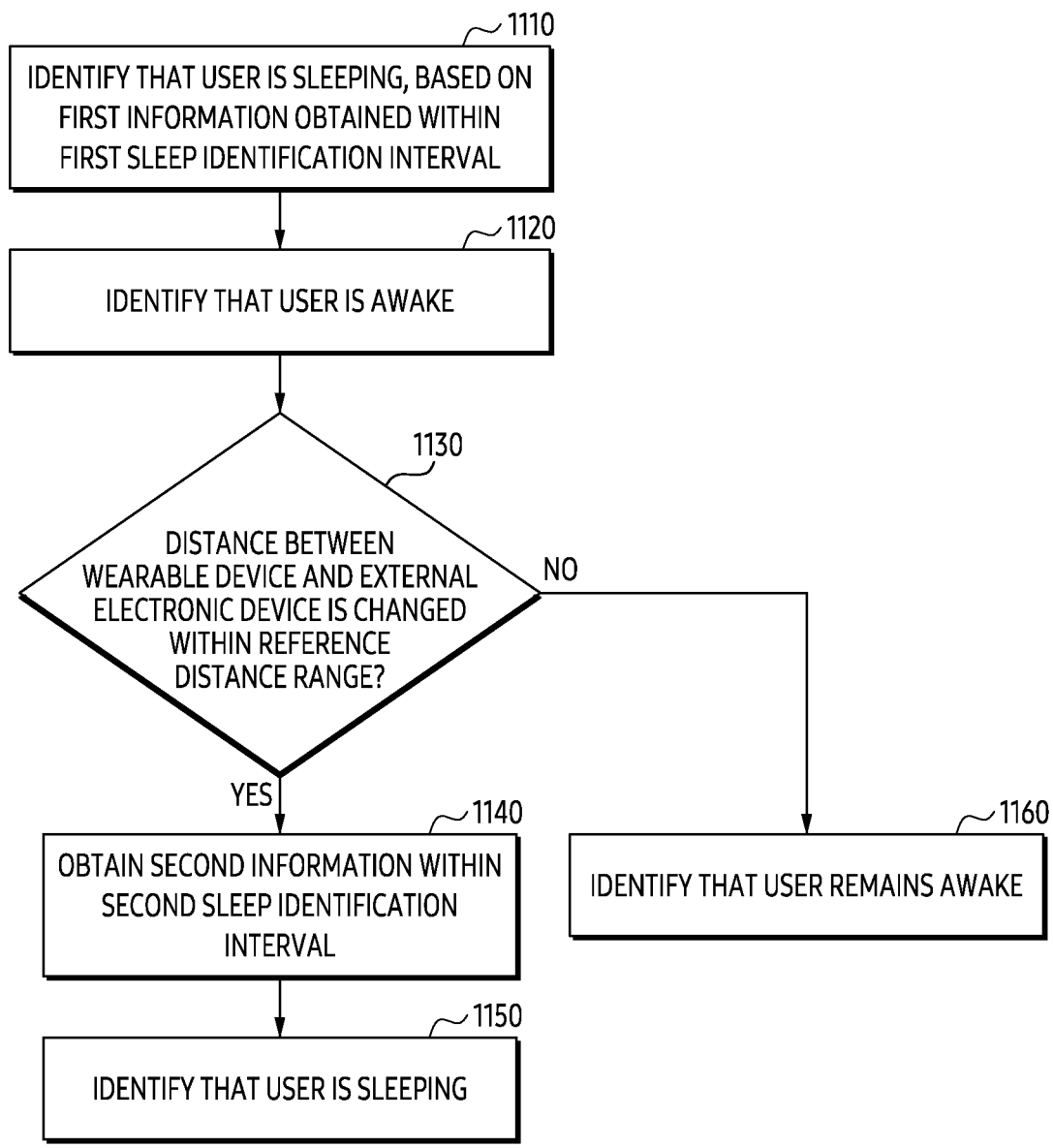
FIG. 11 is a flowchart illustrating an exemplary operation of a wearable device according to an example embodiment.

FIG. 11 is a flowchart illustrating an exemplary operation of a wearable device according to an embodiment.

In the following embodiment, each operation may be sequentially performed, but is not necessarily sequentially performed. For example, the order of each operation may be changed, and at least two operations may be performed in parallel.

According to an embodiment, operations 1110 to 1150 may be understood to be performed in a processor (e.g., the processor 410 of FIG. 4) of an electronic device (e.g., the electronic device 400 of FIG. 4).

Referring to FIG. 11, in operation 1110, the processor 410 may identify that the user is sleeping based on the first information obtained within the first sleep identification interval (e.g., about 30 minutes). For example, the processor 410 may obtain the first information using the sensor 430 (e.g., the sensor 430 of FIG. 4) (or at least one sensor) within the first sleep identification interval. The processor 410 may identify that the user is sleeping based on the first information obtained using the sensor 430 within the first sleep identification interval.

According to an embodiment, the processor 410 may identify a user's location. For example, the processor 410 may identify that the user's location is in the bedroom. After identifying that the user's location is in the bedroom, the processor 410 may identify that the user is sleeping based on the first information obtained using the sensor 430 within the first sleep identification interval.

According to an embodiment, the processor 410 may identify that the user is sleeping based on the first information obtained during the first sleep identification interval using an acceleration sensor (e.g., the acceleration sensor 431 in FIG. 4), a gyro sensor (e.g., the gyro sensor 432 in FIG. 4), and/or a PPG sensor (e.g., the PPG sensor 433 in FIG. 4). For example, the processor 410 may identify that the value indicating the user's movement obtained during the first sleep identification interval through at least one of the acceleration sensor 431 and/or the gyro sensor 432 is less than the first threshold value, and identify that the user is sleeping based on identifying that the user's heart rate obtained through the PPG sensor 433 is less than the threshold heart rate.

According to an embodiment, the processor 410 may activate a first module 411 (e.g., the first module 411 in FIG. 5) of the first module 411 and the second module 412 (e.g., the second module 412 in FIG. 5) for identifying the fall based on identifying that the user is sleeping. The processor 410 may activate the first module 411 and deactivate the second module 412 based on identifying that the user is sleeping. The processor 410 may identify whether a fall occurs to the user while the user is sleeping using the first module 411. Each of the first module 411 and the second module 412 may comprise circuitry.

In operation 1120, the processor 410 may identify that the user is awake. For example, the processor 410 may identify that the user is awake, based on at least in a part on identifying that the distance between wearable device 400 and the external electronic device is greater than or equal to the reference distance.

For example, the processor 410 may identify that the distance between the wearable device 400 and the external electronic device is greater than or equal to a reference distance. The processor 410 may identify that the user is awake based at least in part on identifying that the distance between wearable device 400 and the external electronic device is greater than or equal to a reference distance.

According to an embodiment, the processor 410 may identify whether the distance between the wearable device 400 and the external electronic device is greater than or equal to a reference distance to identify whether the user has left the bed. The external electronic device may be placed in a fixed position while the user is sleeping. The processor 410 may identify whether the user has left the bed by identifying whether the distance between wearable device 400 and the external electronic device placed in a fixed position while the user is sleeping is greater than or equal to the reference distance.

According to an embodiment, the processor 410 may identify a plurality of steps of the user using the sensor 430. The processor 410 may identify that the number of the plurality of steps of the user is greater than or equal to the threshold number of steps. The processor 410 may identify the movement of the user based on identifying that the number of the plurality of steps of the user is greater than or equal to the threshold number of steps. The processor 410 may identify that the distance between the wearable device 400 and the external electronic device is greater than or equal to a reference distance, based on identifying that the number of the plurality of steps of the user is greater than or equal to the threshold number of steps. After identifying that the number of the plurality of steps of the user is greater than or equal to the threshold number of steps, the processor 410 may identify that the distance between the wearable device 400 and the external electronic device is greater than or equal to a reference distance.

According to an embodiment, the processor 410 may identify a distance between the wearable device 400 and the external electronic device using a communication circuit (e.g., the communication circuit 420 of FIG. 4). For example, the processor 410 may transmit a UWB signal to the external electronic device using the communication circuit 420. The processor 410 may identify a distance between the wearable device 400 and an external electronic device, based on the reflection signal that the transmitted UWB signal is reflected from the external electronic device and received at least in part. For example, the processor 410 may transmit a UWB signal to an external electronic device using the communication circuit 420. The processor 410 may receive a response signal to the UWB signal from an external electronic device. The processor 410 may identify a distance between the wearable device 400 and the external electronic device based on the UWB signal and the response signal. For example, the processor 410 may identify a receive signal strength indicator (RSSI) of a Bluetooth signal received from an external electronic device. The processor 410 may identify a distance between the wearable device 400 and the external electronic device based on a receive signal strength indicator (RSSI) of a Bluetooth signal received from the external electronic device.

According to an embodiment, the external electronic device may be carried by a user and moved together with the user. The processor 410 may identify that the movement of the external electronic device corresponds to the movement of the user. The processor 410 may identify that the user is awake based on that the movement of the external electronic device corresponds to the movement of the user.

For example, the processor 410 may identify a plurality of first steps of the user using the sensor 430. The processor 410 may identify that the number of a plurality of first steps of the user is greater than or equal to the first threshold number of steps. The processor 410 may identify that the number of a plurality of second steps of the user identified by the external electronic device is greater than or equal to the second threshold number of steps. The processor 410 may identify that the user is awake, based on identifying that the number of the plurality of first steps is greater than or equal to the first threshold number of steps, and the number of the plurality of second steps is greater than or equal to the second threshold number of steps.

For example, the plurality of first steps may be identified using the sensor 430 of the wearable device 400. The plurality of second steps may be identified using an external electronic device. Since the measurement device is different, the number of a plurality of first steps and the number of a plurality of second steps may be differently identified. Accordingly, the processor 410 may set the first threshold number of steps and the second threshold number of steps differently. The processor 410 may identify that a user wearing the wearable device 400 is moving with an external electronic device, based on identifying that the number of the plurality of first steps is greater than or equal to the first threshold number of steps, and the number of the plurality of second steps is greater than or equal to the second threshold number of steps. The processor 410 may identify that the user is awake, based on identifying that the number of the plurality of first steps is greater than or equal to the first threshold number of steps, and the number of the plurality of second steps is greater than or equal to the second threshold number of steps.

According to an embodiment, the processor 410 may identify that the altitude difference between the wearable device 400 and the external electronic device is changed using a barometric pressure sensor 434 (e.g., the barometric pressure sensor 434 of FIG. 4). The processor 410 may identify that the user is awake based on identifying that the altitude difference between the wearable device 400 and the external electronic device is changed.

According to an embodiment, the processor 410 may activate a second module 412 of the first module 411 and the second module 412 for identifying a fall, based on identifying that the user is awake. For example, the processor 410 may deactivate the first module 411 and activate the second module 412 based on identifying that the user is awake. The processor 410 may identify whether a fall occurs to the user while the user is awake using the second module 412.

In operation 1130, the processor 410 may identify whether the distance between the wearable device 400 and the external electronic device is changed within the reference distance range. For example, the processor 410 may identify whether the distance between the wearable device 400 and the external electronic device is changed within a reference distance to determine whether the user returns to the bed.

In operation 1140, when the processor 410 identifies that the distance between the wearable device 400 and the external electronic device is changed within the reference distance, the processor 410 may obtain the second information within the second sleep identification interval (e.g., about 10 minutes). For example, the processor 410 may obtain second information within the second sleep identification interval based on identifying that the distance between wearable device 400 and the external electronic device is changed within the reference distance.

In operation 1150, the processor 410 may identify that the user is sleeping. For example, the processor 410 may identify that the user is sleeping based on the second information obtained within the second sleep identification interval.

For example, the second sleep identification interval may be set shorter than the first sleep identification interval. The user of the wearable device 400 may temporarily leave the bed while sleeping, and then return to the bed and fall asleep. When the user temporarily leaves the bed while sleeping and then returns to the bed and falls asleep, the processor 410 may obtain the second information using the sensor 430 (or at least one sensor) within the second sleep identification interval set shorter than the first sleep identification interval. The processor 410 may identify that the user has fallen asleep again based on the second information obtained using the sensor 430 within the second sleep identification interval.

For example, processor 410 may identify that the user is sleeping, based on identifying that the value indicating the user's movement within the second sleep identification interval is less than the first threshold value. For example, the processor 410 may identify that the user is sleeping based on identifying that the user's heart rate obtained through the PPG sensor 433 within the second sleep identification interval is less than the threshold heart rate. For example, the processor 410 may identify that the altitude (or distance from the ground) of the wearable device 400 identified through the barometric pressure sensor 434 within the second sleep identification interval corresponds to the altitude when the user is sleeping. The processor 410 may identify that the user has fallen asleep again, based on identifying that the altitude of the wearable device 400 identified through the barometric pressure sensor 434 within the second sleep identification interval corresponds to the altitude when the user is sleeping.

According to an embodiment, the second module 412 may be used to identify that a fall occurs to the user while the user is awake, and to identify the type of fall. Accordingly, the power required for the operation of the second module 412 may be greater than the power required for the operation of the first module 411. The processor 410 may change a module for identifying a fall from the second module 412 to the first module 411, by determining whether the user falls asleep again during the second sleep identification interval, which is shorter than the first sleep identification interval. Power consumption may be reduced and accuracy for identifying the fall of the user may be improved, by changing the module for identifying the fall by the processor 410 from the second module 412 to the first module 411.

In operation 1160, when the distance between the wearable device 400 and the external electronic device does not change within the reference distance, the processor 410 may identify that the user remains awake. The processor 410 may identify that the user remains awake based on identifying that the distance between wearable device 400 and the external electronic device does not change within the reference distance.

According to an embodiment, the processor 410 may maintain the module for identifying the fall as the second module 412 based on identifying that the user remains awake.

According to an embodiment, the processor 410 may identify that the user is awake based on that the movement of the external electronic device corresponds to the movement of the user. After identifying that the user is awake based on the movement of the external electronic device corresponding to the user's movement, the processor 410 may identify that the user has fallen asleep again based on identifying that the value indicating the movement of the user within the first sleep identification interval is less than the first threshold value.

For example, the processor 410 may identify that the user is awake, based on the distance between the external electronic device and wearable device 400 placed in a fixed position while the user is sleeping. The processor 410 may identify that the user has fallen asleep again based on identifying that the value indicating the movement of the user within the second sleep identification interval is less than the first threshold value. For example, the processor 410 may identify that the user is awake based on the movement of the external electronic device corresponding to the movement of the user. The processor 410 may identify that the user has fallen asleep again, based on identifying that the value indicating the user's movement within the first sleep identification interval longer than the second sleep identification interval is less than the first threshold value.

Figure 12:
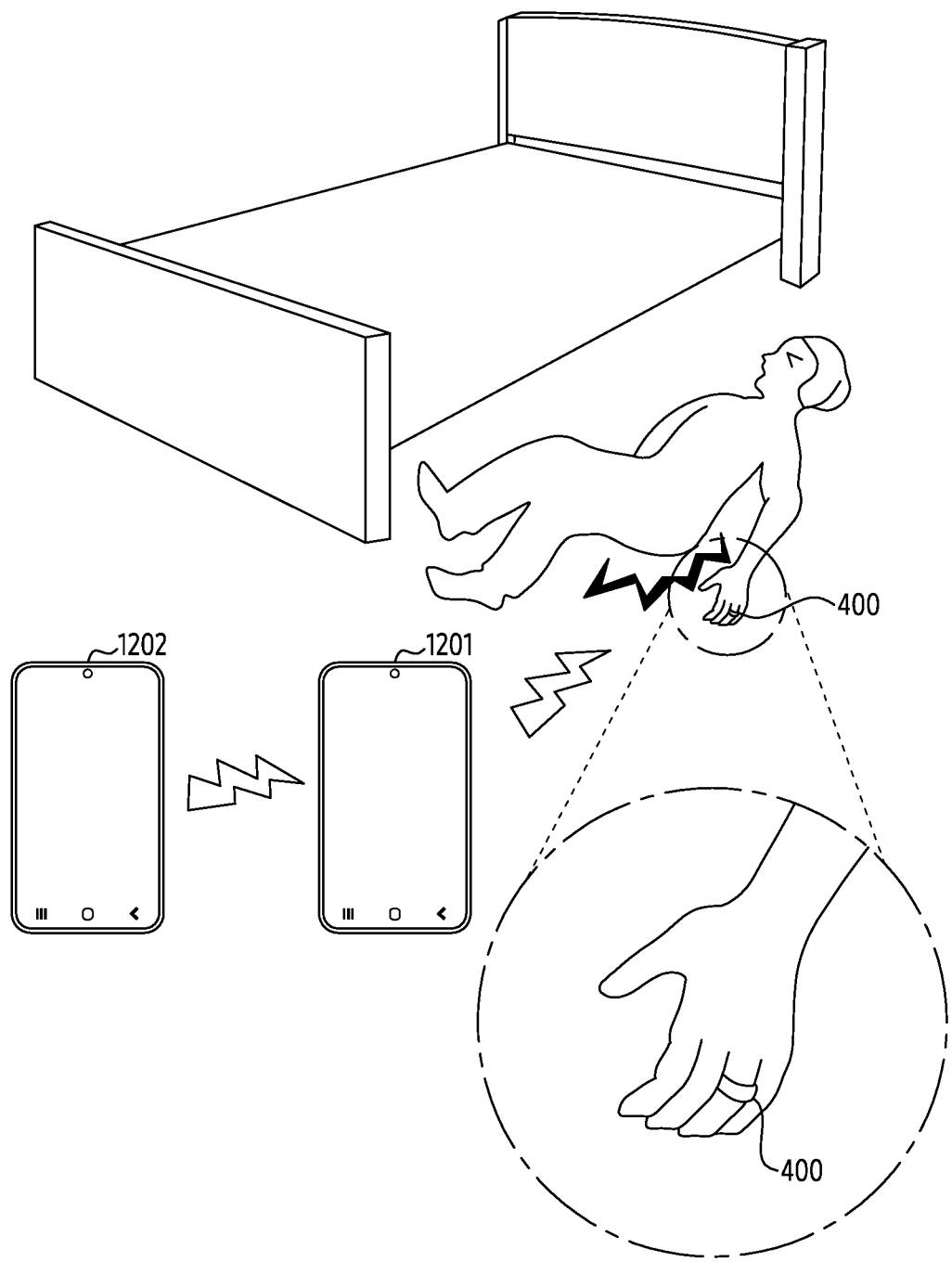
FIG. 12 illustrates an example of an operation of a wearable device according to an example embodiment.

FIG. 12 illustrates an example of an operation of a wearable device according to an embodiment.

Referring to FIG. 12, the processor 410 (e.g., the processor 410 of FIG. 4) of the wearable device 400 may identify that the user is sleeping. For example, the processor 410 may identify that the user is sleeping based on the first information obtained using the sensor 430 (e.g., the sensor 430 of FIG. 4) within the first sleep identification interval. For example, the processor 410 may identify that the user is sleeping, based on identifying that the value indicating the user's movement is less than the first threshold value using the acceleration sensor 431 (e.g., the acceleration sensor 431 in FIG. 4).

The processor 410 may activate the first module 411 (e.g., the first module 411 of FIG. 4) among the first module 411 and the second module 412 (e.g., the second module 412 of FIG. 4) for identifying the fall, based on identifying that the user is sleeping. For example, the processor 410 may deactivate the second module 412 and activate the first module 411 based on identifying that the user is sleeping.

The processor 410 may identify a distance between the wearable device 400 and the external electronic device 1201. The processor 410 may identify that the user maintains a sleeping state, based on identifying that the distance between wearable device 400 and external electronic device 1201 is less than the reference distance. The processor 410 may obtain data (e.g., biometric data) about a user through the sensor 430. For example, the data on the user may include at least one of data on the user's movement, data on the orientation of the wearable device 400, data on the user's heart rate, and/or data on the air pressure around wearable device 400.

The processor 410 may compare data on the user with first reference data. Based on identifying that the data for the user corresponds to the first reference data, the processor 410 may identify that a fall occurs in a user sleeping, and the magnitude of the impact applied to the user is greater than or equal to the reference magnitude. The processor 410 may execute a predetermined first function according to a comparison between data on the user and the first reference data. For example, the processor 410 may transmit a signal for calling a designated contact (e.g., an SOS call or an emergency contact) to the external electronic device 1201. The processor 410 may control the external electronic device 1201 to call another user corresponding to the external electronic device 1202 through the external electronic device 1201. For example, the processor 410 may control the external electronic device 1201 to transmit a signal to the external electronic device 1202 operating as a server (e.g., a server for receiving emergency signals) through the external electronic device 1201 to notify that the user is in an emergency.

According to an embodiment, even when additional infrastructure other than wearable device 400 and external electronic device 1201 is not established, an effect of detecting a fall of a sleeping user or detecting a fall of a waking user exists. According to an embodiment, in a place (e.g., senior care center or hospital) that a fatal accident may occur to the user when the user falls from the bed, there is an effect of quickly determining the user's fall and quickly notifying the external electronic devices 1201 and 1202 that the user's fall occurred during sleep.

Figure 13:
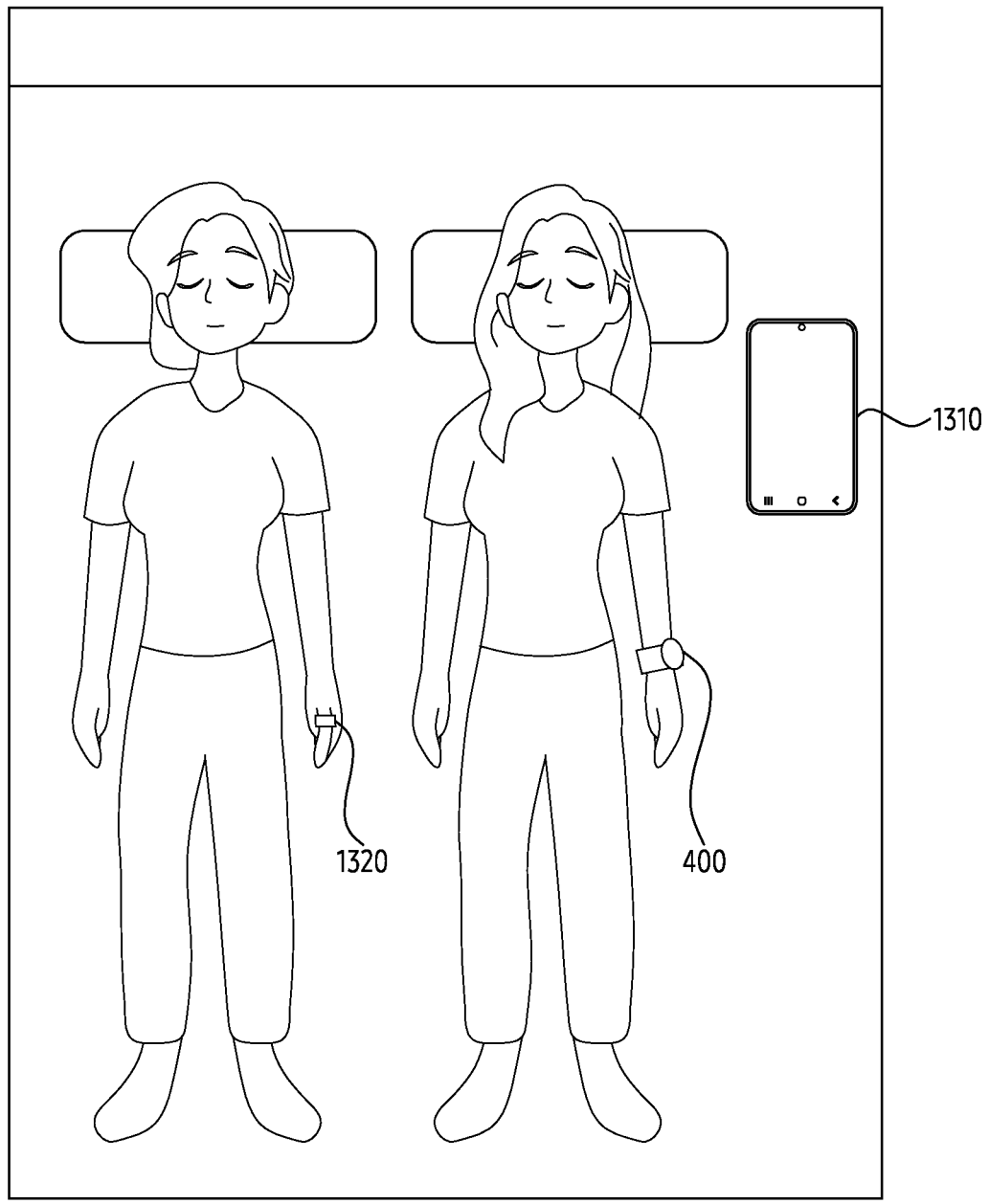
FIG. 13 illustrates an example of an operation of a wearable device according to an example embodiment.

FIG. 13 illustrates an example of an operation of a wearable device according to an embodiment.

Referring to FIG. 13, the wearable device 400 may be connected, directly or indirectly, to an external electronic device 1310. The external electronic device 1310 may be connected, directly or indirectly, to the external electronic device 1320 as well as the wearable device 400. The external electronic device 1320 may be worn on a part of the body of another user distinguished from the user of the wearable device 400. For example, the user and the other user may be located within the same space (e.g., a space corresponding to the size of the bed).

According to an embodiment, the first account registered in the wearable device 400 and the second account registered in the external electronic device 1320 may be configured as one group (e.g., a family group). The external electronic device 1310 may be used to manage the wearable device 400 according to the first account and the external electronic device 1320 according to the second account. For example, the external electronic device 1310 may control the wearable device 400 and/or the external electronic device 1320.

According to an embodiment, the processor 410 of the wearable device 400 may identify distances between the wearable device 400 and the external electronic device 1320. For example, the processor 410 may identify a distance between the wearable device 400 and the external electronic device 1310. The processor 410 may receive information on the distance between the external electronic device 1310 and the external electronic device 1320. The processor 410 may identify a first direction of a signal transmitted from the external electronic device 1310 to the wearable device 400. The processor 410 may identify a second direction of a signal transmitted from the external electronic device 1320 to the external electronic device 1310. The processor 410 may identify an angle between the first direction and the second direction based on the first direction and the second direction. The processor 410 may identify a distance between the wearable device 400 and the external electronic device 1320, based on the distance between the wearable device 400 and the external electronic device 1310, the distance between the external electronic device 1310 and the external electronic device 1320, and the identified angle.

According to an embodiment, the processor 410 may identify whether the user of the wearable device 400 is sleeping based on the distance between the wearable device 400 and the external electronic device 1320. According to an embodiment, the processor 410 may identify whether another user of the external electronic device 1320 is sleeping based on the distance between the wearable device 400 and the external electronic device 1320.

For example, the processor 410 may identify that the user is awake by identifying whether the user of the wearable device 400 leaves the bed based on the distance between wearable device 400 and external electronic device 1320.

Unlike FIG. 13, according to an embodiment, the wearable device 400 may be connected to the first electronic device. The external electronic device 1320 may be connected to the second electronic device. The wearable device 400 connected to the first electronic device may establish a connection with the external electronic device 1320 connected to the second electronic device. The wearable device 400 connected to the first electronic device may identify a distance with the external electronic device 1320 connected to the second electronic device, and identify whether the user of the wearable device 400 is sleeping based on the distance.

Figure 14:
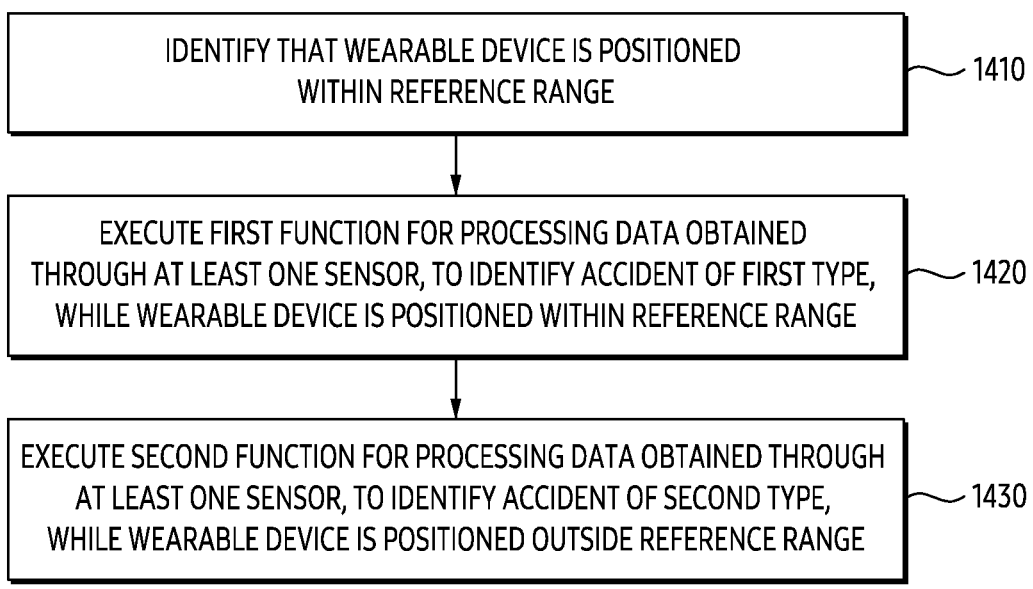
FIG. 14 is a flowchart illustrating an exemplary operation of a wearable device, according to an example embodiment.

FIG. 14 is a flowchart illustrating an exemplary operation of a wearable device, according to an embodiment.

In the following embodiment, each operation may be performed sequentially, but is not necessarily performed sequentially. For example, the order of each operation may be changed, and at least two operations may be performed in parallel.

According to an embodiment, operations 1410 to 1430 may be understood to be performed on a processor (e.g., the processor 410 of FIG. 4) of an electronic device (e.g., the electronic device 400 of FIG. 4).

Referring to FIG. 14, in operation 1410, the processor 410 may be configured to identify that the wearable device 400 is positioned within a reference range. For example, the processor 410 may be configured to identify whether the wearable device 400 is located within the reference range, via at least the communication circuit 420. The processor 410 may be configured to identify that the wearable device 400 is positioned within the reference range, based on identifying a position of the wearable device 400.

According to an embodiment, the reference range may be set based on a distance between the wearable device 400 and an external electronic device connected to the wearable device 400. For example, the processor 410 may identify that the wearable device 400 is positioned outside the reference range, based on a fact that the distance between the wearable device 400 and the external electronic device exceeds the threshold distance. For example, the processor 410 may identify that the wearable device 400 is positioned within the reference range, based on a fact that the distance between the wearable device 400 and the external electronic device is less than or equal to the threshold distance.

According to an embodiment, the reference range may be set based on a designated distance from the wearable device 400. The processor 410 may set a region within the designated distance from the wearable device 400 as the reference range.

For example, the processor 410 may set a reference range based on a designated distance from a position where the user's state is identified as a first state. For example, the first state may be referred to as a sleep state. A second state may be referred to as an awake state. For example, the first state may be referred to as a driving state. The second state may be referred to as a non-driving state. For example, the first state may be referred to as a state in which a user of the wearable device 400 is located in a designated space (e.g., a house). The second state may be referred to as a state in which the user of the wearable device 400 is positioned outside the designated space (e.g., outside the house).

In operation 1420, the processor 410 may execute a first function for processing data obtained through at least a sensor 430 (e.g., at least one sensor) to identify an accident of a first type, while the wearable device 400 is positioned within the reference range.

For example, the processor 410 may identify that the wearable device 400 is positioned within the reference range. The processor 410 may execute the first function to identify the accident of the first type, based on a fact that the wearable device 400 is positioned within the reference range.

In operation 1430, the processor 410 may execute a second function for processing data obtained through the sensor 430 (e.g., at least one sensor), to identify an accident of a second type, while the wearable device 400 is positioned outside the reference range.

For example, the processor 410 may identify that the wearable device 400 is positioned outside the reference range. The processor 410 may execute the second function to identify the accident of the second type, based on a fact that the wearable device 400 is positioned outside the reference range.

For example, the processor 410 may activate a first number of sensors based on execution of the first function. The processor 410 may activate a second number of sensors based on execution of the second function. The second number may be set greater than or equal to the first number. For example, the processor 410 may activate the acceleration sensor 431 based on execution of the first function. The processor 410 may activate the acceleration sensor 431 and the PPG sensor 433 based on execution of the second function.

For example, a first power consumption while the first function is being executed may be less than a second power consumption while the second function is being executed. Since the first number of sensor(s) is activated while the first function is being executed, and the second number of sensor(s) is activated while the second function is being executed, the first power consumption while the first function is being executed may be less than the second power consumption while the second function is being executed.

For example, the accident of the first type may include an accident in which the user falls from the bed. And an example accident of the second type may include an accident in which the user falls while walking. For example, the accident of the first type may include a collision accident between automobiles. And an example accident of the second type may include an accident in which the user falls while walking. For example, the accident of the first type may include an accident in which the user falls within a designated space (e.g., home) for the user of the wearable device 400. And an example accident of the second type may include an accident in which the user falls outside the designated space for the user of the wearable device 400.

According to an embodiment, the processor 410 may control to transmit a first signal indicating occurrence of the accident of the first type based on the occurrence of the accident of the first type. For example, the processor 410 may transmit the first signal indicating occurrence of the accident of the first type, in response to the accident of the first type.

For example, the first signal and the second signal may be transmitted based on a broadcast technique. For example, the first signal and the second signal may include an advertising message. For example, the first signal and the second signal may be set so that there is no target device of the signal.

For example, the processor 410 may control to transmit the first signal to peripheral devices of the wearable device 400 based on the occurrence of the accident of the first type. The first signal may be set to cause the peripherals of the wearable device 400 to provide a notification indicating that the accident of the first type has occurred.

For example, the processor 410 may transmit the second signal to peripheral devices of the wearable device 400 based on the occurrence of the accident of the second type. The second signal may be set to cause the peripheral devices of the wearable device 400 to provide a notification indicating that the accident of the second type has occurred.

According to an embodiment, the processor 410 may identify data obtained through at least one component as well as the sensor 430. For example, the processor 410 may identify data obtained through the microphone 450. For example, the processor 410 may identify one of the accident of the first type and the accident of the second type, based on data obtained through the microphone 450 and data obtained through the sensor 430. The processor 410 may identify the occurrence of the accident of the first type, based on a fact that loudness of a sound obtained through the microphone 450 is greater than or equal to threshold loudness, for example. The processor 410 may identify the occurrence of the accident of the second type based on a fact that the loudness of the sound obtained through the microphone 450 is less than the threshold loudness, for example.

According to an embodiment, the processor 410 may identify the accident of the first type. The processor 410 may obtain data related to the accident of the second type through the sensor 430, after identifying the accident of the first type. The processor 410 may identify that the accident of the second type rather than the first type has occurred, based on obtaining data related to the accident of the second type. However, it is not limited thereto. For example, the processor 410 may identify that the accident of the first type rather than the second type has occurred, based on obtaining data related to the accident of the first type, after identifying the accident of the second type.

Figure 15A:
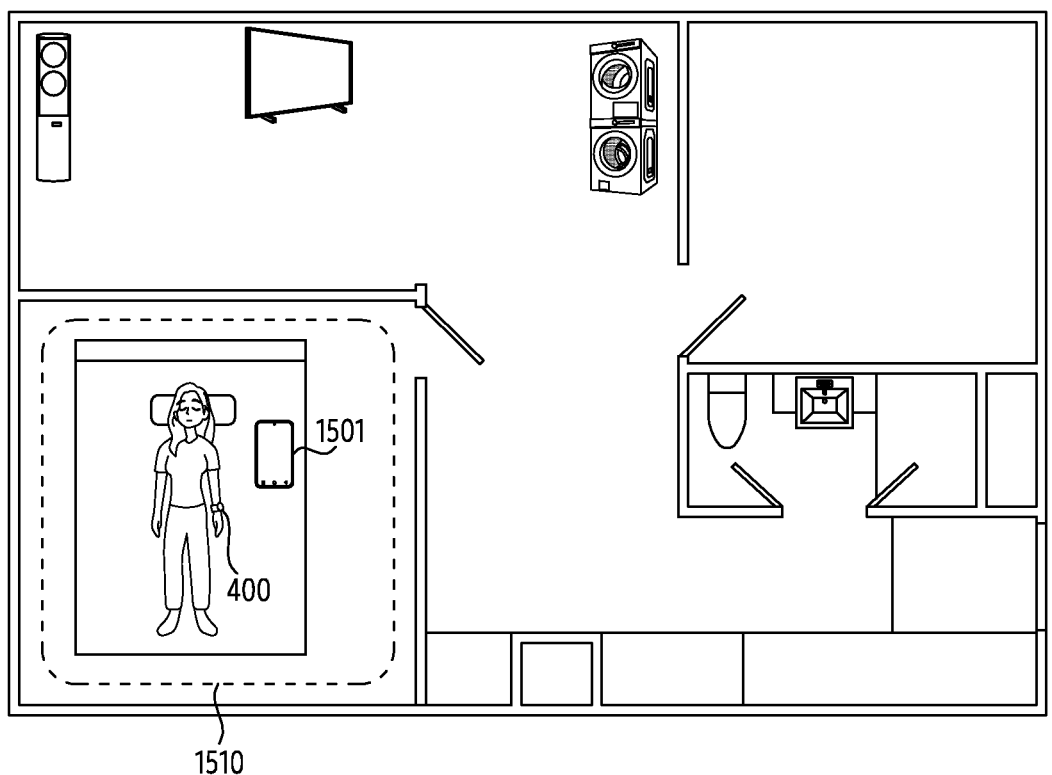
FIG. 15A illustrates an example of an operation of a wearable device, according to an example embodiment.

FIG. 15A illustrates an example of an operation of a wearable device, according to an embodiment.

Referring to FIG. 15A, the processor 410 may set a reference range 1510. The processor 410 may identify at least one of the accident of the first type and the accident of the second type based on the reference range 1510.

According to an embodiment, the reference range 1510 may be set based on a distance between the wearable device 400 and the external electronic device 1501 connected to the wearable device 400. The reference range 1510 may be set based on the external electronic device 1501. The processor 410 may identify that the wearable device 400 is positioned within the reference range, based on a fact that the distance between the wearable device 400 and the external electronic device 1501 is less than or equal to a threshold distance, for example. The processor 410 may identify that the wearable device 400 is positioned outside the reference range, based on a fact that the distance between the wearable device 400 and the external electronic device 1501 exceeds the threshold distance, for example.

For example, the external electronic device 1501 may be in a fixed state. For example, the external electronic device 1501 may be positioned in a space next to the bed. The external electronic device 1501 may be positioned at a fixed position while the user is lying on the bed (or sleeping on the bed). The processor 410 may identify that a position of the external electronic device 1501 is maintained. The position of the external electronic device 1501 may be maintained to charge a rechargeable battery of the external electronic device 1501. The processor 410 may identify that the external electronic device 1501 is in a fixed state, based on identifying that the external electronic device 1501 is being charged.

According to an embodiment, the reference range 1501 may be set based on the position of the wearable device 400. For example, the processor 410 may identify the position of the wearable device 400, based on signal exchange between the wearable device 400 and peripheral electronic devices. For example, the processor 410 may identify information on latitude and longitude of the wearable device 400 using a GPS circuit. For example, the processor 410 may identify the position of the wearable device 400 within a designated space (e.g., home) for the user.

For example, the processor 410 may set the reference range 150. For example, the processor 410 may set the user's sleeping space as the reference range 1501. FIG. 15A illustrates an example in which the user's sleeping space is set as the reference range 1501, but is not limited thereto. For example, the processor 410 may set a designated space (e.g., home) for the user as the reference range 1501.

According to an embodiment, the processor 410 may set a reference range, based on a distance designated from a position where a state of the user of the wearable device 400 is identified as the first state. For example, the processor 410 may identify the state of the user of the wearable device 400 as a sleep state. The processor 410 may set a reference range, based on a distance designated from a position where the user's state is identified as the sleeping state.

Figure 15B:
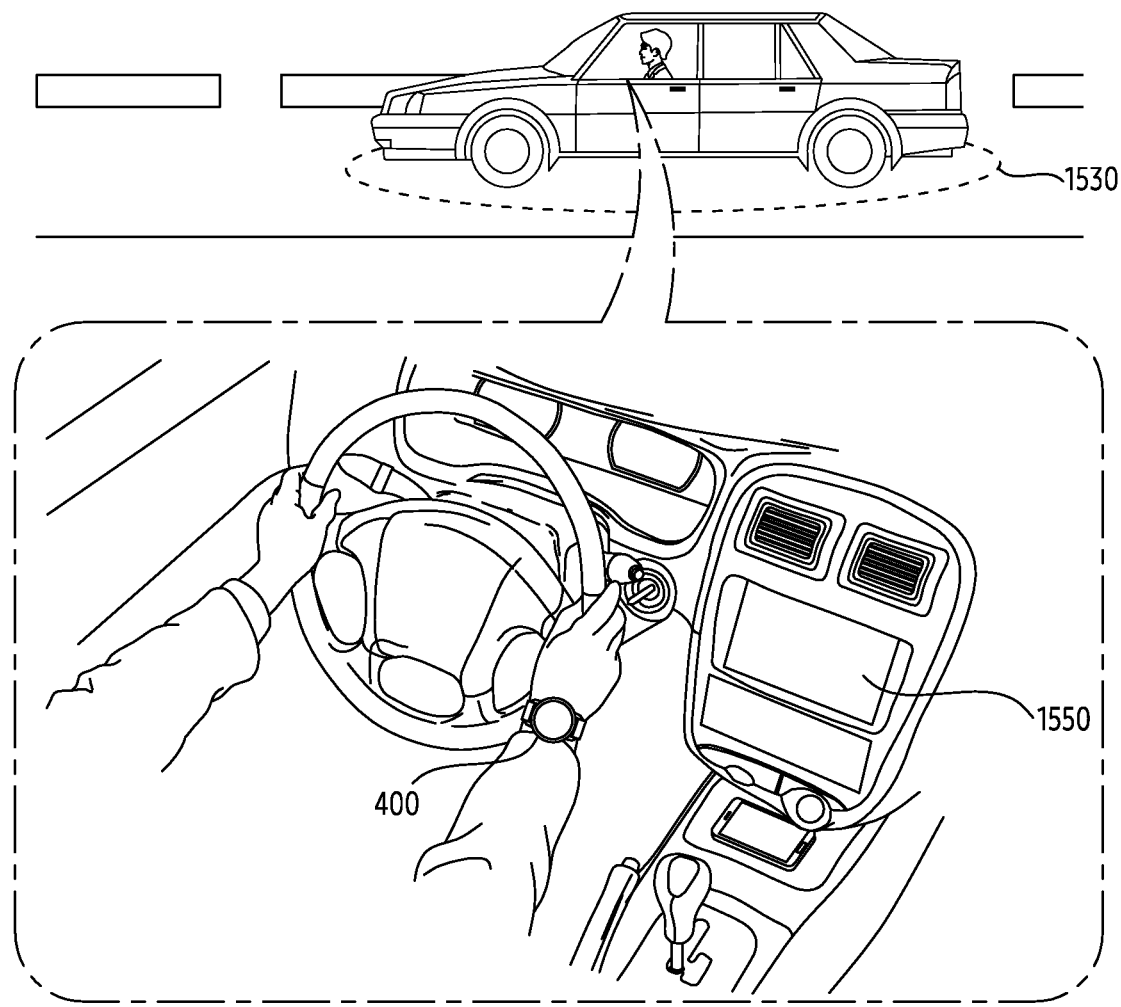
FIG. 15B illustrates an example of an operation of a wearable device according to an example embodiment.

FIG. 15B illustrates an example of an operation of a wearable device according to an embodiment.

Referring to FIG. 15B, the processor 410 may set a reference range 1530. The processor 410 may identify at least one of the accident of the first type and the accident of the second type, based on the reference range 1530.

For example, the processor 410 may set the reference range 1530 based on a connection with the external electronic device 1550. The processor 410 may set the reference range 1530 based on the connection with the external electronic device 1550 included in the vehicle. The processor 410 may set a space in the vehicle as the reference range 1530. The reference range 1530 may not be an absolute position, in an example. For example, the reference range 1530 may be changed according to the movement of the vehicle. The processor 410 may maintain the reference range 1530 as a space in the vehicle, for example.

For example, the processor 410 may establish a connection with the external electronic device 1550 included in the vehicle. The processor 410 may identify that the user is riding the vehicle, based on the connection with the external electronic device 1550. The processor 410 may execute the first function to identify the accident of the first type while the user is riding in the vehicle.

Figure 16:
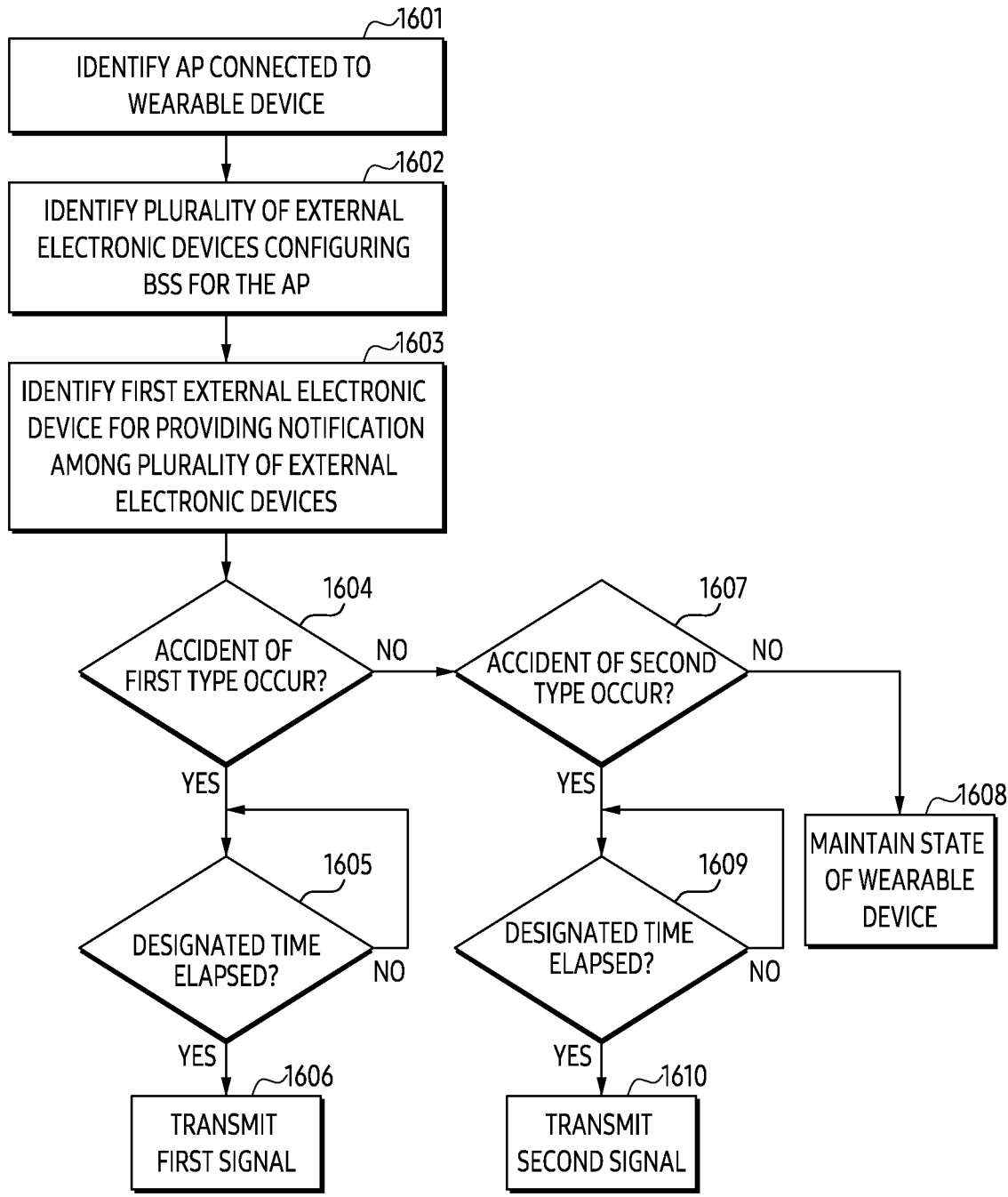
FIG. 16 is a flowchart illustrating an exemplary operation of a wearable device, according to an example embodiment.

FIG. 16 is a flowchart illustrating an exemplary operation of a wearable device, according to an embodiment.

In the following embodiment, each operation may be performed sequentially, but is not necessarily performed sequentially. For example, the order of each operation may be changed, and at least two operations may be performed in parallel.

According to an embodiment, operations 1601 to 1610 may be understood to be performed via at least one processor (e.g., the processor 410 of FIG. 4) of an electronic device (e.g., the electronic device 400 of FIG. 4).

Referring to FIG. 16, in operation 1601, the processor 410 may identify an access point (AP) connected, directly or indirectly, to the wearable device 400. For example, the wearable device 400 may be connected through a wireless LAN.

For example, the wearable device 400 may be positioned within coverage of the AP. The wearable device 400 may identify the AP based on at least one operation for network identification. The processor 410 may identify the AP based on active scanning and/or passive scanning. The processor 410 may establish a connection with the AP based on identifying the AP.

In operation 1602, the processor 410 may identify a plurality of external electronic devices configuring a basic service set (BSS) for the AP. For example, the AP may configure a BSS including the wearable device 400 and a plurality of external electronic devices. Each of the plurality of external electronic devices may be connected to the AP. The plurality of external electronic devices and the wearable device 400 may perform communication through the AP.

In operation 1603, the processor 410 may identify a first external electronic device for providing a notification from among the plurality of external electronic devices. For example, the processor 410 may provide a notification through the wearable device 400 according to the occurrence of one of the first accident or the second accident. The processor 410 may identify the first external electronic device for providing a notification when there is no response from the user through the wearable device 400.

For example, the processor 410 may identify a value indicating a priority for each of the plurality of external electronic devices. The processor 410 may identify a first external electronic device for outputting (or providing) a notification among the plurality of external electronic devices, based on the value indicating the priority for each of the plurality of external electronic devices.

For example, the value indicating the priority of each of the plurality of external electronic devices may be identified based on a distance between the wearable device 400 and each of the plurality of external electronic devices. The value indicating the priority of each of the plurality of external electronic devices may be set higher as a distance between each of the plurality of external electronic devices from the wearable device 400 is shorter. The processor 410 may identify the first external electronic device having the highest priority value among the plurality of external electronic devices.

According to an embodiment, the processor 410 may configure the BSS for the AP and identify a plurality of external electronic devices including components (e.g., a speaker) capable of providing sound output greater than or equal to a specified level. For example, the processor 410 may identify a first external electronic device including a component capable of providing the largest sound output among the plurality of external electronic devices.

In operation 1604, the processor 410 may identify whether the accident of the first type occurs. For example, the processor 410 may execute a first function for processing data obtained through at least one sensor, in order to identify the accident of the first type. The processor 410 may identify whether the accident of the first type occurs, based on the execution of the first function.

In operation 1605, the processor 410 may identify whether a designated time is/has elapsed from timing the accident of the first type occurred, in case that the accident of the first type occurs. For example, the processor 410 may identify whether a designated time is/has elapsed from timing the accident of the first type occurred based on the occurrence of the accident of the first type.

According to an embodiment, the wearable device 400 may include a display and a speaker. The processor 410 may output a first notification by using at least one of the display and the speaker, in response to identifying the accident of the first type. The processor 410 may output the first notification for notifying the occurrence of the accident of the first type. For example, the processor 410 may identify whether a designated time is/has elapsed from a time point at which the first notification is outputted.

According to an embodiment, when the designated time does not elapse, the processor 410 may perform operation 1605.

In operation 1606, when the designated time is/has elapsed, the processor 410 may transmit the first signal. For example, the processor 410 may transmit the first signal based on identifying that the designated time is/has elapsed. For example, the first signal may cause the first external electronic device to output a second notification. The first external electronic device may output the second notification for notifying the occurrence of the accident of the first type.

In operation 1607, when the accident of the first type does not occur, the processor may identify whether the accident of the second type occurs. For example, processor 410 may execute the second function for processing data obtained through at least one sensor, in order to identify the accident of the second type. The processor 410 may identify whether the accident of the second type occurs, based on the execution of the second function.

In operation 1608, the processor 410 may maintain a state of the wearable device, when the accident of the second type does not occur. When the accident of the second type does not occur, the processor 410 may monitor whether one of the accident of the first type and the accident of the second type occurs, through the sensor 430.

In operation 1609, the processor 410 may identify whether a designated time is/has elapsed from timing the accident of the second type occurred, in case that the accident of the second type occurs. For example, the processor 410 may identify whether a designated time is/has elapsed, based on the occurrence of the accident of the second type.

According to an embodiment, the processor 410 may output a third notification by using at least one of a display and a speaker, in response to identifying the accident of the second type. The processor 410 may output the third notification for notifying the occurrence of the accident of the second type. For example, the processor 410 may identify whether a designated time is/has elapsed from a time point at which the third notification is outputted.

According to an embodiment, when the designated time has not elapsed, the processor 410 may perform operation 1609.

In operation 1610, the processor 410 may transmit a second signal, when the designated time is/has elapsed. For example, the processor 410 may transmit the second signal based on identifying that the designated time is/has elapsed. For example, the second signal may cause the first external electronic device to output a fourth notification. The first external electronic device may output the fourth notification for notifying the occurrence of the accident of the second type.

Figure 17:
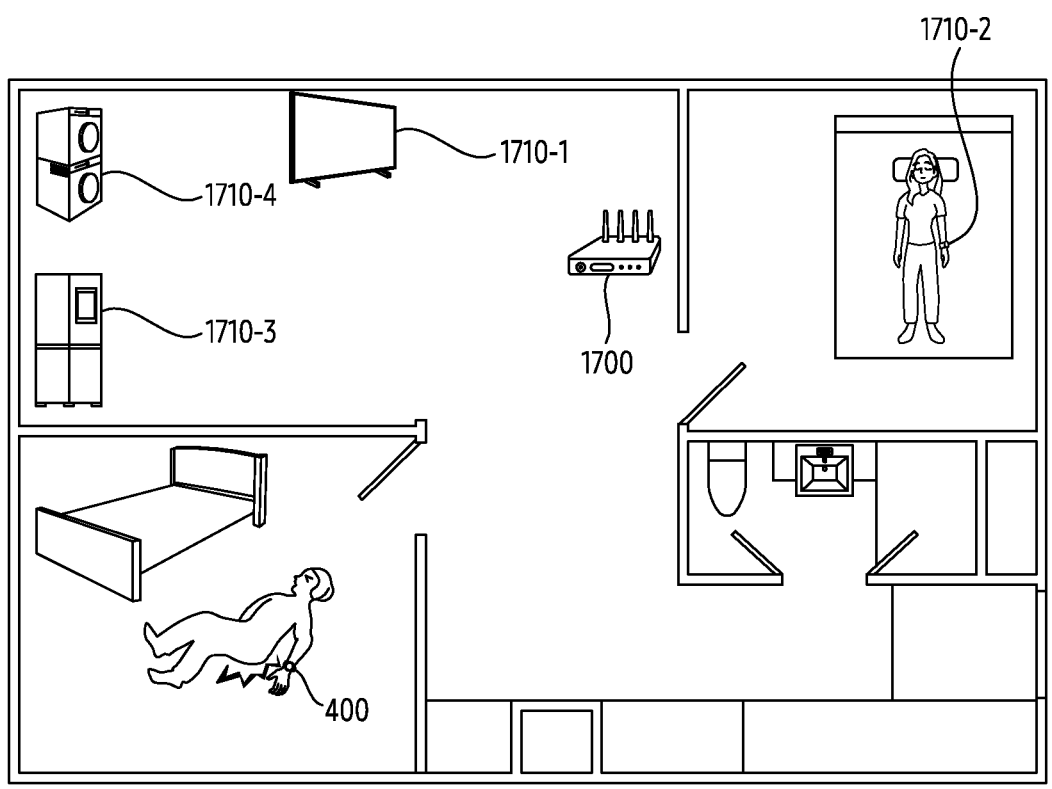
FIG. 17 illustrates an example of an operation of a wearable device according to an example embodiment.

FIG. 17 illustrates an example of an operation of a wearable device according to an embodiment.

Referring to FIG. 17, the wearable device 400 may be connected to an AP 1700. The processor 410 may identify a plurality of external electronic devices 1710-1, 1710-2, 1710-3, and 1710-4 that configure the BSS for the AP 1700.

The processor 410 may identify an external electronic device for providing a notification. For example, the processor 410 may identify the external electronic device 1710-1 including the component capable of providing the largest sound output among the plurality of external electronic devices, as an external electronic device for providing a notification. For example, the processor 410 may identify the external electronic device 1710-3 closest to the wearable device 400 as an external electronic device for providing a notification. For example, the processor 410 may identify the external electronic device 1710-2 worn by another user who is distinguished from the user of the wearable device 400, among the plurality of external electronic devices, as an external electronic device for providing a notification.

For example, the processor 410 may output a first notification by using at least one of the display and the speaker, based on the occurrence of the accident of the first type. The processor 410 may identify whether the designated time is/has elapsed from the time point at which the first notification is outputted. The processor 410 may identify whether an input (or movement) of a user of the wearable device 400 occurs during a designated time from the time point when the first notification is outputted. The processor 410 may transmit the first signal to the external electronic device for providing a notification, based on that the designated time is/has elapsed from the time point when the first notification is outputted. The first signal may cause the external electronic device for providing notification to output the fourth notification.

For example, the processor 410 may output a third notification by using at least one of a display and a speaker, based on the occurrence of the accident of the second type. The processor 410 may identify whether the designated time is/has elapsed from a time point when the third notification is outputted. The processor 410 may identify whether an input (or movement) of a user of the wearable device 400 occurs during a designated time from the time point when the third notification is outputted. The processor 410 may transmit a second signal to the external electronic device for providing the notification, based on that the designated time is/has elapsed from the time point when the third notification is outputted. The second signal may cause the external electronic device for providing a notification to output the fourth notification.

According to an embodiment, the processor 410 may output a notification (e.g., the second notification or the fourth notification) through the external electronic device for providing a notification, and then transmit a signal for providing notification through another external electronic device. The processor 410 may sequentially transmit a signal for providing a notification through a plurality of external electronic devices. The processor 410 may sequentially transmit a signal to the plurality of external electronic devices based on a value indicating a priority. According to an embodiment, the processor 410 may transmit a signal so that the plurality of external electronic devices simultaneously output a notification.

Figure 18:
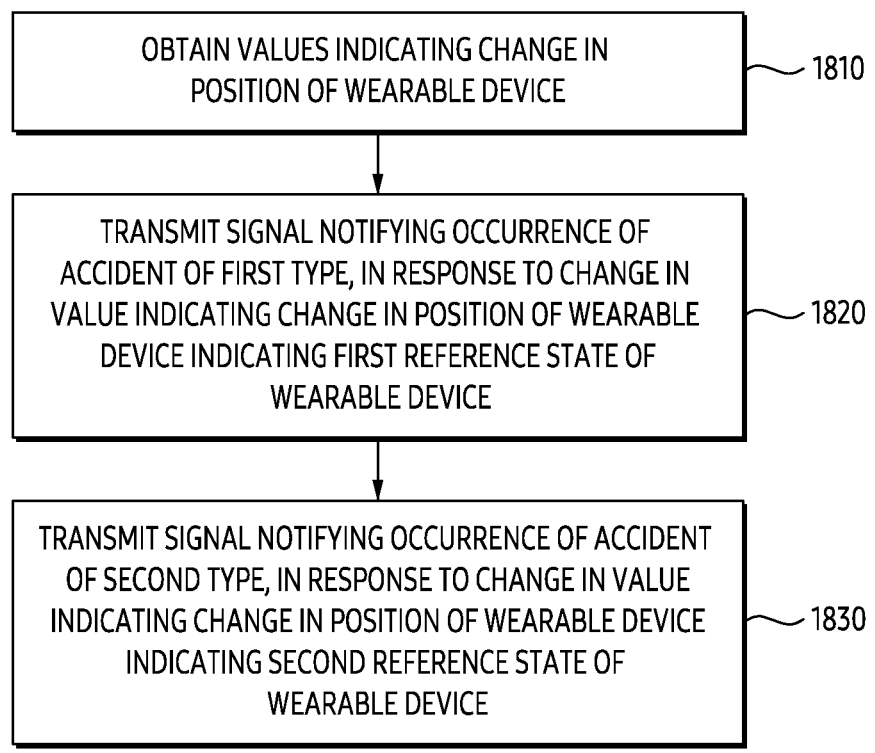
FIG. 18 is a flowchart illustrating an exemplary operation of a wearable device according to an example embodiment.

FIG. 18 is a flowchart illustrating an exemplary operation of a wearable device according to an embodiment.

In the following embodiment, each operation may be performed sequentially, but is not necessarily performed sequentially. For example, the order of each operation may be changed, and at least two operations may be performed in parallel.

According to an embodiment, operations 1810 to 1830 may be understood to be performed on a processor (e.g., the processor 410 of FIG. 4) of an electronic device (e.g., the electronic device 400 of FIG. 4).

In operation 1810, the processor 410 may obtain values indicating a change in a position of the wearable device 400. For example, the processor 410 may obtain values indicating a change in the position of the wearable device 400 by using the sensor 430. The processor 410 may identify a change in the position of the wearable device 400, based on values indicating the change in the position of the wearable device 400.

In operation 1820, the processor 410 may transmit a signal notifying the occurrence of the accident of the first type, in response to a change in a value indicating a change in a position of the wearable device 400 indicating a first reference state of the wearable device 400.

According to an embodiment, the wearable device 400 may be within the first reference state. For example, the first reference state may include a state in which an accident occurs while the user of the wearable device 400 is on board. For example, the first reference state may include a state in which a collision occurs while the user of the wearable device 400 is sleeping. For example, the first reference state may include a state in which a collision occurs while the wearable device 400 is positioned within the reference range.

According to an embodiment, the processor 410 may transmit a signal notifying the occurrence of the accident of the first type. For example, the processor 410 may transmit a first signal for calling a designated contact (e.g., SOS call or an emergency contact). The processor 410 may notify the occurrence of the accident of the first type, by transmitting the first signal.

In operation 1830, the processor 410 may transmit a signal notifying the occurrence of the accident of the second type, in response to a change in a value indicating a change in a position of the wearable device 400 indicating a second reference state of the wearable device 400.

According to an embodiment, the wearable device 400 may be in the second reference state. For example, the second reference state may include a state in which a shock occurs while the user of the wearable device 400 is walking. For example, the second reference state may include a state in which a collision occurs while the user of the wearable device 400 is waking up. For example, the second reference state may include a state in which a collision occurs while the wearable device 400 is positioned outside the reference range.

According to an embodiment, the processor 410 may transmit a signal notifying the occurrence of the accident of the second type. For example, the processor 410 may transmit a second signal for calling a designated contact (e.g., SOS call or an emergency contact). The processor 410 may notify the occurrence of the accident of the second type, by transmitting the second signal.

In an embodiment, a wearable device (e.g., 101; 200; 300; 400) may comprise a communication circuit (e.g., 420), at least one sensor (e.g., 430), and a processor (e.g., 410) operably coupled with the communication circuit (e.g., 420) and the at least one sensor (e.g., 430). The processor (e.g., 410) may be configured to identify a distance between the wearable device (e.g., 101; 200; 300; 400) and an external electronic device through the communication circuit (e.g., 420), during identifying that a user wearing the wearable device (e.g., 101; 200; 300; 400) is sleeping. The processor may be configured to, based at least in part on identifying that the distance that is less than a reference distance, compare data obtained through the at least one sensor (e.g., 430) to first reference data to identify a first state of the user while the user is sleeping, and execute a predetermined (or predefined) first function according to (or based on) a comparison between the data and the first reference data. The processor may be configured to, based at least in part on identifying that the distance that is greater than or equal to the reference distance, compare the data to second reference data to identify a second state of the user while the user is awake, which is distinct to the first reference data, and execute a predetermined (or predefined) second function according to (or based on) a comparison between the data and the second reference data.

According to an embodiment, the processor (e.g., 410) may be configured to identify movement of the user using the at least one sensor (e.g., 430). The processor (e.g., 410) may be configured to, based on identifying the movement of the user, identify the distance between the wearable device (e.g., 101; 200; 300; 400) and the external electronic device.

According to an embodiment, the processor (e.g., 410) may be configured to identify a distance between the wearable device (e.g., 101; 200; 300; 400) and the external electronic device only when the user moves. Accordingly, power consumption is reduced.

According to an embodiment, the processor (e.g., 410) may be configured to identify movement of the user using the at least one sensor (e.g., 430). The processor (e.g., 410) may be configured to identify that the movement of the user corresponds to movement of the external electronic device. The processor (e.g., 410) may be configured to, based on that the movement of the user corresponds to the movement of the external electronic device, identify that the user is awake. The processor (e.g., 410) may be configured to execute the predetermined second function according to (or based on) the comparison between the data and the second reference data.

According to an embodiment, since the processor e.g., 410 identifies whether the movement of the external electronic device corresponds to the user's movement, there is an effect of identifying whether the user moves while holding the external electronic device.

According to an embodiment, the first state may include a state in which the user falls while the user is sleeping. The second state may include a state in which the user falls while the user is awake.

According to an embodiment, the at least one sensor may include a PPG (photoplethysmography) sensor (e.g., 433) and an acceleration sensor (e.g., 431). The processor may be configured to, based on data related to acceleration of the wearable device identified using the acceleration sensor (e.g., 431), identify that a value representing the movement of the wearable device within a first time interval is greater than or equal to a first threshold value while the distance is less than the reference distance.

The processor (e.g., 410) may be configured, after identifying that the value representing the movement of the wearable device within the first time interval is greater than or equal to the first threshold value, based on data related to a heart rate of the user obtained (or identified) using the PPG sensor (e.g., 433), identify that a difference between a maximum heart rate and a minimum heart rate within a second time interval after the first time interval is greater than or equal to a threshold heart rate. The processor (e.g., 410) may be configured to, based on identifying that the difference between the maximum heart rate and the minimum heart rate within the second time interval is greater than or equal to the threshold heart rate, execute the first predetermined function.

According to an embodiment, the processor (e.g., 410) may be configured to, based on the data related to acceleration of the wearable device (e.g., 101; 200; 300; 400) identified using the acceleration sensor (e.g., 431), identify that a value representing the movement of the wearable device within a third time interval is greater than or equal to a second threshold value while the distance is greater than or equal to the reference distance. The processor (e.g., 410) may be configured to, based on identifying that the value representing the movement of the wearable device within the third time interval is greater than or equal to the second threshold value, execute the second predetermined function.

According to an embodiment, when a fall occurs to a user who is awake, there is an effect of reducing power consumption by not using a PPG sensor to identify the fall.

According to an embodiment, the processor (e.g., 410) may be configured to, based on identifying that the value representing the movement of the wearable device is greater than or equal to the second threshold value, bypass identifying that the difference between a maximum heart rate and a minimum heart rate within a fourth time interval after the third time interval is greater than or equal to the threshold heart rate, and execute the second predetermined function.

According to an embodiment, the processor (e.g., 410) may be configured to identify body information related to the user. The processor (e.g., 410) may be configured to identify, based on the body information of the user, the first reference data and the second reference data.

According to an embodiment, the processor (e.g., 410) may be configured to, based at least in part on identifying that the distance that is less than the reference distance, compare the data to the first reference data to identify the first state of the user while the user is sleeping by activating a first module e.g., (411) of the first module (e.g., 411) and a second module (e.g., 412) for identifying falls. The processor (e.g., 410) may be configured to, based at least in part on identifying that the distance that is greater than or equal to the reference distance, compare the data to the second reference data to identify the second state of the user while the user is awake by activating the second module (e.g., 412) of the first module (e.g., 411) and the second module (e.g., 412) for identifying falls.

According to an embodiment, the first module (e.g., 411) may be used to identify whether a fall occurs to the user while the user is sleeping, using a first model (e.g., 501) indicated by a plurality of first parameters. The second module (e.g., 412) may be used to identify whether a fall occurs to the user while the user is awake, using a second model (e.g., 502) indicated by a plurality of second parameters.

According to an embodiment, when the user is awake, whether a fall occurs to the user while the user is awake may be identified, based on the second module 412. When the user is sleeping, whether a fall occurs to the user while the user is sleeping may be identified, based on the first module 411.

According to an embodiment, the processor (e.g., 410) may be configured to, based on first information obtained using the at least one sensor (e.g., 430), identify that the user is sleeping within a first sleep identification interval. The processor (e.g., 410) may be configured to, based at least in part on identifying that the distance is greater than or equal to the reference distance, identify that the user is awake. The processor (e.g., 410) may be configured to, after identifying that the user is awake, based on identifying that the distance is changed within the reference distance, obtain second information using the at least one sensor (e.g., 430) within a second sleep identification interval shorter than the first sleep identification interval. The processor (e.g., 410) may be configured to, based on the second information, identify that the user is sleeping.

According to an embodiment, the processor (e.g., 410) may be configured to execute the predetermined first function, which is a function for notifying that the user is in an emergency situation according to (or based on) the comparison between the data and the first reference data.

According to an embodiment, the processor (e.g., 410) may be configured to transmit a signal for notifying a predetermined user that the user is in an emergency situation, using the external electronic device.

According to an embodiment, the processor (e.g., 410) may be configured to provide a first notification representing that a fall has occurred to the user while the user is sleeping, according to (or based on) the comparison between the data and the first reference data. The processor (e.g., 410) may be configured to provide a second notification representing that a fall has occurred to the user while the user is awake, according to (or based on) the comparison between the data and the second reference data.

According to an embodiment, the processor (e.g., 410) may be configured to identify a distance between the wearable device (e.g., 101; 200; 300; 400) and another external electronic device. The processor (e.g., 410) may be configured to identify, based on the distance between the wearable device (e.g., 101; 200; 300; 400) and the other external electronic device, whether the user is sleeping.

According to an embodiment, the processor (e.g., 410) may be configured to receive information related to a distance between the external electronic device and the other external electronic device from the external electronic device connected to the other external electronic device. The processor (e.g., 410) may be configured to, based on the distance between the wearable device and the external electronic device and the distance between the external electronic device and the other external electronic device, identify a distance between the wearable device and the other external electronic device.

According to an embodiment, a method of a wearable device (e.g., 101; 200; 300; 400) may comprise identifying a distance between the wearable device (e.g., 101; 200; 300; 400) and an external electronic device through a communication circuit (e.g., 420) of the wearable device (e.g., 101; 200; 300; 400), during identifying that a user wearing the wearable device (e.g., 101; 200; 300; 400) is sleeping. The method may comprise, based at least in part on identifying that the distance is less than a reference distance, comparing data obtained through at least one sensor (e.g., 430) of the wearable device (e.g., 101; 200; 300; 400) to first reference data to identify a first state of the user while the user is sleeping, and executing a predetermined first function according to (or based on) a comparison between the data and the first reference data. The method may comprise, based at least in part on identifying that the distance is greater than or equal to the reference distance, comparing the data to second reference data to identify a second state of the user while the user is awake, which is distinct to the first reference data, and executing a predetermined second function according to (or based on) a comparison between the data and the second reference data.

According to an embodiment, the method may comprise, based on data related to acceleration of the wearable device (e.g., 101; 200; 300; 400) identified using an acceleration sensor (e.g., 431) of the at least one sensor (e.g., 430), identifying that a value representing the movement of the wearable device within a first time interval is greater than or equal to a first threshold value while the distance is less than the reference distance. The method may comprise, after identifying that the value representing the movement of the wearable device within the first time interval is greater than or equal to the first threshold value, based on data related to a heart rate of the user identified using a PPG sensor (e.g., 433) of the at least one sensor (e.g., 430), identifying that a difference between a maximum heart rate and a minimum heart rate within a second time interval after the first time interval is greater than or equal to a threshold heart rate. The method may comprise, based on identifying that the difference between the maximum heart rate and the minimum heart rate within the second time interval is greater than or equal to the threshold heart rate, executing the first predetermined function.

According to an embodiment, the method may comprise, based on the data related to acceleration of the wearable device (e.g., 101; 200; 300; 400) identified using the acceleration sensor (e.g., 431), identifying that a value representing the movement of the wearable device within a third time interval is greater than or equal to a second threshold value while the distance is greater than or equal to the reference distance. The method may comprise, based on identifying that the value representing the movement of the wearable device within the third time interval is greater than or equal to the second threshold value, executing the second predetermined function.

According to an embodiment, the method may comprise, based on identifying that the value representing the movement of the wearable device is greater than or equal to the second threshold value, bypass identifying that the difference between a maximum heart rate and a minimum heart rate within a fourth time interval after the third time interval is greater than or equal to the threshold heart rate, and executing the second predetermined function.

According to an embodiment, there is an effect of identifying whether a fall occurs to the user while the user is sleeping. According to an embodiment, there is an effect of accurately detecting the user's fall according to the user's state (e.g., a sleeping state or a weather state) by identifying whether the user is leaving the bed (or sleeping), and whether the user is returning. According to an embodiment, the processor 410 identifies body information about the user and thus changes a parameter (e.g., threshold heart rate) for identifying a fall, thereby providing an enhanced user experience.

According to an embodiment, a wearable device (e.g., 101; 200; 300; 400) may include a communication circuit (e.g., 420), at least one sensor (e.g., 430), and at least one processor (e.g., 410) operably connected to the communication circuit and the at least one sensor. The at least one processor may be configured to identify that the wearable device is positioned within a reference range via at least the communication circuit. The at least one processor may be configured to, while the wearable device is positioned within the reference range, execute a first function for processing data obtained through the at least one sensor, for identifying that an accident of a first type occurred. The at least one processor may be configured to, while the wearable device is positioned outside of the reference range, execute a second function for processing the data, for identifying that an accident of a second type occurred.

According to an embodiment, the at least one processor may be configured to control to transmit, based on occurrence of the accident of the first type, a first signal indicating the occurrence of the accident of the first type. The at least one processor may be configured to control to transmit, based on occurrence of the accident of the second type, a second signal indicating the occurrence of the accident of the second type. The first signal may be configured to cause peripheral devices of the wearable device to provide a notification indicating the occurrence of the accident of the first type. The second signal may be configured to cause peripheral devices of the wearable device to provide a notification indicating the occurrence of the accident of the second type.

According to an embodiment, the reference range may be set based on a distance between an external electronic device connected to the wearable device and the wearable device. The at least one processor may be configured to identify that the wearable device is positioned outside the reference range based on the distance between the wearable device and the external electronic device being greater than a threshold distance. The at least one processor may be configured to identify that the wearable device is positioned within the reference range based on the distance between the wearable device and the external electronic device being less than or equal to the threshold distance.

The at least one processor may be configured to set the reference range based on a designated distance from a position that a state of a user of the wearable device is identified as a first state.

The at least one processor may be configured to enable a first number of sensors, based on execution of the first function. The at least one processor may be configured to enable a second number, which is greater than or equal to the first number, of sensors, based on execution of the second function.

According to an embodiment, first power consumption while the first function is being executed may be less than second power consumption while the second function is being executed.

According to an embodiment, the at least one processor may be configured to identify an access point (AP) connected to the wearable device. The at least one processor may be configured to identify a plurality of external electronic devices configuring a basic service set (BSS) related to the AP. The at least one processor may be configured to identify a first external electronic device to provide a notification among the plurality of the external electronic devices.

According to an embodiment, a wearable device may comprise a display and a speaker. The at least one processor may be configured to control to output a first notification via at least one of the display or the speaker, in response to identifying the occurrence of the accident of the first type. The at least one processor may be configured to, based on a designated time is/has elapsed from timing when the first notification is outputted, control to transmit a first signal for causing the first external electronic device to output a second notification.

According to an embodiment, the at least one processor may be configured to control to output a third notification via at least one of the display or the speaker, in response to identifying the occurrence of the accident of the second type. The at least one processor may be configured to, based on that the designated time is/has elapsed from timing when the third notification is outputted, control to transmit a second signal for causing the first external electronic device to output a fourth notification.

The at least one processor may be configured to identify a value indicating a priority for each of the plurality of external electronic devices. The at least one processor may be configured to identify the first external electronic device to provide a notification among the plurality of the external electronic devices, based on the value indicating the priority for each of the plurality of external electronic devices.

According to an embodiment, the at least one processor is configured so that the value indicating the priority for each of the plurality of external electronic devices may be to be identified based on a distance between the wearable device and each of the plurality of external electronic devices.

According to an embodiment, the at least one processor may be configured to identify the plurality of external electronic devices comprising a component capable of providing an output of sound above a specified level.

According to an embodiment, a method of a wearable device may comprise identifying that the wearable device is positioned within a reference range via a communication circuit (e.g., 420) of the wearable device (e.g., 101; 200; 300; 400). The method may comprise, while the wearable device is positioned within the reference range, executing a first function which processes data obtained through at least one sensor (e.g., 430) of the wearable device, for identifying that an accident of a first type occurred. The method may comprise, while the wearable device is positioned outside of the reference range, executing a second function which processes the data, for identifying that an accident of a second type occurred.

According to an embodiment, the method may comprise transmitting, based on occurrence of the accident of the first type, a first signal indicating the occurrence of the accident of the first type. The method may comprise transmitting, based on occurrence of the accident of the second type, a second signal indicating the occurrence of the accident of the second type. The first signal may be configured to cause peripheral devices to provide a notification indicating the occurrence of the accident of the first type. The second signal may be configured to cause peripheral devices to provide a notification indicating the occurrence of the accident of the second type.

According to an embodiment, the reference range may be set based on a distance between an external electronic device connected to the wearable device and the wearable device. The method may comprise identifying that the wearable device is positioned outside the reference range based on the distance between the wearable device and the external electronic device being greater than a threshold distance. The method may comprise identifying that the wearable device is positioned within the reference range based on the distance between the wearable device and the external electronic device being less than or equal to the threshold distance.

According to an embodiment, first power consumption while the first function is being executed may be less than second power consumption while the second function is being executed.

According to an embodiment, the method may comprise identifying an access point (AP) connected to the wearable device. The method may comprise identifying a plurality of external electronic devices configuring a basic service set (BSS) related to the AP. The method may comprise identifying a first external electronic device to provide a notification among the plurality of the external electronic devices.

According to an embodiment, the method may comprise outputting a first notification using at least one of a display of the wearable device or a speaker of the wearable device, in response to identifying the occurrence of the accident of the first type. The method may comprise transmitting a first signal configured for causing the first external electronic device to output a second notification, based on a designated time is/has elapsed from timing when the first notification is outputted.

According to an embodiment, the method may comprise outputting a third notification using at least one of the display or the speaker, in response to identifying the occurrence of the accident of the second type. The method may comprise transmitting a second signal configured to causing the first external electronic device to output a fourth notification, based on that the designated time is/has elapsed from timing when the third notification is outputted.

According to an embodiment, the method may comprise identifying a value indicating a priority for each of the plurality of external electronic devices. The method may comprise identifying the first external electronic device to provide a notification among the plurality of the external electronic devices, based on the value indicating the priority for each of the plurality of external electronic devices.

Each embodiment herein may be used in combination with any other embodiment(s) described herein. Reference numerals herein are used for purposes of example only, and are not limiting.

In various embodiments of the present disclosure, "based on" as used herein covers based at least in part on.

The electronic device according to various embodiments may be one of various types of electronic devices. The electronic devices may include, for example, a portable communication device (e.g., a smartphone), a computer device, a portable multimedia device, a portable medical device, a camera, a wearable device, or a home appliance. According to an embodiment of the disclosure, the electronic devices are not limited to those described above.

It should be appreciated that various embodiments of the present disclosure and the terms used therein are not intended to limit the technological features set forth herein to particular embodiments and include various changes, equivalents, or replacements for a corresponding embodiment. With regard to the description of the drawings, similar reference numerals may be used to refer to similar or related elements. It is to be understood that a singular form of a noun corresponding to an item may include one or more of the things, unless the relevant context clearly indicates otherwise. As used herein, each of such phrases as "A or B," "at least one of A and B," "at least one of A or B," "A, B, or C," "at least one of A, B, and C," and "at least one of A, B, or C," may include any one of, or all possible combinations of the items enumerated together in a corresponding one of the phrases. As used herein, such terms as "1st" and "2nd," or "first" and "second" may be used to simply distinguish a corresponding component from another, and does not limit the components in other aspect (e.g., importance or order). It is to be understood that if an element (e.g., a first element) is referred to, with or without the term "operatively" or "communicatively", as "coupled with," "coupled to," "connected with," or "connected to" another element (e.g., a second element), it means that the element may be coupled with the other element directly (e.g., wiredly), wirelessly, or via at least a third element(s).

As used in connection with various embodiments of the disclosure, the term "module" may include a unit implemented in hardware, software, or firmware, and may interchangeably be used with other terms, for example, "logic," "logic block," "part," or "circuitry". A module may be a single integral component, or a minimum unit or part thereof, adapted to perform one or more functions. For example, according to an embodiment, the module may be implemented in a form of an application-specific integrated circuit (ASIC). Thus, each "module" herein may comprise circuitry.

Various embodiments as set forth herein may be implemented as software (e.g., the program 140) including one or more instructions that are stored in a storage medium (e.g., internal memory 136 or external memory 138) that is readable by a machine (e.g., the electronic device 101). For example, a processor (e.g., the processor 120) of the machine (e.g., the electronic device 101) may invoke at least one of the one or more instructions stored in the storage medium, and execute it, with or without using one or more other components under the control of the processor. This allows the machine to be operated to perform at least one function according to the at least one instruction invoked. The one or more instructions may include a code generated by a compiler or a code executable by an interpreter. The machine-readable storage medium may be provided in the form of a non-transitory storage medium. Wherein, the term "non-transitory" simply means that the storage medium is a tangible device, and does not include a signal (e.g., an electromagnetic wave), but this term does not differentiate between where data is semi-permanently stored in the storage medium and where the data is temporarily stored in the storage medium.

According to an embodiment, a method according to various embodiments of the disclosure may be included and provided in a computer program product. The computer program product may be traded as a product between a seller and a buyer. The computer program product may be distributed in the form of a machine-readable storage medium (e.g., compact disc read only memory (CD-ROM)), or be distributed (e.g., downloaded or uploaded) online via an application store (e.g., PlayStore™), or between two user devices (e.g., smart phones) directly. If distributed online, at least part of the computer program product may be temporarily generated or at least temporarily stored in the machine-readable storage medium, such as memory of the manufacturer's server, a server of the application store, or a relay server.

According to various embodiments, each component (e.g., a module or a program) of the above-described components may include a single entity or multiple entities, and some of the multiple entities may be separately disposed in different components. According to various embodiments, one or more of the above-described components may be omitted, or one or more other components may be added. Alternatively or additionally, a plurality of components (e.g., modules or programs) may be integrated into a single component. In such a case, according to various embodiments, the integrated component may still perform one or more functions of each of the plurality of components in the same or similar manner as they are performed by a corresponding one of the plurality of components before the integration. According to various embodiments, operations performed by the module, the program, or another component may be carried out sequentially, in parallel, repeatedly, or heuristically, or one or more of the operations may be executed in a different order or omitted, or one or more other operations may be added.

While the disclosure has been illustrated and described with reference to various embodiments, it will be understood that the various embodiments are intended to be illustrative, not limiting. It will further be understood by those skilled in the art that various changes in form and detail may be made without departing from the true spirit and full scope of the disclosure, including the appended claims and their equiva-

What is claimed is:

1. A wearable device comprising:
a communication circuit;
at least one sensor; and
at least one processor operably coupled with the communication circuit and the at least one sensor, wherein the at least one processor is configured to:
identify that the wearable device is positioned within a reference range via at least the communication circuit;
while the wearable device is positioned within the reference range, execute a first function for processing data obtained through the at least one sensor, for identifying that an accident of a first type has occurred; and
while the wearable device is positioned outside of the reference range, execute a second function for processing the data, for identifying that an accident of a second type has occurred.

2. The wearable device of claim 1, the at least one processor is further configured to:
control to transmit, based on occurrence of the accident of the first type, a first signal of the accident of the first type,
control to transmit, based on occurrence of the accident of the second type, a second signal indicating the occurrence of the accident of the second type, and
wherein the first signal is configured to cause peripheral devices to provide a notification indicating the occurrence of the accident of the first type, and
wherein the second signal is configured to cause peripheral devices to provide a notification indicating the occurrence of the accident of the second type.

3. The wearable device of claim 1, wherein the reference range is based on a distance between an external electronic device connected to the wearable device and the wearable device,
wherein the at least one processor is further configured to:
identify that the wearable device is positioned outside the reference range based on the distance between the wearable device and the external electronic device being greater than a threshold distance, and
identify that the wearable device is positioned within the reference range based on the distance between the wearable device and the external electronic device being less than or equal to the threshold distance.

4. The wearable device of claim 1, wherein the at least one processor is further configured to:
set the reference range based on a designated distance from a position that a state of a user of the wearable device is identified as a first state.

5. The wearable device of claim 1, wherein the at least one processor is further configured to:
based on execution of the first function, enable a first number of sensors, and
based on execution of the second function, enable a second number of sensors, wherein the second number is greater than or equal to the first number.

6. The wearable device of claim 5, wherein first power consumption while the first function is being executed is less than second power consumption while the second function is being executed.

7. The wearable device of claim 1, wherein the at least one processor is further configured to:
identify an access point (AP) connected to the wearable device,
identify a plurality of external electronic devices configuring a basic service set (BSS) related to the AP, and
identify a first external electronic device to provide a notification among the plurality of the external electronic devices.

8. The wearable device of claim 7, further comprising:
a display; and
a speaker,
wherein the at least one processor is further configured to:
in response to identifying the occurrence of the accident of the first type, control to output a first notification via at least one of the display or the speaker, and
based on a designated time having elapsed from timing when the first notification is outputted, control to transmit a first signal for causing the first external electronic device to output a second notification.

9. The wearable device of claim 8, wherein the at least one processor is further configured to:
in response to identifying the occurrence of the accident of the second type, control to output a third notification via at least one of the display or the speaker, and
based on the designated time having elapsed from timing when the third notification is outputted, control to transmit a second signal for causing the first external electronic device to output a fourth notification.

10. The wearable device of claim 7, wherein the at least one processor is further configured to:
identify a value indicating a priority for each of the plurality of external electronic devices, and
based on the value indicating the priority for each of the plurality of external electronic devices, identify the first external electronic device to provide a notification among the plurality of the external electronic devices.

11. The wearable device of claim 10, wherein the at least one processor is configured so that the value indicating the priority for each of the plurality of external electronic devices is to be identified based on a distance between the wearable device and each of the plurality of external electronic devices.

12. The wearable device of claim 7, wherein the at least one processor is further configured to identify the plurality of external electronic devices comprising a component capable of providing an output of sound above a specified level.

13. A method of a wearable device, the method comprising:
identifying that the wearable device is positioned within a reference range via a communication circuit of the wearable device;
while the wearable device is positioned within the reference range, executing a first function which processes data obtained through at least one sensor of the wearable device, for identifying that an accident of a first type occurred; and
while the wearable device is positioned outside of the reference range, executing a second function which processes the data, for identifying that an accident of a second type occurred.

14. The method of claim 13, further comprising:
transmitting, based on occurrence of the accident of the first type, a first signal indicating the occurrence of the accident of the first type, and transmitting, based on occurrence of the accident of the second type, a second signal indicating the occurrence of the accident of the second type,
wherein the first signal is configured to cause peripheral devices to provide a notification indicating the occurrence of the accident of the first type, and
wherein the second signal is configured to cause peripheral devices to provide a notification indicating the occurrence of the accident of the second type.

15. The method of claim 13, wherein the reference range is based on a distance between an external electronic device connected to the wearable device and the wearable device, wherein the method further comprises:
identifying that the wearable device is positioned outside the reference range based on the distance between the wearable device and the external electronic device being greater than a threshold distance, and
identifying that the wearable device is positioned within the reference range based on the distance between the wearable device and the external electronic device being less than or equal to the threshold distance.

16. The method of claim 13, wherein first power consumption while the first function is being executed is less than second power consumption while the second function is being executed.

17. The method of claim 13, further comprising:
identifying an access point (AP) connected to the wearable device,
identifying a plurality of external electronic devices configuring a basic service set (BSS) related to the AP, and
identifying a first external electronic device to provide a notification among the plurality of the external electronic devices.

18. The method of claim 17, further comprising:
in response to identifying the occurrence of the accident of the first type, outputting a first notification using at least one of a display of the wearable device or a speaker of the wearable device, and
based on a designated time having elapsed from timing when the first notification is outputted, transmitting a first signal configured for causing the first external electronic device to output a second notification.

19. The method of claim 18, further comprising:
in response to identifying the occurrence of the accident of the second type, outputting a third notification using at least one of the display or the speaker, and
based on the designated time having elapsed from timing when the third notification is outputted, transmitting a second signal configured for causing the first external electronic device to output a fourth notification.

20. The method of claim 17, further comprising:
identifying a value indicating a priority for each of the plurality of external electronic devices, and
based on the value indicating the priority for each of the plurality of external electronic devices, identifying the first external electronic device to provide a notification among the plurality of the external electronic devices.

* * * * *